US012609198B2

(12) United States Patent  
Ukrainksy et al.

(10) Patent No.: US 12,609,198 B2  
(45) Date of Patent: Apr. 21, 2026

(54) MEDICAL DIAGNOSTIC KIT

(71) Applicants: Gennady Ukrainksy, New York, NY (US); Rada Sumareva, New York, NY (US); Daniel Kogan, Brooklyn, NY (US); Sergei Kuznetsov, Voorhees, NY (US)

(72) Inventors: Gennady Ukrainksy, New York, NY (US); Rada Sumareva, New York, NY (US); Daniel Kogan, Brooklyn, NY (US); Sergei Kuznetsov, Voorhees, NY (US)

(73) Assignee: ZIPHYCARE INC, New York, NY (US)

( * ) Notice: Subject to any disclaimer, the term of this patent is extended or adjusted under 35 U.S.C. 154(b) by 1174 days.

(21) Appl. No.: 17/542,317

(22) Filed: Dec. 3, 2021

(65) Prior Publication Data

US 2022/0181019 A1 Jun. 9, 2022

Related U.S. Application Data

(60) Provisional application No. 63/121,302, filed on Dec. 4, 2020, provisional application No. 63/120,800, filed on Dec. 3, 2020.

(51) Int. Cl.  
*G16H 40/67* (2018.01)  
*A61B 50/20* (2016.01)  
(52) U.S. Cl.  
CPC ............. *G16H 40/67* (2018.01); *A61B 50/20* (2016.02)  
(58) Field of Classification Search  
CPC ........ G16H 40/67; G16H 10/60; G16H 40/20; G16H 50/20; G16H 80/00; A61B 50/20; A61B 5/0022  
See application file for complete search history.

(56) References Cited

U.S. PATENT DOCUMENTS

2015/0068942 A1 * 3/2015 Gerstner ............... A61B 50/30  
206/370

FOREIGN PATENT DOCUMENTS

CN 203898275 U * 10/2014  
DE 102013214080 A1 * 1/2015 ............ G16H 40/67  
KR 20200005744 A 1/2020

OTHER PUBLICATIONS

Howard Med Technology Solutions: äTelehealth Solutionsä, Jul. 31, 2009 (2-19=07=31), pp. 1-2, XP093117527, Ellisville MS 39437, USA, https://media.howard.com/literature/Technology/Howard/ (Year: 2009).*

(Continued)

*Primary Examiner* — Michael W Kahelin  
*Assistant Examiner* — Attiya Sayyada Hussaini  
(74) *Attorney, Agent, or Firm* — Ashok Tankha

(57) ABSTRACT

A medical diagnostic kit (MDK) includes a universal cable storage compartment (UCSC), a deck, and switchable multi-port hubs (SMPHs). Configurable cable compartments in the UCSC accommodate cables of clinical examination devices (CEDs) without mutual entanglement. The deck positioned on the UCSC supports the CEDs and includes cutouts into the UCSC for cable management. The SMPHs permanently connect CED cable connectors and selectively power and communicate data with the CED(s). An internal energy storage device (ESD) receives power from a multi-port charger (MPC) during charging, and delivers the power to the SMPHs for powering and communicating data with the CED(s) when the casing is opened. An activated, hubs disconnection switch interrupts power delivery from the ESD to the SMPHs when the casing is closed. The MDK includes a diagnostic computer with a software application for activating the CED(s), executing media conference con- (Continued)

nections, managing medical data, and facilitating remote real-time medical examinations.

25 Claims, 34 Drawing Sheets

(56) References Cited

OTHER PUBLICATIONS

Howard Med Technology Solutions, "Howard Medical Rugged Telehealth Kits", YouTube, uploaded by Howard Medical , Aug. 31, 2020, https://www.youtube.com/watch?v=Y3OwpadNhjU (Year: 2020).*

Rugged Telehealth Kits, Howard Technology Solutions, Jul. 2019, www.howardcomputers.com/Landing/rugged_telehealth_kits.cfm (Year: 2019).*

CN 203898275 U Translation (Year: 2014).*

DE102013214080A1 Translation (Year: 2015).*

* cited by examiner

FIG. 17

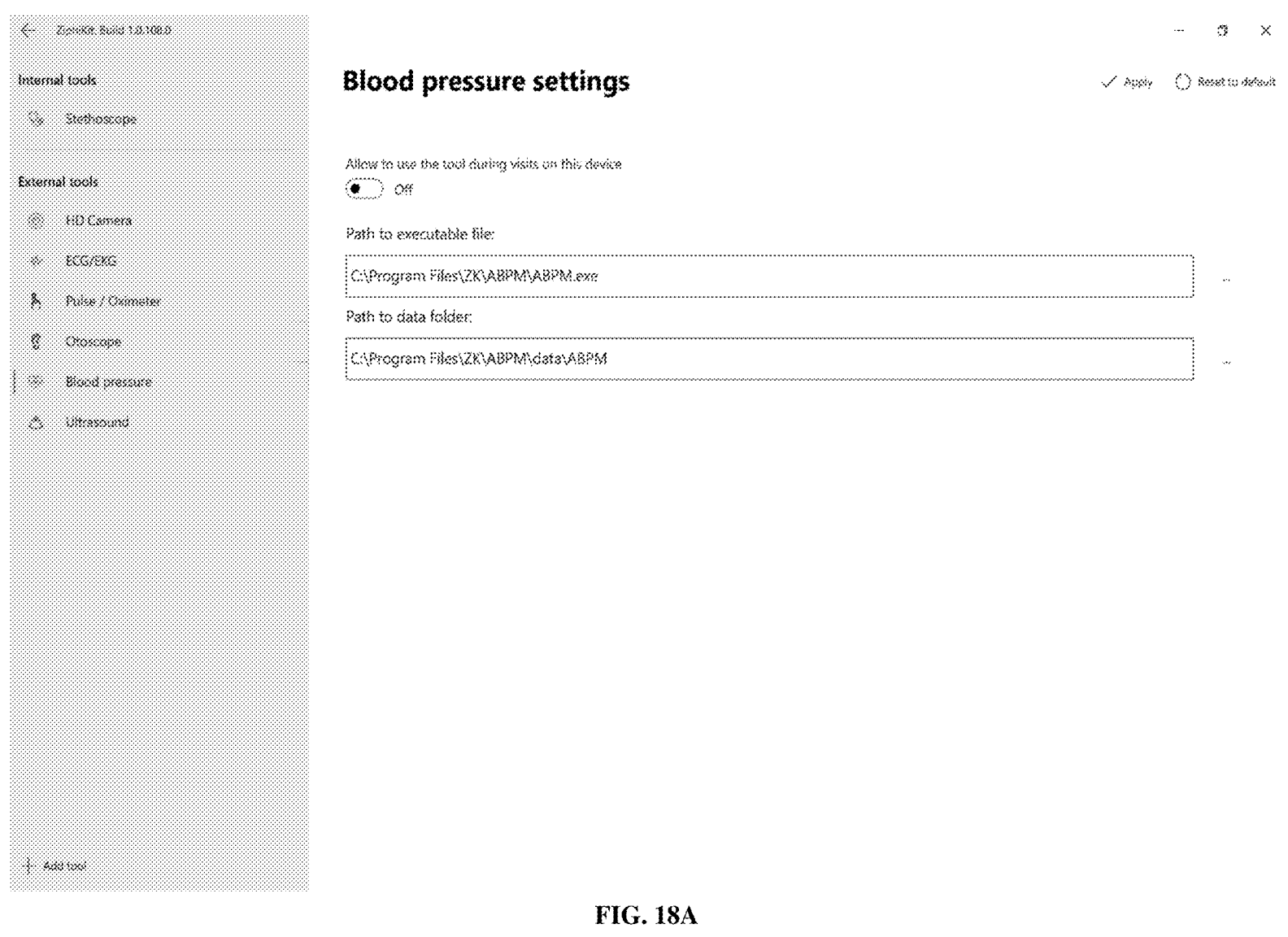

Blood pressure settings

Allow to use the tool during visits on this device

◉ Off

Path to executable file:

C:\Program Files\ZK\ABPM\ABPM.exe

Path to data folder:

C:\Program Files\ZK\ABPM\data\ABPM

✓ Apply    ○ Reset to default

Zoctor Build 19.1010

Internal tools

Stethoscope

External tools

HD Camera

ECG/EKG

Pulse / Oximeter

Otoscope

Blood pressure

Ultrasound

Add tool

FIG. 18A

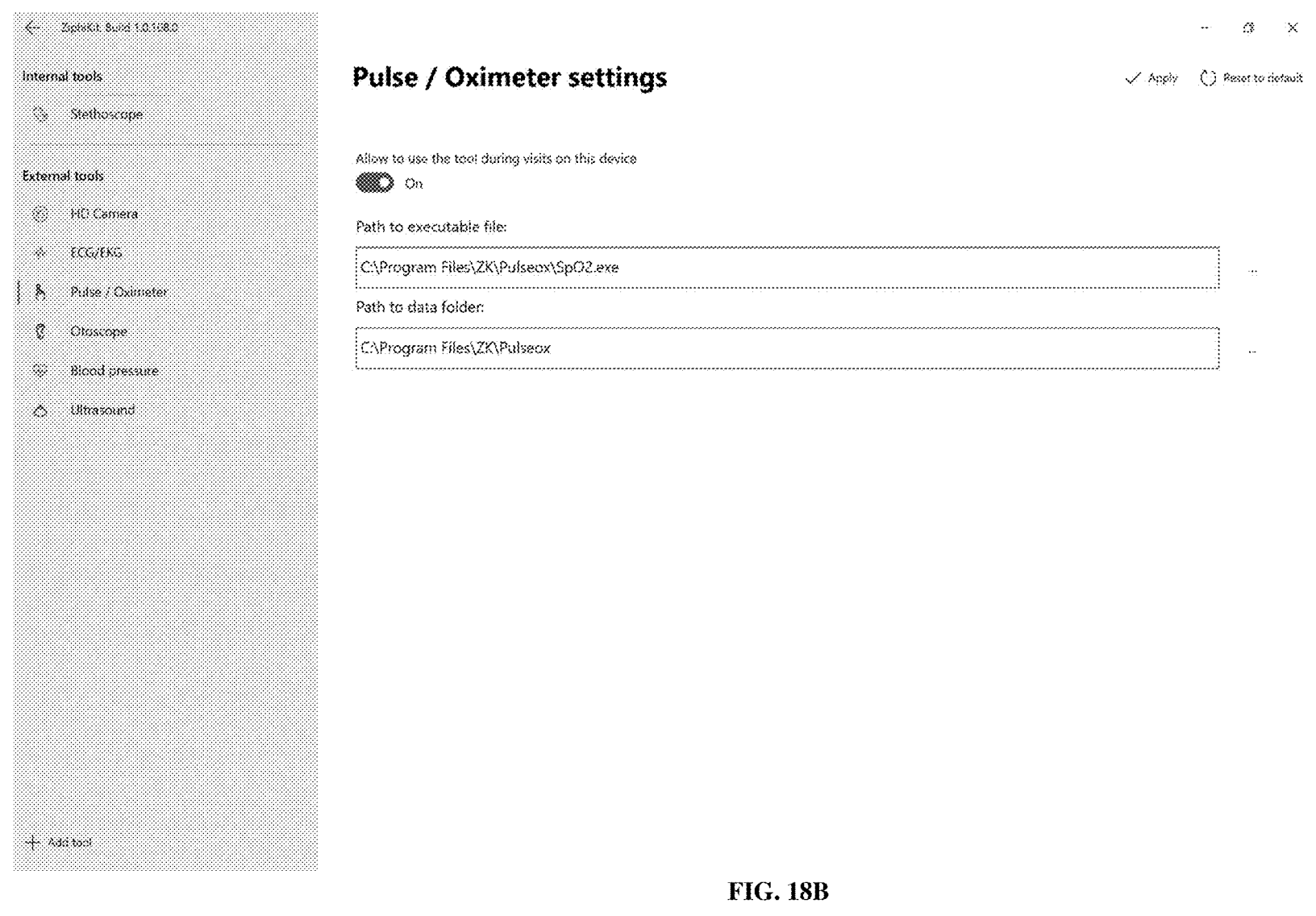

Zapikit Build 10.18.0

Internal tools

Stethoscope

External tools

HD Camera

ECG/EKG

Pulse / Oximeter

Otoscope

Blood pressure

Ultrasound

+ Add tool

Pulse / Oximeter settings

Allows to use the tool during visits on this device

On

Path to executable file:

C:\Program Files\ZK\Pulseox\SpO2.exe

Path to data folder:

C:\Program Files\ZK\Pulseox

✓ Apply    ↻ Reset to default

FIG. 18B

Ultrasound settings

Allow to use the ultrasound tool during visits on this device

◉ Off

Path to executable file:

D:\ZYPHY_KIT_HOME\Ultrasound\SeeMore\SeeMoreGP.exe

✓ Apply    ○ Reset to default

Internal tools

· Stethoscope

External tools

· HD Camera

· ECG/EKG

· Pulse / Oximeter

· Otoscope

· Blood pressure

· Ultrasound

+ Add tool

Otoscope settings

Allow to use this tool during visits on this device

Off

Path to executable file:

C:\Program Files\ZK\Otoscope\Viewer.exe

Path to data folder:

C:\Program Files\ZK\Otoscope\Snapshots

Apply    Reset to default

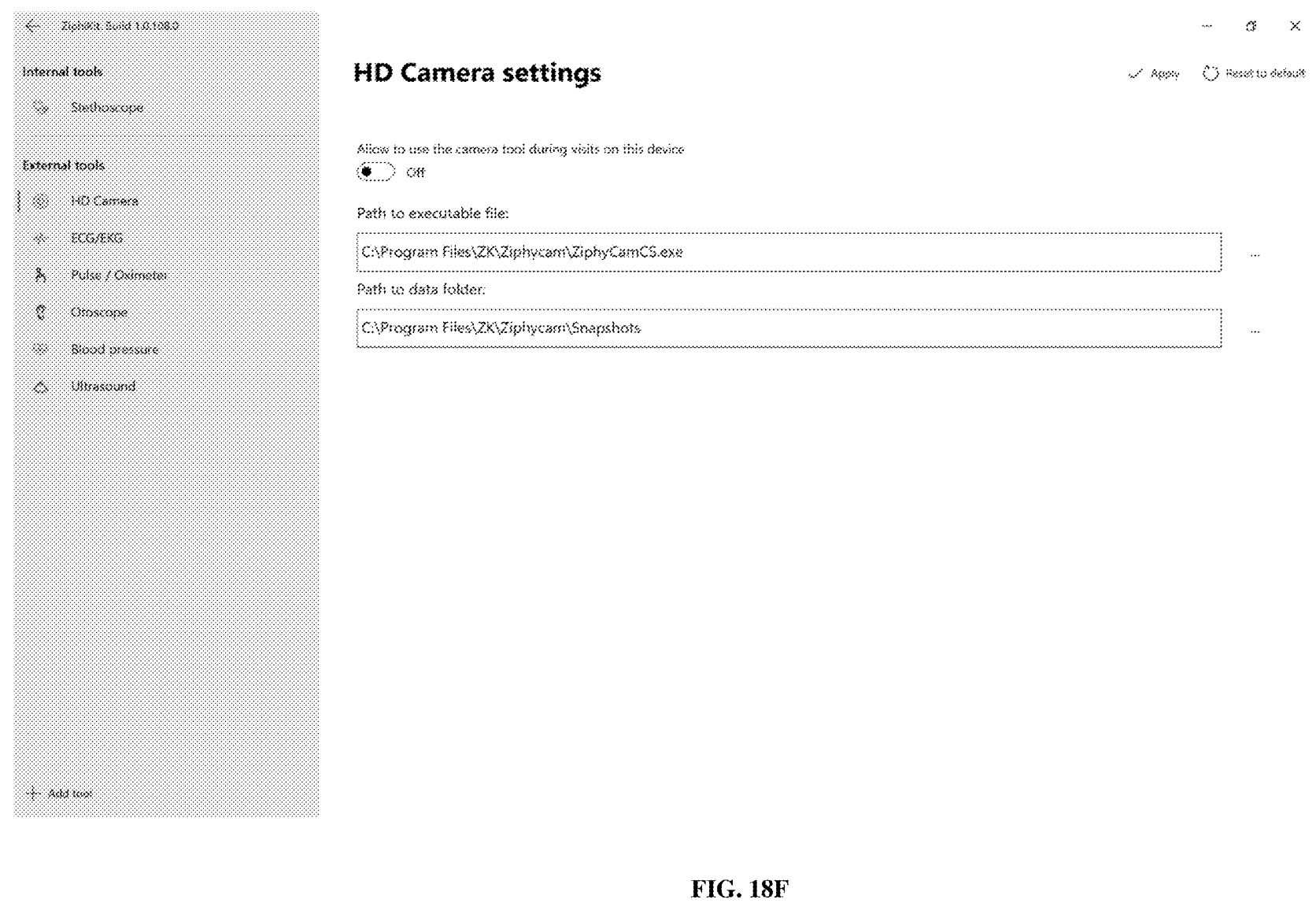

HD Camera settings

Allow to use the camera tool during visits on this device ( ) Off

Path to executable file:

C:\Program Files\ZK\Ziphycam\ZiphyCamCS.exe

Path to data folder:

C:\Program Files\ZK\Ziphycam\Snapshots

Ziphix Suite 1.0.1000

Internal tools
   Stethoscope

External tools
   HD Camera
   ECG/EKG
   Pulse / Oximeter
   Otoscope
   Blood pressure
   Ultrasound Add tool Apply    Reset to default

FIG. 18F

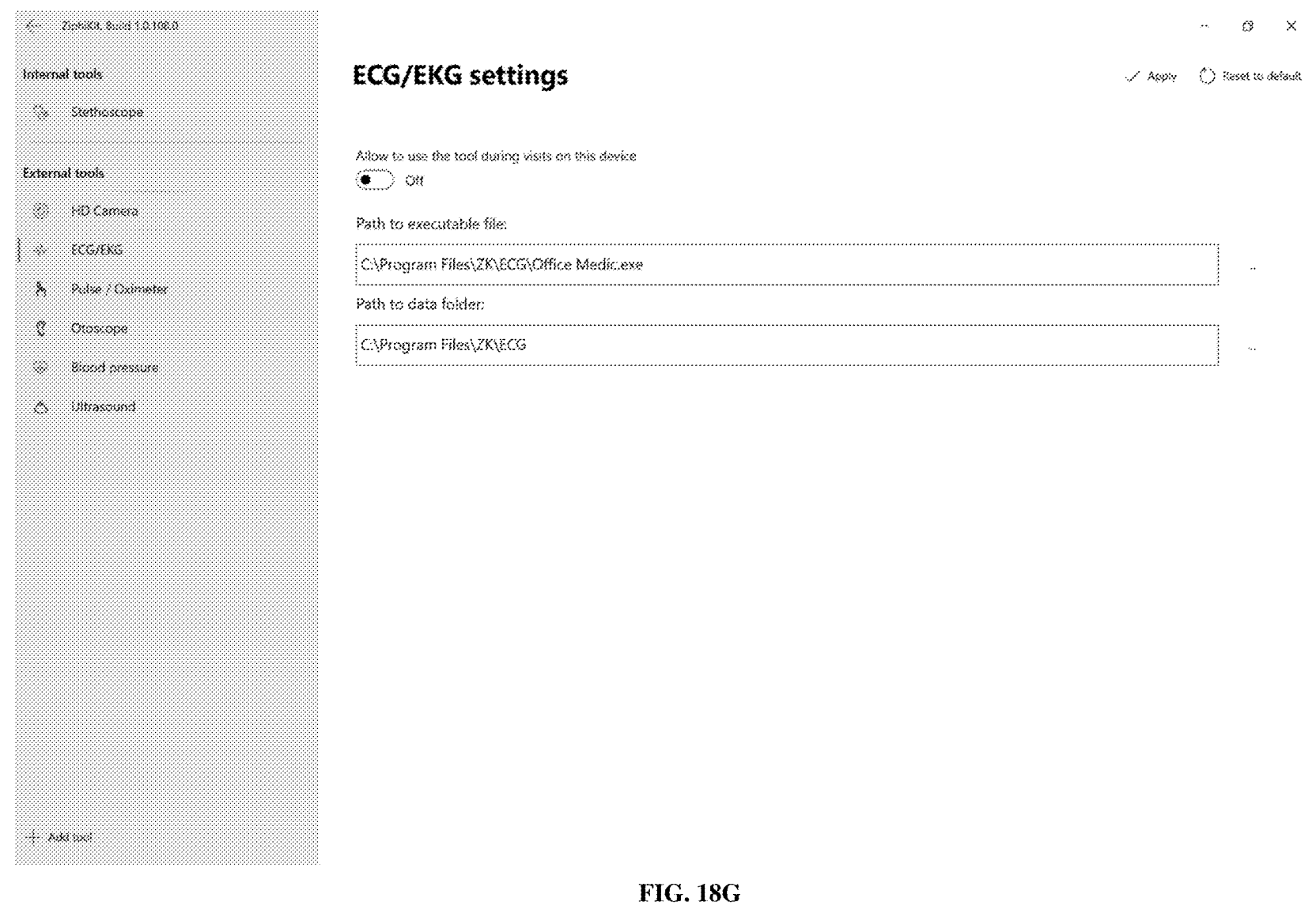

ECG/EKG settings

Allow to use the tool during visits on this device

○ Off

Path to executable file:

C:\Program Files\ZK\ECG\Office Medic.exe

Path to data folder:

C:\Program Files\ZK\ECG

Apply    ○ Reset to default

ZoomBox, Build 1.0.100.0

Internal tools
  Stethoscope

External tools
  HD Camera
  ECG/EKG
  Pulse / Oximeter
  Otoscope
  Blood pressure
  Ultrasound Add tool

FIG. 18G

Exams

Regular Exam     Health Checkup     Chronic Condition Follow Up

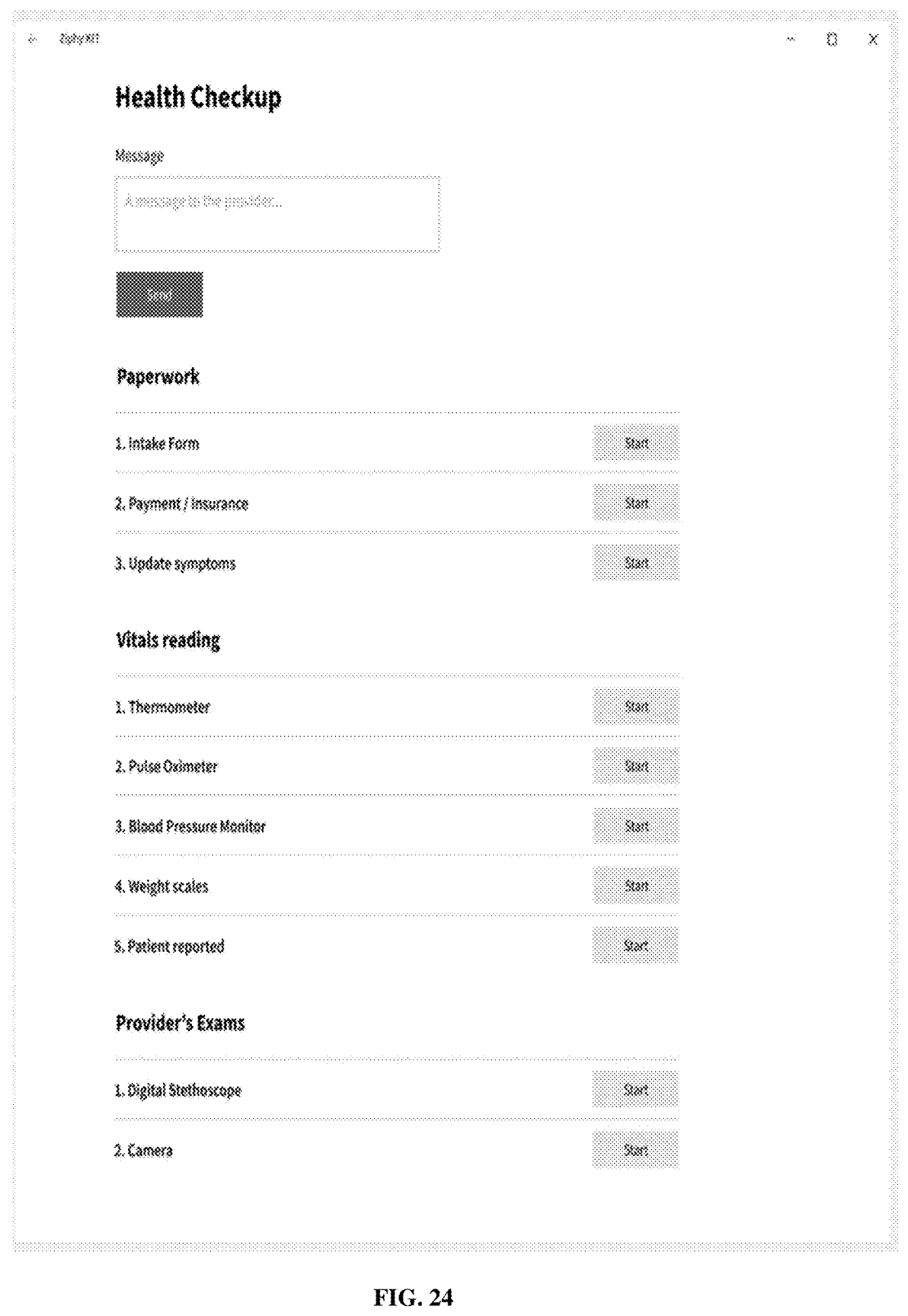

Health Checkup

Message

A message to the provider...

[send]

Paperwork

1. Intake Form | Start

2. Payment / Insurance | Start

3. Update symptoms | Start

Vitals reading

1. Thermometer | Start

2. Pulse Oximeter | Start

3. Blood Pressure Monitor | Start

4. Weight scales | Start

5. Patient reported | Start

Provider's Exams

1. Digital Stethoscope | Start

2. Camera | Start

FIG. 24

Instruments

Thermometer        Pulse Oximeter        Blood Pressure        Weight scales
                                              Monitor Stethoscope        Camera

MEDICAL DIAGNOSTIC KIT

CROSS-REFERENCE TO RELATED APPLICATIONS

This application claims priority to and the benefit of the provisional patent application titled "Medical Diagnostic Kit", application No. 63/121,302, filed in the United States Patent and Trademark Office (USPTO) on Dec. 4, 2020, and the provisional patent application titled "Industrial Camera Unit (ICU) for Performing Ear, Nose, Throat (ENT) And Skin Imaging", application No. 63/120,800, filed in the USPTO on Dec. 3, 2020. The specifications of the above referenced patent applications are incorporated herein by reference in their entirety.

BACKGROUND

Recent advancements in deployment and development of digital and telecommunication technologies have led to an emerging use of telemedicine. Telemedicine utilizes a combination of digital and telecommunication technologies and devices, for example, medical instruments, computers, wireless devices such as mobile phones, smartphones, satellite communication devices, audio/video devices, online management systems, smartphone applications, secure communication and storage protocols, etc., for analysing a patient's clinical health status and assisting in diagnosing and treating the patient. The purpose of telemedicine is to improve a patient's health by enabling a secure, interactive, two-way, real-time communication between the patient or a health care professional, for example, an onsite care coordinator (OCC) attending to the patient at the patient's location and a health care practitioner, for example, a physician, at a remote site. Telemedicine allows health care practitioners such as physicians to use telehealth appointments to pre-screen patients for possible infectious disease, and reduces exposure of patients, especially those who are chronically ill, pregnant, elderly, or immunocompromised, to other people's germs by avoiding physical visits of the patient to a physician's office. Telemedicine allows patients with infectious diseases such as the coronavirus disease (COVID)-19 to be diagnosed at their home locations, thereby reducing the spread of germs and viruses into a community. Additional benefits that have fed the need for telemedicine include, for example, better availability and access to health care providers and health care services, lower health care costs, increased efficiency and revenue, time savings, etc.

Telemedicine is increasingly being used to close health care gaps over a large geographic area, address underutilized physician availability at any location, and attend to under-served patient populations due to scarcity of geographically local physicians. For example, during the COVID-19 pandemic, mandatory social distancing has made telemedicine the safest interactive system between patients, both infected and uninfected, and health care practitioners. There is also a need for continued examination and treatment of non-COVID-19-related illnesses, particularly among vulnerable patient populations such as the elderly or immunocompromised, who would otherwise avoid or defer care as a result of self-isolation during the COVID-19 pandemic. Telemedicine allows physicians who are temporarily barred from delivering in-person care due to the need to self-quarantine following COVID-19 exposure or infection, to provide continuous services.

While telemedicine is expected to grow rapidly over the next decade due to its multiple benefits, telemedicine still poses several technical and practical problems for health care practitioners. Health care continuity typically suffers in cases where patients use on-demand telemedicine services that connect them to a health care practitioner. A patient's primary care practitioner may not have access to records generated from multiple virtual visits to different health care practitioners and therefore, have to perform a diagnosis with an incomplete medical history of the patient. Another challenge is the unreliable and interruptive access to a wireless communication network at the patient's location, causing delays and inaccuracies in performing a comprehensive medical examination of the patient. In addition to obtaining reliable and continuous access to a wireless communication network for communicating with a remote health care practitioner, the effectiveness of telemedicine depends on the effective use and management of medical instruments and digital technologies at the patient's location. There is a need for deploying appropriate tools, devices, equipment, and digital applications at a patient's location to aid a remote health care practitioner in performing a medical examination of the patient.

Some conventional solutions used in the practice of telemedicine include kits comprising medical instruments used for examining a patient at the patient's location by a health care professional, for example, an onsite care coordinator (OCC). Conventional kits generally do not provide adequate placement and arrangement of medical instruments, which results in disorderly management of the medical instruments and their cables during the medical examination, entanglement of the cables, confusion, and loss of productivity to a health care professional, for example, a nurse practitioner or another OCC, attending to the patient at the patient's location along with a physician at a remote site. The inadequate arrangement also makes the medical instruments difficult to access during a medical examination. Moreover, multiple connected medical instruments with universal serial bus (USB) interfaces consume power during a medical examination, which is not a problem when the medical instruments are connected to a powerful personal computer (PC) running from an alternating current (AC) outlet in the physician's office, but is a problem for a portable autonomous device running on a battery in the field. Accordingly, there is a need for a kit that facilitates secure and fast charging of the connected medical instruments. Furthermore, conventional kits do not have provisions for accommodating medical instruments of different types and configurations, their cables, and future variants therewithin. Furthermore, conventional kits require each medical instrument to be charged separately, mostly external to the kit, which takes a significant amount of time and management effort when there are multiple medical instruments in the kit.

Some conventional kits comprise a multi-layer stowage area for the medical instruments, where the medical instrument must be manually and sequentially plugged into an external universal serial bus (USB) hub using a specific USB cable for powering the medical instrument, and detached each time. Moreover, there is a need for saving battery power of a USB hub in the kit when the medical instruments are not in use. Another challenge during a remote medical examination is the inability of a remote health care practitioner to view a patient lying on a bed at the patient's location. The remote health care practitioner may not be able to view the patient lying on the bed as the patient may not be in the field of view of a camera being used for video-conferencing during the remote medical examination, as the camera is commonly, permanently attached to a top lid of the kit. Furthermore, conventional kits do not include complementary broadband communication devices and handheld computing devices, for example, tablet computing devices, organized therewithin that adequately facilitate remote real-time medical examinations, provide access to a reliable communication network, operate with the medical instruments for enhanced visualization of organs of the patient, and receive, generate, process, store, and securely transmit medical data during the medical examination for future use, diagnosis, and continuous follow-up.

Hence, there is a long-felt need for a medical diagnostic kit for facilitating telemedicine, that is, a remote medical examination of a patient by approximating a physician-present exam more closely, by allowing health care practitioners not only to see and hear the patient remotely, but also to conduct in-depth screenings and medical exams using hospital-grade, diagnostic equipment deployed by trained health care professionals, for example, onsite care coordinators, acting as the "physician's hands" at the patient's location, while addressing the above-recited problems associated with the related art.

SUMMARY

This summary is provided to introduce a selection of concepts in a simplified form that are further disclosed in the detailed description. This summary is not intended to determine the scope of the claimed subject matter.

The apparatus disclosed herein addresses the above-recited need for a medical diagnostic kit for facilitating telemedicine, that is, a remote medical examination of a patient by approximating a physician-present exam more closely, by allowing health care practitioners not only to see and hear the patient remotely, but also to conduct in-depth screenings and medical exams using hospital-grade, diagnostic equipment deployed by trained health care professionals, for example, onsite care coordinators (OCCs) acting as the "physician's hands" at the patient's location, when a communication network, for example, a broadband communication network, is available. If a communication link to the physician's remote computing device is not available, the medical diagnostic kit is configured to store medical data, for example, the patient's vital signs, sonograms, electrocardiograms (ECGs), auscultation sounds, camera images, etc., securely in an internal storage device for a later upload or an artificial intelligence (AI)-enabled batch upload to the physician's remote computing device, when the communication network is available. The medical diagnostic kit comprises hospital-grade, United States Food and Drug Administration (FDA) approved diagnostic equipment.

The medical diagnostic kit disclosed herein comprises a casing, a universal cable storage compartment, a deck, multi-port hubs, one or more energy storage devices, a hubs disconnection switch, and one or more computing devices. The casing comprises an upper shell, that is, a top lid, and a lower shell connected to each other via a hinged connection. The upper shell is in movable relation to the lower shell via the hinged connection between an open position and a closed position of the casing. The upper shell of the casing comprises an upper support wall adjoined by side walls oriented substantially perpendicular to the upper support wall to define an upper cavity. The lower shell of the casing comprises a lower support wall adjoined by side walls oriented substantially perpendicular to the lower support wall to define a lower cavity.

The universal cable storage compartment is accommodated in the casing. In an embodiment, the universal cable storage compartment is accommodated in the lower cavity of the lower shell of the casing. The universal cable storage compartment comprises movable dividers and subdividers configured to create configurable cable compartments for accommodating cables of multiple clinical examination devices without mutual entanglement. The cables are, for example, power supply and data communication or exchange cables such as universal serial bus (USB) cables. The clinical examination devices are medical instruments comprising, for example, an auscultation device such as a stethoscope, an electrocardiograph (ECG), an otoscope, an ultrasound device, a thermometer, a blood pressure monitor, an oximeter, a throat exam camera, a skin exam camera, a secondary camera, etc. The deck is positioned on the universal cable storage compartment. In an embodiment, the deck is accommodated in the lower cavity of the lower shell of the casing. The deck supports the clinical examination devices and accessories in the casing. The deck comprises multiple cutouts, that is, openings positioned in a one-to-one correspondence to the configurable cable compartments of the universal cable storage compartment. The cutouts of the deck are configured to support the clinical examination devices and accessories in multiple configurations. The cutouts of the deck extend or open into the universal cable storage compartment for cable management. The accessories comprise, for example, one or more input devices and one or more output devices configured to interface with one or more of the computing devices; ECG electrodes; etc. The input devices comprise, for example, a headset with a microphone, a wireless keyboard, etc. The output device(s) comprises, for example, a wireless speaker.

In an embodiment, the medical diagnostic kit further comprises air circulation holes configured proximal to an edge of the deck. The air circulation holes are configured to assist in movement of forced air provided by an air-cooling fan system, during charging of the computing devices, the clinical examination devices, the accessories, and other devices accommodated in the upper cavity of the upper shell of the casing, powered by the multi-port charger. The air circulation holes allow movement of forced air from the lower cavity defined by the lower shell of the casing to the upper cavity defined by the upper shell of the casing. In an embodiment, the medical diagnostic kit further comprises a cushioning member, for example, a foam block, comprising slots positioned on the deck in correspondence to the configurable cable compartments of the universal cable storage compartment. The slots of the cushioning member are configured according to shapes of the clinical examination devices and the accessories to protectively accommodate the clinical examination devices and the accessories in multiple configurations during transportation and deployment of the medical diagnostic kit. The shapes of the slots of the cushioning member protectively accommodate clinical examination devices and accessories of different shapes and sizes.

The multi-port hubs are positioned, for example, in a console positioned inside the casing. In an embodiment, the multi-port hubs are accommodated in the lower cavity of the lower shell of the casing. In an embodiment, the console is attached to a side wall inside the casing. For example, the console is attached to one of the side walls of the lower shell of the casing. In another embodiment, the console is attached to the deck. The multi-port hubs, for example, universal serial bus (USB) hubs, are configured to permanently and securely connect individual cable connectors of the clinical examination devices and the accessories and selectively power up and communicate data with one or more of the clinical examination devices and the accessories, while the cables of the clinical examination devices and the accessories are accommodated in the cable compartments or holders of the universal cable storage compartment. In an embodiment, each of the multi-port hubs comprises multiple USB switchable ports configured to permanently and securely connect the individual cable connectors of the clinical examination devices and the accessories and selectively power and communicate data with one or more of the clinical examination devices and the accessories engaged in a particular medical examination. The energy storage device(s) feeds or powers the multi-port hubs comprising switchable ports to which the individual cable connectors of the clinical examination devices and the accessories are connected. The multi-port hubs receive the power from the energy storage device(s) and deliver the power to the clinical examination devices and the accessories that are activated via the switchable ports of the multi-port hubs to which the clinical examination devices and the accessories are connected. The individual cable connectors of the clinical examination devices and the accessories extend from their respective cables accommodated in the universal cable storage compartment below the deck. The individual cable connectors of the clinical examination devices and the accessories are permanently and securely connected to the switchable ports of the multi-port hubs, while the respective cables are tied down to the cable compartments or holders proximal to the switchable ports.

In an embodiment, the medical diagnostic kit further comprises a headset jack positioned at a predetermined mounting location in the casing. For example, the headset jack is operably coupled in the console or on another mounting device in the casing. The headset jack is configured to connect a headset for use during auscultation. In another embodiment, the medical diagnostic kit further comprises an auxiliary port positioned at a predetermined mounting location in the casing. The auxiliary port is configured to facilitate external connections to one of the multi-port hubs. For example, in an embodiment, the auxiliary port is operably coupled in the console for facilitating external connections to one of the multi-port hubs. In another embodiment, the auxiliary port is operably coupled to the deck proximal to the patient undergoing a remote medical examination. The auxiliary port is operably coupled to a switchable port of one of the multi-port hubs for delivering power to the external connections and executing data exchange with the external connections. In an embodiment, the medical diagnostic kit further comprises illuminating control elements operably coupled to the switchable ports of the multi-port hubs. The illuminating control elements are positioned, for example, on the console. The illuminating control elements, for example, illuminating switches, are configured to activate or deactivate one or more of the clinical examination devices and one or more of the accessories engaged in a particular medical examination to save battery power and provide visual information to a health care professional, for example, an onsite care coordinator (OCC) about the switchable ports being energized.

One or more energy storage devices are operably coupled to a multi-port charger inside the casing. In an embodiment, the energy storage device(s) and the multi-port charger are accommodated in the lower cavity of the lower shell of the casing. A power distribution board operably coupled to the multi-port charger is also accommodated in the lower cavity of the lower shell of the casing. The multi-port charger is electrically connected to and configured to charge the energy storage device(s), the computing devices, the clinical examination devices, and the accessories during a charging operation. In an embodiment, the energy storage device(s) is operably coupled to external power inputs of the multi-port hubs. The energy storage device(s), when connected to a power source, for example, an alternating current (AC) power source, is configured to receive power from the multi-port charger. The energy storage device(s) delivers the power to the multi-port hubs via the hubs disconnection switch for powering and communicating data with the clinical examination devices when the casing is in the open position. In an embodiment, the medical diagnostic kit further comprises a primary hub operably coupled to the multi-port charger. The primary hub is also operably coupled to one of the computing devices, for example, the diagnostic computer, for delivering power to the diagnostic computer for charging the diagnostic computer. In addition to the diagnostic computer, the primary hub is also operably coupled to the multi-port hubs for data communication with the diagnostic computer. The primary hub is configured to receive power from the multi-port charger and deliver the power to the diagnostic computer for charging the diagnostic computer and executing data communication between the diagnostic computer and the clinical data examination devices and the accessories.

The hubs disconnection switch is operably coupled to the energy storage device(s) and the multi-port hubs. In an embodiment, a hubs disconnection switch board is accommodated in the lower cavity of the lower shell of the casing. The hubs disconnection switch is in operable communication with a disconnection member operably connected between the upper shell and the lower shell of the casing. The disconnection member is, for example, a magnet or a lever, in operable communication with the hubs disconnection switch. The hubs disconnection switch, when activated by the disconnection member, is configured to interrupt the delivery of the power from the energy storage device(s) to the multi-port hubs when the casing is in the closed position.

The computing devices are supportably positioned in the casing. In an embodiment, the computing devices are supportably positioned in the upper cavity of the upper shell of the casing. At least one of the computing devices is configured with a wide bandwidth data transmission capability, for example, a broadband capability. In an embodiment, one of the computing devices is a diagnostic computer. The diagnostic computer is configured to (a) activate one or more of the clinical examination devices; (b) execute media conference connections; (c) receive, create, record, process, store, and securely transmit medical data from the clinical examination device(s) to a data store or a data storage device via a communication network, for example, a wireless communication network; and (d) facilitate remote real-time medical examinations via a software application deployed on the diagnostic computer. In an embodiment, another one of the computing devices is a communication device in operable communication with the diagnostic computer via the communication network. The communication device is configured to display a media stream, for example, a video stream, from one or more of the clinical examination devices. In an embodiment, the communication device is configured to remotely control the software application deployed on the diagnostic computer. In an embodiment, the communication device is a tablet computing device comprising a display unit configured to assist in aiming a camera lens of one of the clinical examination devices and visualizing one or more of multiple organs, for example, eyes, nose, throat, skin, etc., of a patient. The display unit is configured to receive and display a media stream of each of the visualized organs captured by the clinical examination device(s) via the camera lens. In an embodiment, the software application is configured to display, on the diagnostic computer, a panel of the clinical examination devices and the accessories accommodated in the medical diagnostic kit and indications of one or more of the clinical examination devices and the accessories on the panel suggested by a health care practitioner at a remote site for usage during the remote real-time medical examinations.

In an embodiment, the diagnostic computer is accommodated in a device holder pivotably connected to an upper support wall of the upper shell of the casing. The device holder is configured to assist in aiming of a camera of the diagnostic computer when pivoted. In an embodiment, the communication device is accommodated in a removable device holder lockably positioned in the casing, for example, in the upper cavity of the upper shell of the casing. In an embodiment, when unlocked and removed from the casing, the removable device holder assists in attaching the communication device to one or more of the clinical examination devices, for example, a throat or skin exam camera, etc. In an embodiment, the device holder is removable during use and configured to be locked in position in the casing using an attachment member, for example, a sliding attachment member, during transportation of the medical diagnostic kit. The removable device holder is configured to be unlocked and slid out from the attachment member for attachment to other clinical examination devices, for example, a throat or skin exam camera via a mechanical coupling such as a ball coupling. In an embodiment, the medical diagnostic kit further comprises a device holder positioned in the casing, for example, in the upper cavity of the upper shell of the casing, for accommodating another computing device, for example, a network-enabled mobile phone configured to provide access of the communication network to the diagnostic computer and the communication device. In an embodiment, the device holder that accommodates the network-enabled mobile phone is non-removable.

In an embodiment, the medical diagnostic kit further comprises a side door hinged to a door frame exteriorly positioned on a side wall of the casing. The side door is configured to close over a gasket and protect inlet ports and outlet ports of the medical diagnostic kit from dust, water, and other external elements. The inlet ports and the outlet ports are positioned on a side wall of the casing. In an embodiment, the inlet ports comprise an air intake port with a particle filter and an alternating current (AC) fused inlet. The AC fused inlet is configured to provide the power from the power source to the multi-port charger for charging the energy storage device(s), the computing devices, the clinical examination devices, and the accessories inside the casing. In an embodiment, the outlet ports comprise louvers in fluid communication with an air-cooling fan system positioned in the casing, for example, in the lower cavity of the lower shell of the casing. The louvers are configured to direct heated internal air in an upward direction into the upper cavity of the casing without mixing with incoming external air flowing in the lower cavity of the casing for cooling efficiency and optimal cooling in the medical diagnostic kit. In an embodiment, the medical diagnostic kit further comprises a fan protector affixed to the deck. The fan protector is configured to protect an exhaust fan of the air-cooling fan system interiorly positioned proximal to a side wall of the casing. The exhaust fan is supported by a fan backplate. The fan backplate is exteriorly positioned on the side wall of the casing. In an embodiment, the fan backplate is exteriorly positioned on the side wall of the lower shell of the casing.

In an embodiment, the air-cooling fan system comprises cooling fans, for example, the exhaust fan and an intake fan, positioned in the lower cavity and the upper cavity of the casing. The air-cooling fan system is configured to produce an air flow within the lower cavity and the upper cavity of the casing for cooling the multi-port charger, the energy storage device(s), the computing devices, the clinical examination devices, and the accessories to prevent overheating thereof when the casing is in the closed position during charging. In an embodiment, the medical diagnostic kit further comprises a secondary camera extending from a flexible mount, for example, a goose neck, in the casing. The secondary camera is operably coupled to one of the multi-port hubs using an internal power supply and data communication or exchange cable, for example, a USB cable, positioned in the flexible mount. The flexible mount with its internal USB cable is configured to aim a camera lens of the secondary camera towards a patient and allow a health care practitioner at a remote site to view the patient when the patient is out of view of a camera of the diagnostic computer. In an embodiment, the secondary camera is connected to the auxiliary port or placed in a holder or on the console.

In an embodiment, the medical diagnostic kit further comprises a stethoscope interface component operably coupled to one of the multi-port hubs via an audio card for executing a remote auscultation using a stethoscope. In an embodiment, the stethoscope interface component is accommodated in the lower cavity of the lower shell of the casing. In an embodiment, the stethoscope is accommodated in one of the cutouts on the deck, or in one of the slots of the cushioning member. The audio card is, for example, a universal serial bus (USB) sound card. The stethoscope is charged by the multi-port charger within the casing via the stethoscope interface component, without having to remove the stethoscope from the casing and connect to an external charger with a particular charging cable provided by a manufacturer. In an embodiment, the stethoscope interface component comprises an audio splitter, an audio switch, and a decoder. The audio splitter is operably coupled to the stethoscope for receiving a stethoscope signal from the stethoscope during the remote auscultation and splitting the stethoscope signal into a first audio signal and a second audio signal. The audio splitter transmits the first audio signal to the headset connected to the headset jack or the auxiliary port positioned at a predetermined mounting location, for example, on the console, in the casing. The audio splitter transmits the second audio signal to the audio card via the audio switch. The audio card is configured to transmit the second audio signal to the remote computing device of the remote health care practitioner via the diagnostic computer. The audio switch is configured to select between the second audio signal and a microphone signal from the headset for transmission to the audio card. The decoder is operably coupled to an audio control element or button of the headset. The decoder is configured to decode a control signal received from the audio control element of the headset and to operate the audio switch.

In an embodiment, the medical diagnostic kit implements a quick connect-disconnect mechanism with the clinical examination devices and the accessories for quick removal thereof from the medical diagnostic kit and quick stowage thereof into the medical diagnostic kit. In an embodiment, the medical diagnostic kit implements the quick connect-disconnect mechanism, for example, using a magnetic charging connector system. The magnetic charging connector system comprises one or more magnetic connectors operably coupled to the multi-port charger, for example, via the power distribution board. The magnetic connector(s) is magnetically engageable to one or more of the clinical examination devices and the accessories positioned proximal to the magnetic connector(s) to create an electrically conductive relationship therebetween. The magnetic connector(s) comprises mating elements, for example, a first magnetic connecting element and a second magnetic connecting element. The first magnetic connecting element protrudes from each of one or more of the cutouts of the deck. The second magnetic connecting element is operably coupled to a connector section of a battery of each of one or more of the clinical examination devices and the accessories. The second magnetic connecting element, when in close proximity to the first magnetic connecting element, is configured to magnetically attract the first magnetic connecting element for receiving the power delivered by the power distribution board from the multi-port charger. In this embodiment, the clinical examination devices and the accessories are connected to the multi-port charger for charging using the magnetic connectors that allow convenient disconnection when the clinical medical devices and the accessories are removed from the storage position in the deck, and allow convenient connection when the clinical medical devices and the accessories are returned for stowage in the deck.

The medical diagnostic kit allows the clinical examination devices to be connected to the built-in multi-port hubs at all times until maintenance and has one or more clinical examination devices with similar speed active at all times; allows charging of the internal components when the casing is in the closed position or the open position; adopts a top layer cushioning material or foam for various device configurations; allows storage of the cables of the clinical examination device below the deck separately in a coiled configuration; and provides an internal hotspot without relying on a customer's wireless communication network. The medical diagnostic kit in the closed position is configured to be transported without the internal energy storage device being discharged using the hubs disconnection switch, activated by the disconnection member, that disconnects the energy storage device when the casing is in a fully closed position. The medical diagnostic kit allows the clinical examination devices to be charged inside the casing without having to remove them from the casing and change their cables.

In one or more embodiments, related systems comprise circuitry and/or programming for executing the methods disclosed herein. The circuitry and/or programming are of any combination of hardware, software, and/or firmware configured to execute the methods disclosed herein depending upon the design choices of a system designer. In an embodiment, various structural elements are employed depending on the design choices of the system designer.

BRIEF DESCRIPTION OF THE DRAWINGS

The foregoing summary, as well as the following detailed description, is better understood when read in conjunction with the appended drawings. For illustrating the embodiments herein, exemplary constructions of the embodiments are shown in the drawings. However, the embodiments herein are not limited to the specific structures, components, and methods disclosed herein. The description of a structure, or a component, or a method step referenced by a numeral in a drawing is applicable to the description of that structure, component, or method step shown by that same numeral in any subsequent drawing herein.

FIG. 17 illustrates an appointment log created by the software application.

FIGS. 18A-18G illustrate configuration screens of the various clinical examination devices.

FIG. 24 illustrates a Graphical User Interface (GUI) rendered by the software application showing instructions issued remotely to an operator by the remote health care practitioner for a selected procedure.

DETAILED DESCRIPTION

Figure 1:
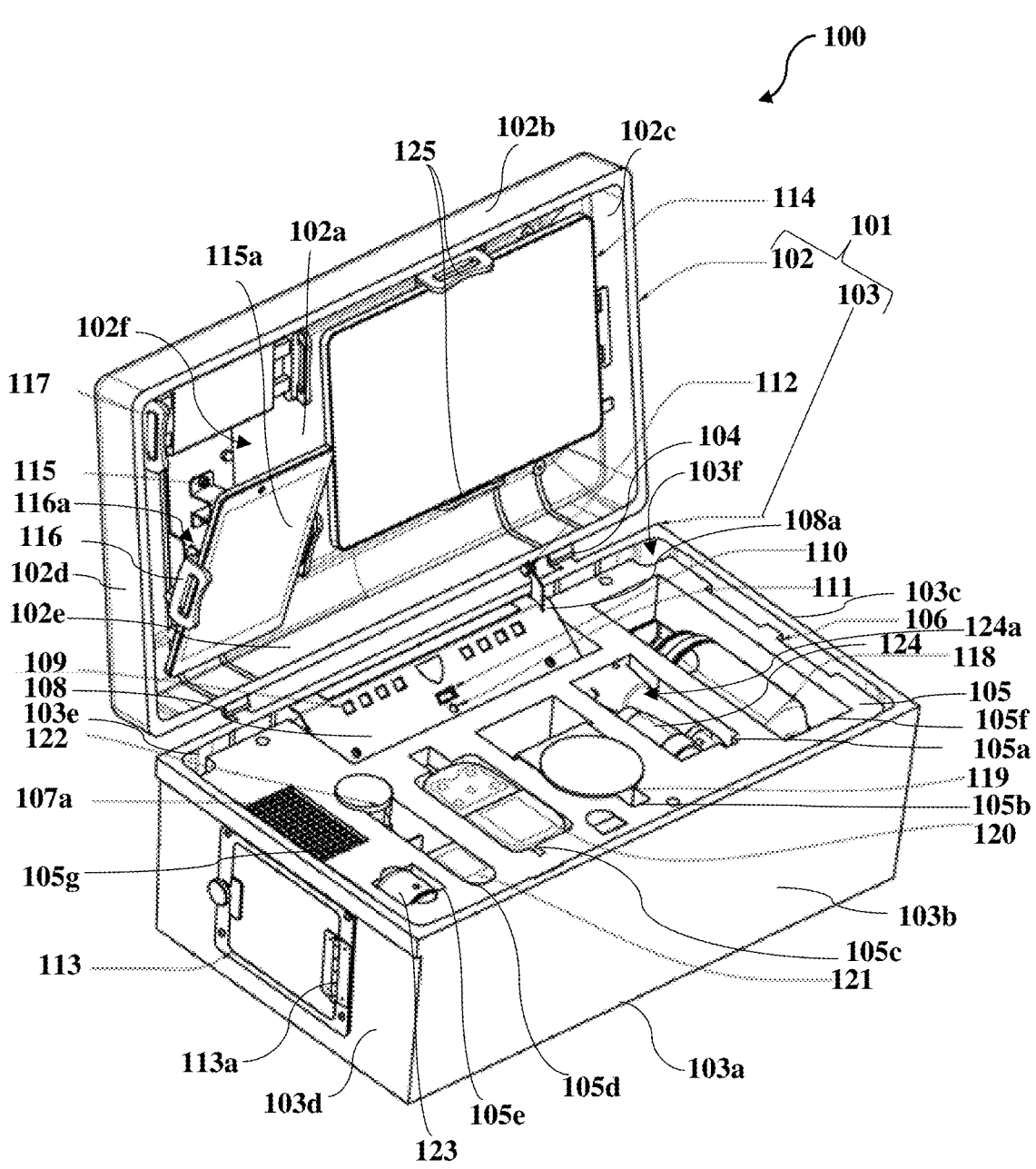
FIG. 1 exemplarily illustrates a top perspective view of an embodiment of a medical diagnostic kit.

FIG. 1 exemplarily illustrates a top perspective view of an embodiment of a medical diagnostic kit 100. The medical diagnostic kit 100 is configured for use as a clinical aid to provide vital signs and telemetered data to health care practitioners, health care professionals, and medical professionals. The medical diagnostic kit 100 provides tools for medical examinations comprising, for example, electrocardiograms, blood pressure, temperature, and visual examinations to be relayed by telemetry. In an embodiment, the medical diagnostic kit 100 provides a user-friendly, web-based platform with an integrated video/audio conference connection enabling remote, real-time medical examinations. Medical data recorded during the remote, real-time medical examinations is securely stored electronically for future diagnostic and/or therapeutic use. The tools provided by the medical diagnostic kit 100 comprise, for example, clinical examination devices and accessories for remote and in-home use. The clinical examination devices are medical instruments comprising, for example, an auscultation device or a stethoscope 122 such as a digital stethoscope of Thinklabs Medical LLC, an electrocardiograph (ECG) 119 such as the Universal ECG® of QRS Diagnostic, LLC, an otoscope 124 such as the Welch Allyn® otoscope of Welch Allyn, Inc., an ultrasound device (not shown), a thermometer (not shown), a blood pressure monitor 120 such as the ABPM50 ambulatory blood pressure monitor of Contec Medical Systems USA, Inc., an oximeter 121 such as the CMS50DL pulse oximeter of Contec Medical Systems USA, Inc., a secondary camera 147 exemplarily illustrated in FIGS. 7A-7B, a multi-organ imaging system 118 configured, for example, as a throat exam camera, a skin exam camera, etc.

In an embodiment, the medical diagnostic kit 100 is configured for use by trained health care professionals for remote and in-home medical examination of patients. The medical diagnostic kit 100 is configured to be set up in a clean environment and on a firm flat surface. The medical diagnostic kit 100 allows a secure, interactive, two-way, real-time communication between a patient or an operator of the medical diagnostic kit 100 attending to the patient at the patient's location and a health care practitioner, for example, a physician, at a remote site. The operator of the medical diagnostic kit 100 is, for example, a trained, onsite care coordinator (OCC), a nurse, or a technician who acts as the "physician's hands" at the patient's location to conduct in-depth screenings and medical examinations using hospital-grade, United States Food and Drug Administration (FDA) approved diagnostic equipment deployed in the medical diagnostic kit 100. The OCCs are, for example, medical assistants or nurses who act as exam facilitators and the "physician's hands" at the patient site, employing the clinical examination devices from the medical diagnostic kit 100 under continual, real-time audio/video observation and direction by a remotely-connected physician. The medical diagnostic kit 100 facilitates a two-way continuous conversation between a patient or the OCC and a physician, where the physician sees the patient, the physician sees the OCC, and the physician sees the telemetry of the clinical examination devices and can remotely conduct the medical examination, if needed.

Figure 2:
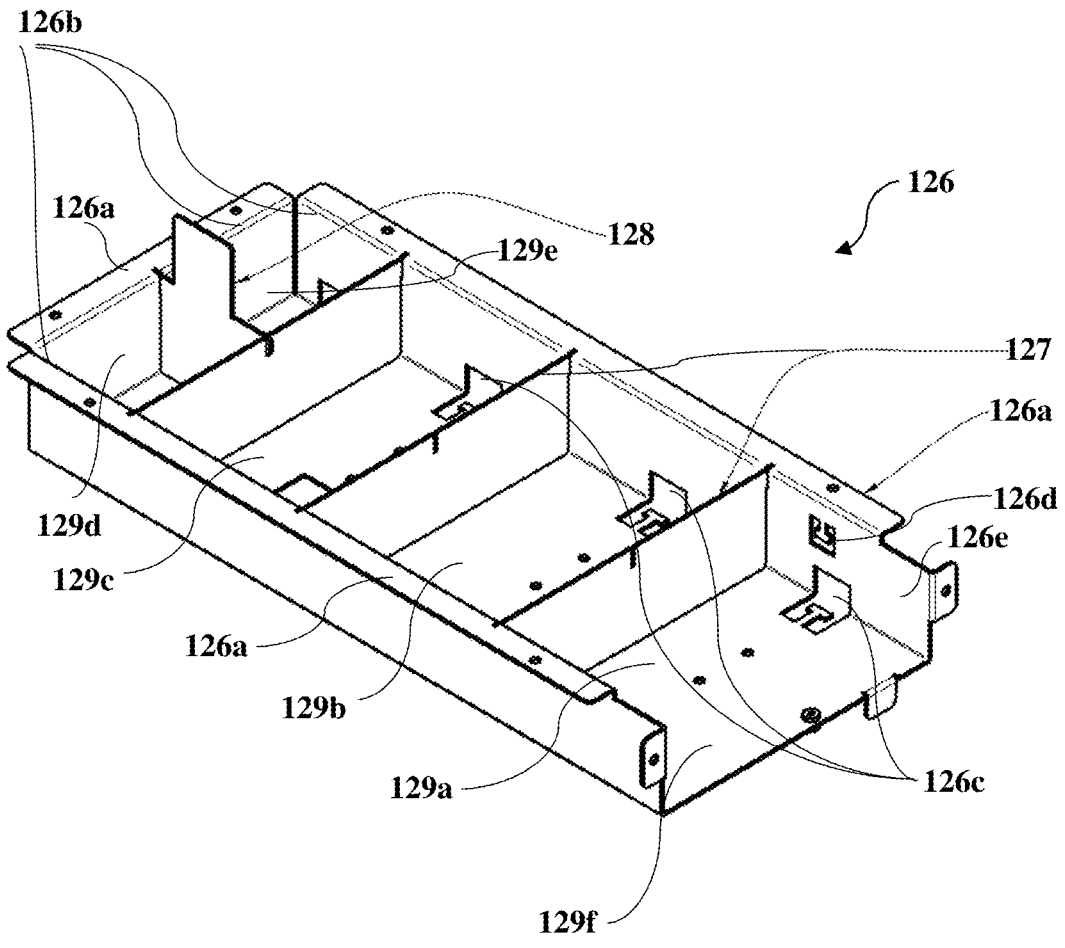
FIG. 2 exemplarily illustrates a perspective view of an embodiment of a universal cable storage compartment of the medical diagnostic kit.
Figure 3:
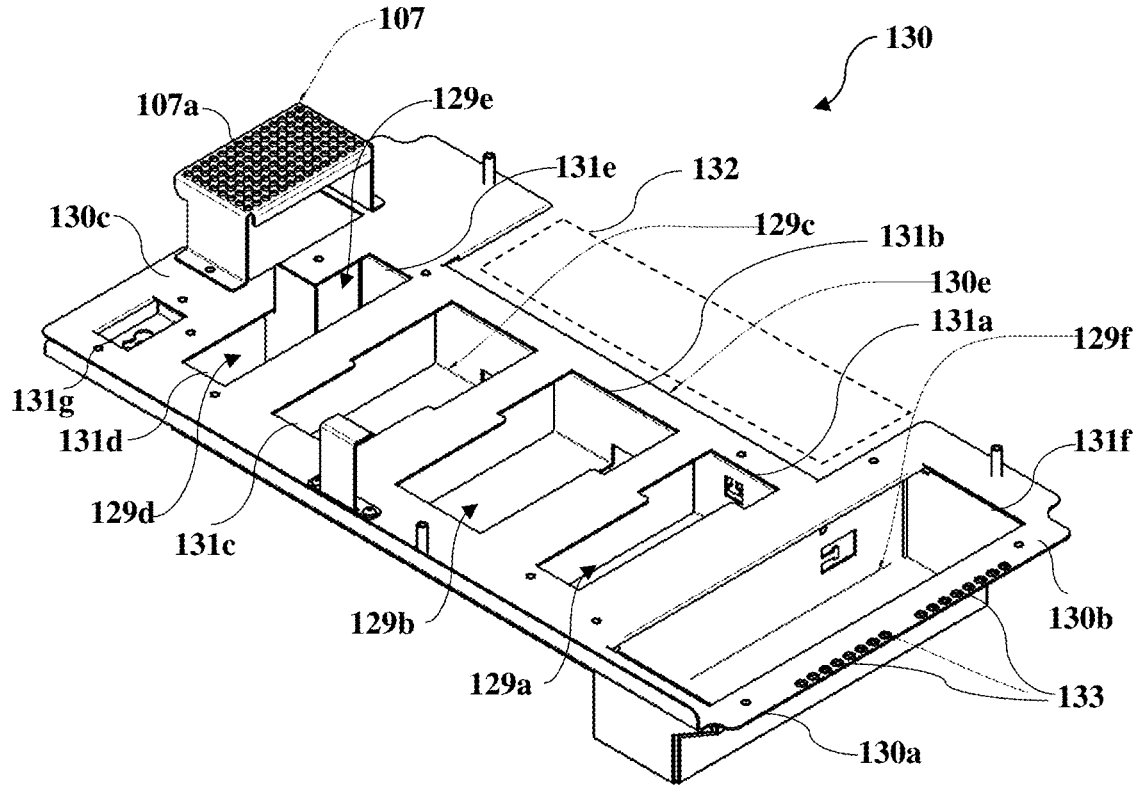
FIG. 3 exemplarily illustrates a perspective view of an embodiment of a deck of the medical diagnostic kit.
Figure 6A:
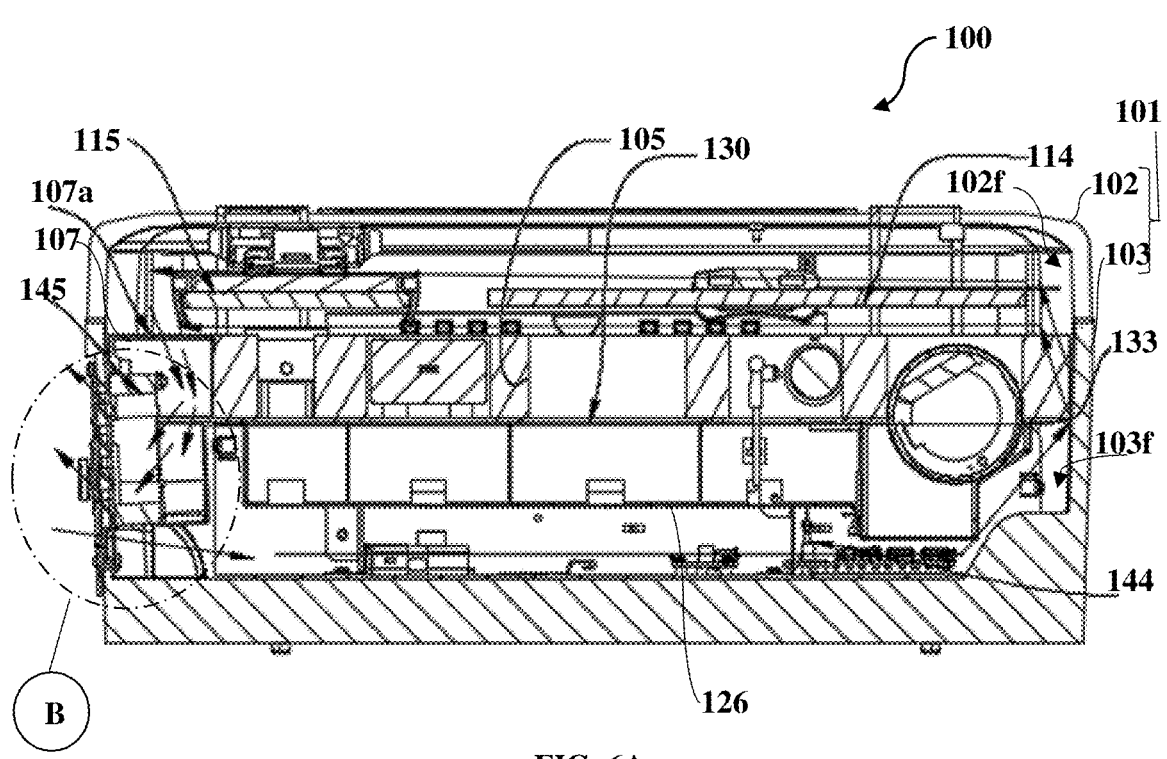
FIG. 6A exemplarily illustrates a cross-sectional view of an embodiment of the medical diagnostic kit taken along a section A-A shown in FIG. 5.
Figure 8:
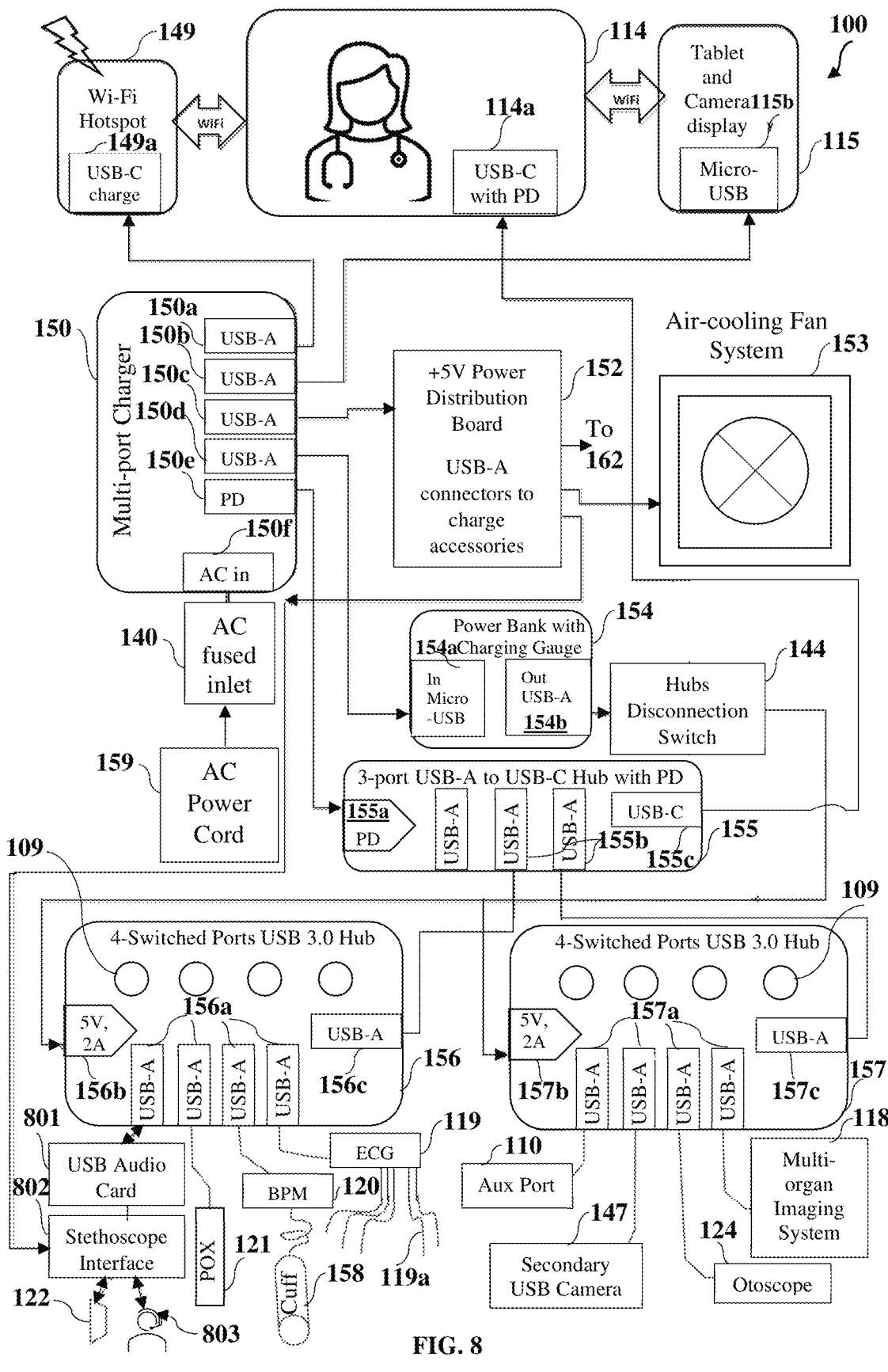
FIG. 8 illustrates a block diagram showing an exemplary implementation of internal components of an embodiment of the medical diagnostic kit.

The medical diagnostic kit 100 disclosed herein comprises a casing 101, a universal cable storage compartment 126 exemplarily illustrated in FIG. 2, a deck 130 exemplarily illustrated in FIG. 3, a cushioning member 105, a console 108, one or more energy storage devices, for example, a power bank 154 with a charging gauge exemplarily illustrated in FIG. 8, a hubs disconnection switch 144 exemplarily illustrated in FIG. 6A and FIG. 8, a disconnection member 112, and one or more computing devices 114, 115, and 149 exemplarily illustrated in FIG. 8. At least one of the computing devices 114, 115, and 149 is configured with a wide bandwidth data transmission capability, for example, a broadband capability. The casing 101 comprises an upper shell 102, that is, a top lid, and a lower shell 103 connected to each other via a hinged connection constituted by one or more hinges 104. In an embodiment as exemplarily illustrated in FIG. 1, two, spaced apart hinges 104 are connected between the upper shell 102 and the lower shell 103 of the casing 101 for configuring the casing 101 in an open position and a closed position. As used herein, the "open position" of the casing 101 refers to a condition of the casing 101 where the upper shell 102 is detached from the lower shell 103 and opened to expose the contents of the medical diagnostic kit 100. Also, as used herein, the "closed position" of the casing 101 refers to a condition of the casing 101 where the upper shell 102 is folded over the lower shell 103 and detachably attached to the lower shell 103 to enclose and cover the contents of the medical diagnostic kit 100. The upper shell 102 is in movable relation to the lower shell 103 via the hinges 104 between the open position and the closed position of the casing 101. As exemplarily illustrated in FIG. 1, the upper shell 102 is a lid configured to open and close the casing 101.

In an embodiment, the medical diagnostic kit 100 comprises a latch (not shown) for securing the upper shell 102 to the lower shell 103 of the casing 101. In an embodiment, the medical diagnostic kit 100 comprises a padlock with a key (not shown) for locking the upper shell 102 to the lower shell 103 of the casing 101. In another embodiment, the padlock is a numeric padlock requiring a numerical combination to open the padlock, and in turn, the casing 101. The upper shell 102 of the casing 101 comprises an upper support wall 102a adjoined by side walls 102b, 102c, 102d, and 102e oriented substantially perpendicular to the upper support wall 102a to define an upper cavity 102f. The lower shell 103 of the casing 101 comprises a lower support wall 103a adjoined by side walls 103b, 103c, 103d, and 103e oriented substantially perpendicular to the lower support wall 103a to define a lower cavity 103f. In an embodiment as exemplarily illustrated in FIG. 1, the upper shell 102 and the lower shell 103 are shaped similar to an open rectangular cuboid. The upper shell 102 and the lower shell 103 define an inner volume in the upper cavity 102f and the lower cavity 103f respectively, for accommodating the contents of the medical diagnostic kit 100. The upper shell 102 and the lower shell 103 are made, for example, of impact-resistant, light plastic materials.

The universal cable storage compartment 126 exemplarily illustrated in FIG. 2 and the deck 130 exemplarily illustrated in FIG. 3 are accommodated in the casing 101. In an embodiment, the deck 130 is accommodated over the universal cable storage compartment 126 in the lower cavity 103f of the lower shell 103 of the casing 101 as exemplarily illustrated in FIG. 6A. The structure and the function of the universal cable storage compartment 126 and the deck 130 are disclosed in the detailed descriptions of FIG. 2 and FIG. 3 respectively. The cushioning member 105 is made, for example, from closed cell foam sheets of polyethylene (PE) #2 and #4 glued together. The cushioning member 105, for example, a foam block, comprises slots 105a, 105b, 105c, 105d, and 105f positioned on the deck 130 in correspondence to cutouts, that is, openings 131a, 131b, 131c, 131d, 131e, and 131f of the deck 130 and cable compartments 129a, 129b, 129c, 129d, 129e, and 129f of the universal cable storage compartment 126 exemplarily illustrated in FIGS. 2-3. For example, the slots 105a, 105b, and 105c of the cushioning member 105 correspond to the cutouts 131a, 131b, and 131c of the deck 130 and the cable compartments 129a, 129b, and 129c of the universal cable storage compartment 126 respectively, while the slot 105d of the cushioning member 105 corresponds to the cutouts 131d and 131e of the deck 130 and the cable compartments 129d and 129e of the universal cable storage compartment 126. The slot 105e of the cushioning member 105 corresponds to the cutout 131g of the deck 130 exemplarily illustrated in FIG. 3. The slot 105f of the cushioning member 105 corresponds to the cutout 131f of the deck 130 and the cable compartment 129f of the universal cable storage compartment 126 exemplarily illustrated in FIG. 3. The slots 105a, 105b, 105c, 105d, 105e, and 105f of the cushioning member 105 are configured according to shapes of the clinical examination devices and the accessories to protectively accommodate the clinical examination devices and the accessories in multiple configurations during transportation and deployment of the medical diagnostic kit 100.

The accessories comprise, for example, one or more input devices and one or more output devices configured to interface with one or more of the computing devices 114 and 115; ECG electrodes 119a exemplarily illustrated in FIG. 8; etc. One or more input devices comprise, for example, a headset 803 with a microphone exemplarily illustrated in FIGS. 8-9, a secondary camera 147 exemplarily illustrated in FIGS. 7A-7B, and a wireless keyboard. The wireless keyboard is, for example, a Bluetooth®-enabled keyboard (not shown) with a touchpad mouse configured to interface with the computing devices 114, 115, and 149 exemplarily illustrated in FIG. 8. The output device(s) comprises, for example, a wireless speaker 123. In an embodiment, the slot 105e of the cushioning member 105 protectively accommodates the wireless speaker 123, for example, a Bluetooth® speaker of Bluetooth Sig, Inc. The wireless speaker 123 is paired with one of the computing devices, for example, a diagnostic computer 114 to output voice from the diagnostic computer 114. The removable, wireless speaker 123 is provided, for example, for hearing-impaired patients. The wireless speaker 123 receives digital audio streams wirelessly from the diagnostic computer 114, for example, via a Bluetooth® communication protocol, and decompresses, decodes, and amplifies the audio for facilitating communication between a remote health care practitioner and a hearing-impaired patient who cannot hear regular speakers provided in the diagnostic computer 114. The wireless speaker 123 is positioned near the patient's ears to allow the patient to hear the remote health care practitioner's voice better. The wireless speaker 123 and the headset 803 allow two-way communication between an operator of the medical diagnostic kit 100, the patient, and the remote health care practitioner. In an embodiment, the accessories further comprise batteries of one or more of the clinical examination devices, for example, an illuminator battery 124a of the otoscope 124 herein referred to as an otoscope illuminator battery 124a.

In an embodiment, the clinical examination devices and the accessories are accommodated on an upper surface 130c of the deck 130 in the cutouts 131a, 131b, 131c, 131d, 131e, and 131f of the deck 130 exemplarily illustrated in FIG. 3, with the cushioning member 105 having a specific thickness to level the clinical examination devices and the accessories on the upper surface 130c of the deck 130. In another embodiment, the clinical examination devices and the accessories are accommodated directly on the upper surface 130c of the deck 130 in the cutouts 131a, 131b, 131c, 131d, 131e, and 131f of the deck 130 as disclosed in the detailed description of FIG. 3. In an embodiment, the cushioning member 105 comprises airflow channels 106 configured to connect and provide fluid communication between the lower cavity 103f of the lower shell 103 of the casing 101 and the upper cavity 102f of the upper shell 102 of the casing 101. The airflow channels 106 in the cushioning member 105 are in fluid communication with the lower cavity 103f and the upper cavity 102f for circulating air between the lower cavity 103f and the upper cavity 102f of the casing 101. In an embodiment, the airflow channels 106 are in fluid communication with air circulation holes 133 configured proximal to an edge 130a of the deck 130 as exemplarily illustrated in FIG. 3. The air circulation holes 133 are configured to assist in movement of forced air provided by an air-cooling fan system 153 exemplarily illustrated in FIG. 6A and FIG. 8, during charging of the computing devices 114, 115, and 149, the clinical examination devices, the accessories, and other devices accommodated in the upper cavity 102f of the upper shell 102 of the casing 101, powered by a multi-port charger 150 exemplarily illustrated in FIG. 8. The air circulation holes 133 allow transfer and movement of the forced air from the lower cavity 103f to the upper cavity 102f of the casing 101.

The console 108 is positioned inside the casing 101. In an embodiment, the console 108 is attached to one of the side walls 103b, 103c, 103d, and 103e inside the casing 101. For example, the console 108 is attached to the side wall 103e of the lower shell 103 of the casing 101 as exemplarily illustrated in FIG. 1. In another embodiment, the console 108 is attached to the deck 130. The console 108 comprises multi-port hubs 156 and 157, for example, universal serial bus (USB) hubs exemplarily illustrated in FIG. 8, configured to permanently and securely connect individual cable connectors, for example, USB connectors, of the clinical examination devices and the accessories, and selectively power and communicate data with one or more of the clinical examination devices and the accessories. The clinical examination devices and one or more of the accessories are securely and permanently connected to switchable ports 156a and 157a of the multi-port hubs 156 and 157 respectively, exemplarily illustrated in FIG. 8, via the individual cable connectors and respective cable ties. Each of the switchable ports 156a and 157a of the multi-port hubs 156 and 157 respectively, are configured to be switched on and off, for example, using illuminating control elements 109.

In an embodiment, the medical diagnostic kit 100 further comprises a headset jack 111 positioned at a predetermined mounting location in the casing 101. The headset jack 111 is configured to connect a headset 803 exemplarily illustrated in FIGS. 8-9, for use during auscultation. For example, the headset jack 111 is operably coupled in the console 108 as exemplarily illustrated in FIG. 1, or on another mounting device in the casing 101, for use with the headset 803 during auscultation. In another embodiment, the medical diagnostic kit 100 further comprises an auxiliary port 110, for example, a USB connector, positioned at a predetermined mounting location in the casing 101. The auxiliary port 110 is configured to facilitate external connections to one of the multi-port hubs 156 and 157. For example, in an embodiment as exemplarily illustrated in FIG. 1, the auxiliary port 110 is operably coupled, for example, in the console 108, for facilitating external connections to one of the multi-port hubs 156 and 157. In another embodiment, the auxiliary port 110 is operably coupled to the deck 130 proximal to the patient undergoing a remote medical examination. In another embodiment, the auxiliary port 110 is configured on the upper shell 102 and/or the lower shell 103 of the casing 101 for facilitating external connections to one of the multi-port hubs 156 and 157, when the casing 101 is in an open position. The auxiliary port 110 is operably coupled to a switching port 157a of the multi-port hub 157 exemplarily illustrated in FIG. 8, for delivering power to the external connections and executing data exchange with the external connections, for example, with an external USB device.

In another embodiment, the medical diagnostic kit 100 further comprises illuminating control elements 109 positioned on the console 108. The illuminating control elements 109 are operably coupled to switchable ports 156a and 157a of the multi-port hubs 156 and 157 respectively. The illuminating control elements 109, for example, illuminating switches or buttons, are configured to activate or deactivate one or more of the clinical examination devices and one or more of the accessories engaged in a particular medical examination to save battery power and facilitate data bus sharing such as USB bus sharing. The illuminating control elements 109 are configured to switch on or off a particular clinical examination device according to a diagnostic scenario to save battery power. An operator of the medical diagnostic kit 100 may activate one of the illuminating control elements 109 corresponding to a particular clinical examination device used for examining a patient according to a diagnostic scenario and deactivate the other illuminating control elements 109 corresponding to the other clinical examination devices and accessories. By deactivating the other illuminating control elements 109, the power from the energy storage device(s) 154 to the switchable ports 156a and 157a, for example, the USB ports, of the multi-port hubs 156 and 157 respectively, exemplarily illustrated in FIG. 8, to which the individual cable connectors of the clinical examination devices and the accessories are connected, is interrupted, thereby saving power. The illuminating control elements 109 provide visual information to the operator about a switchable port 156a or 157a being energized. The cables of the clinical examination devices and the accessories terminate at their respective connectors which are connected to the switchable ports 156a and 157a of the multi-port hubs 156 and 157 respectively. These cables are, for example, power supply and data communication or exchange cables such as USB cables.

The disconnection member 112 is operably connected between the upper shell 102 and the lower shell 103 of the casing 101. In an embodiment, the disconnection member 112 is a switch lever operably coupled to an edge 108a of the console 108 as exemplarily illustrated in FIG. 1. In another embodiment, the disconnection member 112 is a sensor operably connected between the upper shell 102 and the lower shell 103 of the casing 101 and configured to detect the closed position of the casing 101. The disconnection member 112 is in operable communication with the hubs disconnection switch 144 exemplarily illustrated in FIG. 6A and FIG. 8. The hubs disconnection switch 144 is operably coupled to the energy storage device(s) 154 and external power jacks 156b and 157b of the multi-port hubs 156 and 157 as exemplarily illustrated in FIG. 8. The hubs disconnection switch 144, when activated by the disconnection member 112, is configured to interrupt delivery of power from the energy storage device(s) 154 to the multi-port hubs 156 and 157, when the casing 101 is in the closed position to save battery power, and in compliance with air transportation safety rules. When the upper shell 102 of the casing 101 is closed, the disconnection member 112 turns and activates the hubs disconnection switch 144. In another embodiment (not shown), the disconnection member comprises a magnet (not shown) attached to the upper shell 102 and a reed relay (not shown) housed underneath the console 108. In this embodiment, when the upper shell 102 of the casing 101 is closed, the magnet, in operable communication with the reed relay, activates the hubs disconnection switch 144 to interrupt the delivery of the power from the energy storage device(s) 154 to the multi-port hubs 156 and 157. The disconnection member 112 activates the hubs disconnection switch 144 to disconnect the energy storage device(s) 154 when the casing 101 is in a fully closed position for transporting the medical diagnostic kit 100 and preserving the internal energy of the energy storage device(s) 154.

When the casing 101 is connected to a power source, for example, an alternating current (AC) power source, during an AC charging operation, the energy storage device(s) 154 is configured to receive power from the multi-port charger 150. When the casing 101 is in the open position and disconnected from the power source, power stored in the energy storage device(s) 154 is used to power the clinical examination devices and the accessories via the multi-port hubs 156 and 157. When the casing 101 is in the closed position and disconnected from the power source, the disconnection member 112 activates the hubs disconnection switch 144 to disconnect the energy storage device(s) 154 from the multi-port hubs 156 and 157, thereby interrupting power from being delivered to power up the clinical examination devices and the accessories and precluding discharging of the energy storage device(s) 154.

The computing devices 114 and 115 are supportably positioned in the casing 101. In an embodiment, the computing devices 114 and 115 are supportably positioned in the upper cavity 102f of the upper shell 102 of the casing 101. In an embodiment, one of the computing devices is a diagnostic computer 114, for example, a Microsoft Surface® Pro 7 computing device of Microsoft Corporation with a 10th Gen Intel® Core™ i5 processor. In an embodiment, the diagnostic computer 114 is accommodated in a device holder 125 positioned in the casing 101, for example, in the upper cavity 102f of the upper shell 102 of the casing 101. In an embodiment, the device holder 125 is attached to the casing 101 via an attachment member (not shown), for example, a spherical holder, to provide training of a video camera (not shown) of the diagnostic computer 114 on the patient. The diagnostic computer 114 is configured to (a) activate one or more of the clinical examination devices; (b) execute media conference connections, for example, audio/videoconference connections; (c) receive, create, record, process, store, and securely transmit medical data from one or more of the clinical examination devices to a data store or a data storage device via a communication network, for example, a wireless communication network; and (d) facilitate remote real-time medical examinations via a software application deployed on the diagnostic computer 114. The software application in the diagnostic computer 114 is configured to activate and operate the clinical examination devices selected by the illuminating control elements 109. In an embodiment, the software application is a web-based application with audio/videoconference connections for conducting remote real-time medical examinations. In an embodiment, the software application is implemented on a Health Insurance Portability and Accountability Act (HIPAA)-compliant data streaming and store-and-forward platform.

The software application creates medical data that is temporarily stored in the diagnostic computer 114. The software application transfers the medical data over a secure wideband, stable, wireless connection to the data storage device. If a communication link to the physician's remote computing device is not available, the medical diagnostic kit 100 is configured to store medical data, for example, the patient's vital signs, sonograms, electrocardiograms (ECGs), auscultation sounds, camera images, etc., securely in an internal storage device for a later upload or an artificial intelligence (AI)-enabled batch upload to the physician's remote computing device, when the communication network is available. In an embodiment, the software application transfers the medical data over a secure wideband, stable, wireless connection to a cloud data store in a cloud computing environment. As used herein, "cloud computing environment" refers to a processing environment comprising configurable, computing, physical and logical resources, for example, networks, servers, storage media, virtual machines, applications, services, etc., and data distributed over a communication network, for example, the internet. The cloud computing environment provides an on-demand network access to a shared pool of the configurable computing physical and logical resources. The medical data is stored in the cloud data store in a digital format for future diagnostic or therapeutic use. In an embodiment, upon successful transfer of the medical data, the software application removes the medical data from the diagnostic computer 114. The diagnostic computer 114 allows a user, for example, an operator of the medical diagnostic kit 100, to sign in to the software application through a restricted user account and rotated password. After a period of inactivity, the software application displays a screen saver on the diagnostic computer 114. After an additional period of inactivity, the software application locks the diagnostic computer 114 and requests the user to sign in again to regain access.

In an embodiment, the software application allows health care practitioners at a remote site to suggest the use of the clinical examination devices and the accessories in the medical diagnostic kit 100. In this embodiment, the software application is configured to display, on the diagnostic computer 114, a panel of the clinical examination devices and the accessories accommodated in the medical diagnostic kit 100 and indications of one or more of the clinical examination devices and the accessories on the panel suggested by a health care practitioner at a remote site for usage during the remote real-time medical examinations. The health care practitioner will have a copy of the panel in their remote application and by activating a clinical examination device or accessory remotely, the onsite operators of the medical diagnostic kit 100 at the patient's location receive the indication that visually suggests to them to apply the activated clinical examination device or accessory to the patient.

In an embodiment, another one of the computing devices is a communication device 115 in operable communication with the diagnostic computer 114 via the communication network. The communication device 115 is configured to display a media stream, for example, a video stream, from one or more of the clinical examination devices. In an embodiment, the communication device 115 is configured to remotely control the software application deployed on the diagnostic computer 114. In an embodiment, the communication device 115 is a tablet computing device comprising a display unit 115a configured to assist in aiming a camera lens of one of the clinical examination devices, for example, the multi-organ imaging system 118, and visualizing one or more of multiple organs, for example, eyes, nose, throat, skin, etc., of a patient. The display unit 115a is configured to receive and display a media stream, for example, a video stream, of each of the visualized organs captured by the clinical examination device(s), for example, 118, via the camera lens. In an embodiment, the communication device 115 is accommodated in a removable device holder 116 lockably positioned in the casing 101, for example, in the upper cavity 102f of the upper shell 102 of the casing 101. When unlocked and removed from the casing 101, the device holder 116 is configured to assist in attaching the communication device 115 to one or more of the clinical examination devices, for example, a camera device such as a throat or skin exam camera. In an embodiment, the device holder 116 is removable during use and configured to be locked in position in the casing 101 using an attachment member (not shown). The removable device holder 116 is configured to be unlocked and slid out from the attachment member for attachment to other clinical examination devices, for example, a throat or skin exam camera, via a mechanical coupling such as a ball coupling. FIG. 1 exemplarily illustrates the removable device holder 116 in an unlocked position ready to be taken out of the casing 101. In the unlocked position, the communication device 115 is ready to be pulled out along with the removable device holder 116. In an embodiment, the removable device holder 116 with the communication device 115 is configured to be detachably attached to a spherical mounting member (not shown) extending from one of the clinical examination devices, for example, the multi-organ imaging system 118, for conducting an ear, nose, and throat (ENT) and skin examination using the display unit 115a of the communication device 115.

In an embodiment, the medical diagnostic kit 100 further comprises a device holder 117 positioned in the casing 101, for example, in the upper cavity 102f of the upper shell 102 of the casing 101, for accommodating another computing device, for example, a network-enabled mobile phone 149 exemplarily illustrated in FIG. 8. In an embodiment, the device holder 117 that accommodates the network-enabled mobile phone 149 is non-removable. The network-enabled mobile phone 149 is configured, for example, as a mobile hotspot, to provide access of a wireless communication network, for example, a fourth generation (4G) wireless network, a fifth generation (5G) wireless network, the Wi-Fi® communication network of Wi-Fi Alliance Corporation, a satellite communication network provided by a satellite internet constellation such as the Starlink® internet constellation operated by Space Exploration (SpaceX) Technologies Corporation, etc., to the diagnostic computer 114 and the communication device 115.

The removable device holder 116 holds the communication device 115. In an embodiment, a lockable slider (not shown) with a ball capture component (not shown), for example, a chuck, is attached to a rear surface of the removable device holder 116. The lockable slider interacts with rails configured on a pivotable receiver 116a attached to the upper support wall 102a of the upper shell 102 of the casing 101. The lockable slider moves along the rails of the pivotable receiver 116a. The lockable slider latches into a stow position with the device holder 116 holding the communication device 115 positioned parallel to the upper support wall 102a of the upper shell 102 of the casing 101. The lockable slider is unlatched by pressing down on the device holder 116 to disengage a latch of the lockable slider. The rails of the pivotable receiver 116a then pivot out and the device holder 116 attached to the lockable slider can be pulled up and out with the communication device 115. The device holder 116 with the communication device 115 is stowed by engaging the lockable slider back into the rails in a downward direction and pivoting the rails back till the latch of the lockable slider engages and locks the device holder 116 in position.

The lockable slider is unlocked by pushing the device holder 116 down, pivoted out as exemplarily illustrated in FIG. 1, and then slid out from the pivotable receiver 116a with the communication device 115 as a single unit. In an embodiment, the device holder 116 with the communication device 115 is configured to be held in the hands of an operator of the medical diagnostic kit 100, for example, a technician, to control the diagnostic computer 114 or interface with corresponding clinical examination devices, for example, an ultrasound device (not shown). An operator of the medical diagnostic kit 100 may hold the pulled-out communication device 115 in their hands to control the diagnostic computer 114 or to interface with corresponding clinical examination devices. The ball capture component behind the device holder 116 holding the communication device 115 is also attachable to a ball mount of a clinical examination device, for example, a throat or skin exam camera, to assist in aiming of the camera. After concluding a medical examination using the camera, the device holder 116 with the communication device 115 is disengaged from the ball mount of the camera and the camera is returned into a corresponding slot, for example, 105f, of the cushioning member 105. The device holder 116 with the communication device 115 is configured to be attached to other devices having ball mounts to which the ball capture component of the device holder 116 can attach.

The device holder 116 assists in handling the communication device 115 by providing additional elements, for example, the ball capture component, for the operator to hold onto. When communication device operations are completed, the device holder 116 with the communication device 115 is slid back into the pivotable receiver 116a and pivoted back for locking in place parallel to the upper support wall 102a of the upper shell 102 of the casing 101 to save space in a stowable position. In an embodiment, the device holder 125 that holds the diagnostic computer 114 is movably positioned in the upper shell 102 of the casing 101. The device holders 116 and 125 are configured to hold computing devices of different sizes and are configured to be attached to similar ball mounts are disclosed above. The device holder 125 is pivotably connected to the upper support wall 102a of the upper shell 102 of the casing 101. The device holder 125 is configured to assist in aiming a camera of the diagnostic computer 114 when pivoted. In an embodiment, the device holder 125 attaches to a ball mount (not shown) positioned on the upper support wall 102a of the upper shell 102 of the casing 101. The device holder 125 pivots about the ball mount, thereby allowing pivoting of the diagnostic computer 114 accommodated in the device holder 125 to aim at a patient. In an embodiment, the device holder 117 is attached to a ball mount (not shown) positioned on the upper support wall 102a of the upper shell 102 of the casing 101. In an embodiment, the device holders 117 and 125 are not removable during normal operations and are removed for service.

In an embodiment, the device holders 116, 117, and 125 are spring-loaded and are configured to securely hold computing devices of different sizes, for example, 115, 149, and 114 respectively. In an embodiment, lockable sliders with ball capture components (not shown) are attached to the rear surfaces of the device holders 116, 117, and 125 and operate as disclosed above. In an embodiment, the ball capture component of the device holder 116 is configured to connect to a ball mount of a clinical examination device, for example, a camera. In another embodiment, the ball capture components of the device holders 117 and 125 are friction locked to respective ball mounts attached to the upper support wall 102a of the upper shell 102 of the casing 101. The ball mount configured for the device holder 125 allows pivoting in a predefined range of a videoconferencing camera of the diagnostic computer 114 towards the patient. In an embodiment, the ball capture component of the device holder 117 is fastened firmly to its ball mount on the upper support wall 102a of the upper shell 102 of the casing 101 and is therefore not removable.

In an embodiment, a side door 113 is hinged to a door frame 137 attached to one of the side walls 103b, 103c, 103d, and 103e of the casing 101. For example, the side door 113 is exteriorly positioned on the side wall 103d of the lower shell 103 of the casing 101 via a door hinge 113a. The side door 113 covers a gasket 136 positioned within the door frame 137 exemplarily illustrated in FIG. 4, thereby providing dust and water proofing. The medical diagnostic kit 100 further comprises inlet ports and outlet ports as disclosed in the detailed description of FIG. 4. The inlet ports and the outlet ports are positioned, for example, on the side wall 103d of the casing 101. The side door 113 is configured to close over the gasket 136 within the door frame 137 and protect the inlet ports and the outlet ports from dust, water, and other external elements. As exemplarily illustrated in FIG. 1, another slot 105g of the cushioning member 105 exposes an air intake grill 107a of a fan protector 107 affixed to the deck 130 as exemplarily illustrated in FIG. 3. The air intake grill 107a receives air flow from the upper cavity 102f of the upper shell 102 of the casing 101 and passes the air towards an outlet port, for example, a louver 139, on the side wall 103d of the casing 101 exemplarily illustrated in FIG. 4, to cool down the energy storage device(s) 154, the multi-port charger 150, the computing devices 114, 115, and 149, the clinical examination devices, and the accessories during charging thereof.

The medical diagnostic kit 100 is provided to users or operators, for example, onsite care coordinators (OCCs), nurses, technicians, etc., with instructions, guidance, out-of-range warnings, hazardous situation warnings, battery capacity gauges, electrical shock protection, device operation instructions, cleaning and sterilization instructions, connector and cable support instructions, customer support instructions, etc. Users, for example, telepresenters, OCCs, etc., are dispatched with the medical diagnostic kits 100 to patient locations while remote health care practitioners, for example, physicians, are waiting online to conduct remote physical data-unreached medical examinations. In an embodiment, the medical diagnostic kit 100 is lightweight and portable.

FIG. 2 exemplarily illustrates a perspective view of an embodiment of the universal cable storage compartment 126 of the medical diagnostic kit 100 shown in FIG. 1. The universal cable storage compartment 126 is accommodated in the casing 101. In an embodiment, the universal cable storage compartment 126 is accommodated in the lower cavity 103f of the lower shell 103 of the casing 101 exemplarily illustrated in FIG. 1. In an embodiment, the universal cable storage compartment 126 is of a generally rectangular shape as exemplarily illustrated in FIG. 2. The universal cable storage compartment 126 is made, for example, from a lightweight plastic or a metal alloy such as a magnesium silicide type of wrought aluminum or aluminum 6062. The universal cable storage compartment 126 comprises movable dividers 127 and subdividers 128 configured to create configurable cable compartments 129a, 129b, 129c, 129d, and 129e or holders for accommodating cables (not shown) used to connect multiple clinical examination devices to the multi-port hubs 156 and 157 exemplarily illustrated in FIG. 8, without mutual entanglement. For example, the cable compartments 129a, 129b, 129c, 129d, 129e, and 129f accommodate cables of the otoscope 124, the electrocardiograph 119, the blood pressure monitor 120, the oximeter 121, the stethoscope 122, and the multi-organ imaging system 118 respectively, as exemplarily illustrated in FIG. 1. The individual cables are coiled in separate cable compartments 129a, 129b, 129c, 129d, 129e, and 129f divided by the dividers 127 and the subdividers 128. The dividers 127 are configured to create large cable compartments 129a, 129b, 129c, and 129f for accommodating large cables of large clinical examination devices, while the subdividers 128 are configured to create small cable compartments 129d and 129e for accommodating small cables of small clinical examination devices. The dividers 127 and the subdividers 128 are movable to accommodate cables of future variants of the clinical examination devices.

In an embodiment, the universal cable storage compartment 126 further comprises flanges 126a protruding from the edges 126b of the universal cable storage compartment 126. The flanges 126a provide an attachment surface for attaching the deck 130 to the universal cable storage compartment 126 in the lower cavity 103f of the lower shell 103 of the casing 101 exemplarily illustrated in FIG. 1 and FIG. 6A. The universal cable storage compartment 126 further comprises openings 126c through which connectors of the cables of the clinical examination devices are inserted, extended, and affixed to the switchable ports 156a and 157a of the multi-port hubs 156 and 157 respectively, exemplarily illustrated in FIG. 8. In an embodiment, the universal cable storage compartment 126 further comprises a supplementary port 126d positioned on a side wall 126e of the universal cable storage compartment 126 for connecting a connector of a cable of one of the clinical examination devices or one of the accessories.

The universal cable storage compartment 126 is a dedicated storage compartment in the medical diagnostic kit 100 for accommodating the cables of the clinical examination devices in an orderly manner to prevent entanglement of the cables. The cable compartments 129a, 129b, 129c, 129d, 129e, and 129f formed by the movable dividers 127 and subdividers 128 allow accommodation of cables of clinical examination devices of different types, configurations, and future variants therewithin. The universal cable storage compartment 126 allows permanent cabling of the clinical examination devices to the multi-port hubs 156 and 157. The universal cable storage compartment 126 provides integrated individual cable stowage under the clinical examination devices supported by the cutouts 131a, 131b, 131c, 131d, 131e, and 131f of the deck 130 exemplarily illustrated in FIG. 3.

FIG. 3 exemplarily illustrates a perspective view of an embodiment of the deck 130 of the medical diagnostic kit 100 shown in FIG. 1. The deck 130 is positioned on the universal cable storage compartment 126 exemplarily illustrated in FIG. 2. In an embodiment, the deck 130 is positioned over the universal cable storage compartment 126 in the lower cavity 103f of the lower shell 103 of the casing 101 exemplarily illustrated in FIG. 1. The deck 130 positioned on the universal cable storage compartment 126 supports the clinical examination devices and the accessories. The deck 130 is made, for example, from a lightweight plastic or thin metal sheets such as thin aluminum sheets. The deck 130 comprises multiple cutouts 131a, 131b, 131c, 131d, 131e, and 131f positioned in a one-to-one correspondence to the configurable cable compartments 129a, 129b, 129c, 129d, 129e, and 129f of the universal cable storage compartment 126 respectively, exemplarily illustrated in FIG. 2. In an embodiment, the cutouts 131a, 131b, 131c, 131d, 131e, and 131f of the deck 130 are configured to support the clinical examination devices and the accessories in multiple configurations and provide openings to the cable compartments 129a, 129b, 129c, 129d, 129e, and 129f respectively, for extension and stowage of the cables of the clinical examination devices and the accessories. The cutouts 131a, 131b, 131c, 131d, 131e, and 131f of the deck 130 correspond to individual divisions inside of the universal cable storage compartment 126 which accommodate individual cables of the clinical examination devices and the accessories.

The deck 130 provides a layout for accommodating the clinical examination devices on a surface layer. In an embodiment, the deck 130 further comprises a cutout 131g used for accommodating an accessory, for example, a wireless speaker 123, via the slot 105e in the cushioning member 105 exemplarily illustrated in FIG. 1. In an embodiment, the medical diagnostic kit 100 further comprises air circulation holes 133 configured proximal to the edge 130a of the deck 130. In an embodiment, the air circulation holes 133 are positioned on a flange 130b of the deck 130. The air circulation holes 133 are configured to assist in movement of forced air provided by an air-cooling fan system 153 exemplarily illustrated in FIG. 8, during charging of the computing devices 114, 115, and 149, the clinical examination devices, the accessories, and other devices accommodated in the upper cavity 102f of the upper shell 102 of the casing 101, powered by the multi-port charger 150. For example, the air circulation holes 133 circulate air, for example, from the lower cavity 103f defined by the lower shell 103 to the upper cavity 102f defined by the upper shell 102 of the casing 101.

In an embodiment, the deck 130 is configured to define a space 132 indicated by dashed lines in FIG. 3, for accommodating the console 108 of the medical diagnostic kit 100 exemplarily illustrated in FIG. 1. The console 108 is positioned proximal to and attached to an edge 130e of the deck

130. In an embodiment, the medical diagnostic kit 100 further comprises a fan protector 107 affixed to an upper surface 130c of the deck 130. The fan protector 107 is configured to protect an exhaust fan 145 of the air-cooling fan system 153 interiorly positioned proximal to the side wall 103d or to the fan backplate 138 of the casing 101 as exemplarily illustrated in FIGS. 6A-6B. The exhaust fan 145 is supported by the fan backplate 138 of the casing 101. The fan protector 107 comprises the air intake grill 107a that receives air flow from the upper cavity 102f of the upper shell 102 of the casing 101 and passes the air towards louvers 139 on the fan backplate 138 exemplarily illustrated in FIG. 4 and FIG. 6B. The cold outside air enters through the air intake port 141, is directed by an intake fan (not shown) of the air-cooling fan system 153 to blow around the multi-port charger 150 and the internal energy storage device(s) 154 in the lower cavity 103f of the lower shell 103 of the casing 101, and travels up through the air circulation holes 133 of the deck 130 into the upper cavity 102f of the upper shell 102 of the casing 101 exemplarily illustrated in FIG. 1, FIGS. 6A-6B, and FIG. 8, to cool down the computing devices 114, 115, and 149, the clinical examination devices, and the accessories, during charging thereof.

To accommodate a new instrument or clinical examination device layout, the medical diagnostic kit 100 requires only two components to be replaced, that is, the deck 130 and the cushioning member 105 exemplarily illustrated in FIG. 1. The dividers 127 exemplarily illustrated in FIG. 2, are movable for accommodating new device boundaries. In an embodiment, the cushioning member 105 is glued to the upper surface 130c of the deck 130. In an embodiment, an optional secondary deck (not shown) is attached on top of the cushioning member 105 to protect the upper surface of the cushioning member 105 from scratching.

Figure 4:
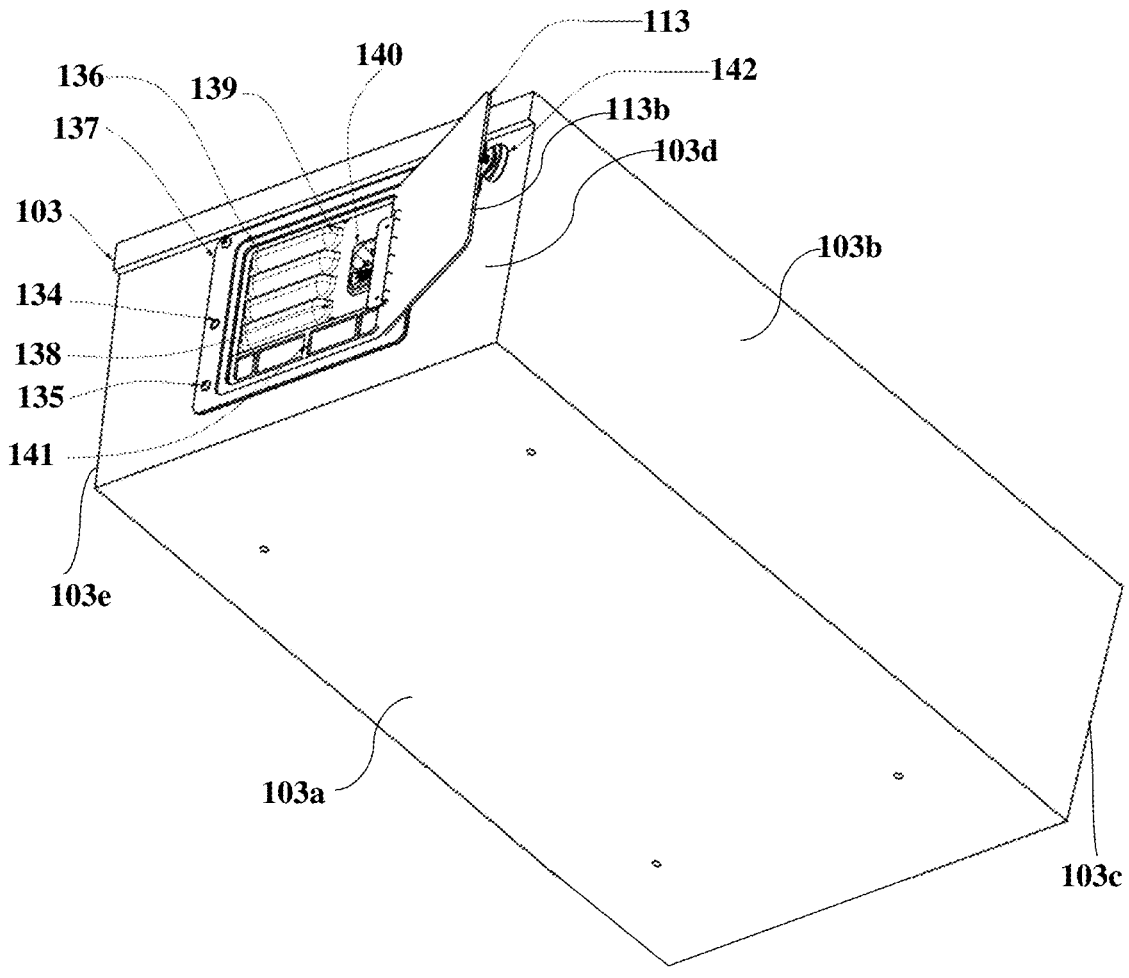
FIG. 4 exemplarily illustrates a bottom perspective view of a lower shell of a casing of an embodiment of the medical diagnostic kit.

FIG. 4 exemplarily illustrates a bottom perspective view of the lower shell 103 of the casing 101 of an embodiment of the medical diagnostic kit 100 shown in FIG. 1. As exemplarily illustrated in FIG. 4, the side door 113 is hinged to the door frame 137 exteriorly positioned on one of the side walls 103b, 103c, 103d, and 103e of the casing 101. In an embodiment as exemplarily illustrated in FIG. 4, the door frame 137 is exteriorly positioned on the side wall 103d of the lower shell 103 of the casing 101. The door frame 137 is attached to the side wall 103d using fasteners 135, for example, mounting screws. The side door 113 is connected to the door frame 137 using a hinge 113a as exemplarily illustrated in FIG. 1 and FIG. 5. The side door 113 is configured as a ventilation door. The inlet ports and outlet ports are also positioned on the side wall 103d of the lower shell 103 of the casing 101. The side door 113 provides access to the inlet ports and the outlet ports of the medical diagnostic kit 100. In an embodiment, the fan backplate 138 is exteriorly positioned on the side wall 103d of the lower shell 103 of the casing 101. A gasket 136 is positioned on the fan backplate 138 as a mechanical seal that fills a space between the fan backplate 138 and the side door 113. The side door 113 is hinged to the door frame 137 to cover the gasket 136 and the fan backplate 138 and to protect the inlet ports and the outlet ports from dust, water, and other external elements. In an example, a locking thumb screw 142 is positioned on an external surface 113b of the side door 113 for locking into a screw nut 134 positioned on the door frame 137, thereby locking the side door 113 in a closed position over the gasket 136.

In an embodiment, the inlet ports of the medical diagnostic kit 100 comprise an air intake port 141 and an alternating current (AC) fused inlet 140. The air intake port 141 allows air to flow into the casing 101, for example, into the lower cavity 103f of the lower shell 103 of the casing 101 exemplarily illustrated in FIG. 1 and FIGS. 6A-6B, for cooling the contents of the casing 101, for example, the energy storage device(s) 154, the multi-port charger 150, the computing devices 114, 115, and 149, the clinical examination devices, and the accessories. In an embodiment, the air intake port 141 comprises a particle filtering element or an air filter (not shown) for filtering the air entering the casing 101. In an embodiment, the medical diagnostic kit 100 further comprises an air-cooling fan system 153 exemplarily illustrated in FIG. 8. The air-cooling fan system 153 comprises cooling fans, for example, an exhaust fan 145 exemplarily illustrated in FIGS. 6A-6B, for exhausting heated internal air from the upper cavity 102f of the casing 101, and an intake fan (not shown) positioned in the lower cavity 103f of the casing 101. The intake fan draws air from the filtered air intake port 141 and blows the air, for example, on the multi-port charger 150 and the energy storage device(s) 154 exemplarily illustrated in FIG. 8, in the lower cavity 103f of the lower shell 103 of the casing 101.

The AC fused inlet 140 is configured, for example, as an AC socket such as an International Electrotechnical Commission (IEC) standard inlet, screw mounted, C14, to provide power from the AC power source to the multi-port charger 150 for charging the energy storage device(s), for example, 154, the computing devices 114, 115, and 149, the clinical examination devices, and the accessories exemplarily illustrated in FIG. 8, inside the casing 101 when the casing 101 is connected to an AC power source. A power cord 159 of the AC power source is connected to the AC fused inlet 140 to power the multi-port charger 150, and in turn, the energy storage device(s) 154, the air-cooling fan system 153, and the clinical examination devices, and accessories inside the casing 101 as exemplarily illustrated in FIG. 8. The AC fused inlet 140 allows powering of the multi-port charger 150, operation of the air-cooling fan system 153, and charging of rechargeable batteries of the energy storage device(s), for example, 154, the computing devices 114, 115, and 149, the clinical examination devices, and the accessories without opening the casing 101.

In an embodiment, the outlet ports of the medical diagnostic kit 100 comprise the louvers 139 positioned in the fan backplate 138. The louvers 139 are in fluid communication with the exhaust fan 145 positioned in the casing 101, for example, in the lower cavity 103f of the lower shell 103 of the casing 101 as exemplarily illustrated in FIGS. 6A-6B. The louvers 139 are a series of vents attached to one side of the exhaust fan 145 for regulating air flow up to and from the casing 101. The louvers 139 regulate the air flow to preclude hot exhaust air from mixing with cold intake air flow, thereby increasing efficiency of air cooling. The louvers 139 are configured to direct heated internal air in an upward direction into the upper cavity 102f of the casing 101 without mixing with incoming external or outside air flowing in the lower cavity 103f of the casing 101 for optimal cooling in the medical diagnostic kit 100 and increasing cooling efficiency. In an embodiment, the fan protector 107 affixed to the deck 130 as exemplarily illustrated in FIG. 4, protects the exhaust fan 145 interiorly positioned proximal to the fan backplate 138 of the casing 101. In an embodiment, the fan backplate 138 is configured to support the exhaust fan 145 interiorly positioned proximal to the side wall 103d. In an embodiment, the fan backplate 138 further comprises a side USB port (not shown) for external connections.

Figure 5:
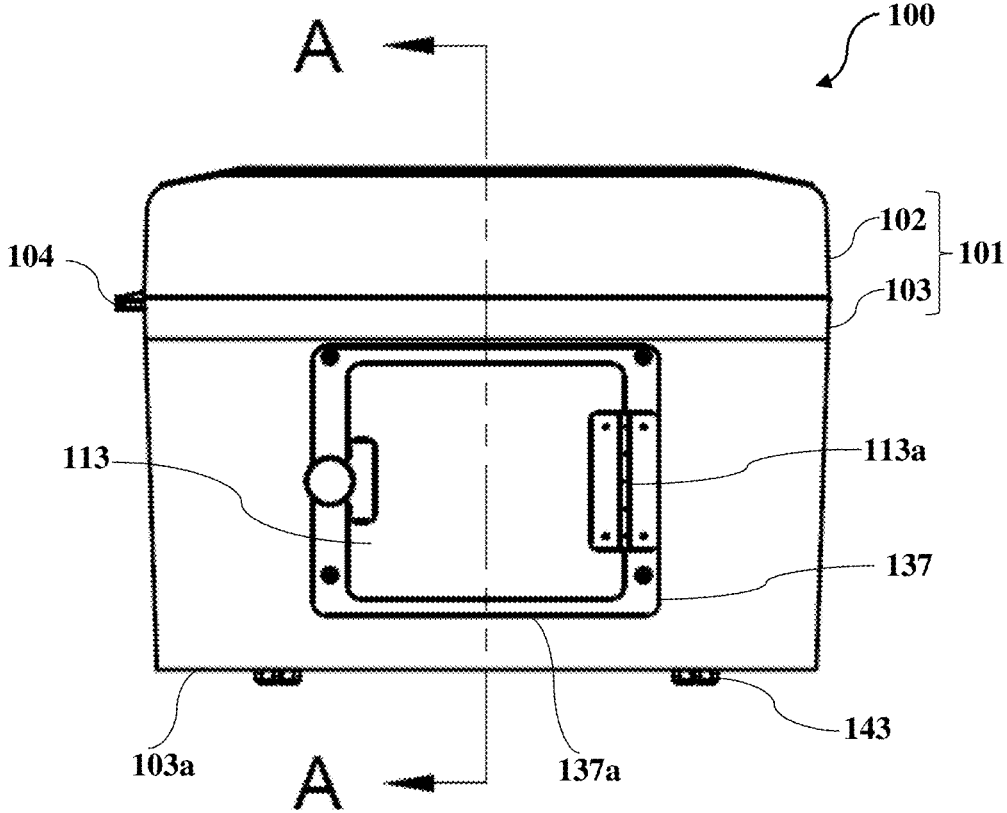
FIG. 5 exemplarily illustrates a left side view of an embodiment of the medical diagnostic kit.

FIG. 5 exemplarily illustrates a left side view of an embodiment of the medical diagnostic kit 100. The left side elevation view illustrates the hinges 104 and the side door 113 positioned on the casing 101. The side door 113 is closed during transportation and during an onsite medical examination. The side door 113 is opened when an alternating current (AC) power source is to be connected to the AC fused inlet 140 of the multi-port charger 150 exemplarily illustrated in FIG. 4 and FIG. 8, for charging the internal components of the medical diagnostic kit 100. The side door 113 is also opened to expose the air intake port 141 and the louvers 139 for ventilation of the medical diagnostic kit 100 during AC charging. The side door 113 is oriented such that when an AC power cord 159 is plugged into the AC fused inlet 140, the side door 113 cannot swing and inadvertently block the air intake port 141 and the louvers 139. In an embodiment, the hinge 113*a* of the side door 113 is positioned on a lower end 137*a* of the door frame 137 for opening the side door 113 in a downward direction. In this embodiment, opening the side door 113 in the downward direction precludes the side door 113 from closing the air intake port 141 inadvertently. In an embodiment, the medical diagnostic kit 100 further comprises wheels 143 operably coupled to and extending from the lower support wall 103*a* of the lower shell 103 of the casing 101. The wheels 143 are used for transporting the medical diagnostic kit 100.

FIG. 6A exemplarily illustrates a cross-sectional view of an embodiment of the medical diagnostic kit 100 taken along a section A-A shown in FIG. 5. The cross-sectional view shows the internal positioning of the components of the medical diagnostic kit 100 when the casing 101 is in the closed position. When the casing 101 is in the closed position, the hubs disconnection switch 144 is activated, interrupting power from the energy storage device(s) 154 to the multi-port hubs 156 and 157 exemplarily illustrated in FIG. 8. Furthermore, when the casing 101 is in the closed position or the open position, the side door 113 is opened for connecting an alternating current (AC) power cord 159 to the AC fused inlet 140 exemplarily illustrated in FIG. 4 and FIG. 8, and charging internal batteries, for example, the energy storage device(s) 154, batteries of the computing devices 114, 115, 149, etc., batteries of the clinical examination devices, batteries of the accessories, batteries of the cooling fans of the air-cooling fan system 153, etc., exemplarily illustrated in FIG. 8, in the casing 101.

In an embodiment, the air-cooling fan system 153 of the medical diagnostic kit 100 is positioned in the lower cavity 103*f* of the lower shell 103 of the casing 101 and operably coupled to the multi-port charger 150 as exemplarily illustrated in FIG. 8. In an embodiment, the air-cooling fan system 153 comprises one or more USB-powered intake fans (not shown) and exhaust fans 145 exemplarily illustrated in FIGS. 6A-6B. The air-cooling fan system 153 is configured to produce an air flow within the lower cavity 103*f* and the upper cavity 102*f* of the casing 101 for cooling the multi-port charger 150, the energy storage device(s) 154, the clinical examination devices 118, 119, 120, etc., the diagnostic computer 114, the communication device 115, the network-enabled mobile phone 149, and the accessories to prevent batteries overheating thereof when the casing 101 is in the closed position during charging. Arrows exemplarily illustrated in FIG. 6A are used to indicate the path of the air flow inside the casing 101 when the casing 101 is in the closed position. The air intake port 141 with the particle filter draws cold air inside the casing 101 and the intake fan (not shown) blows the cold air on the multi-port charger 150 and the energy storage device(s) 154. The cold air flows further towards the air circulation holes 133 in the deck 130 exemplarily illustrated in FIG. 3. The air circulation holes

133 allow movement of the cold air from the lower cavity 103*f* to the upper cavity 102*f* of the casing 101 and towards the computing devices 114 and 115. The upper air intake grill 107*a* receives heated air flow from the upper cavity 102*f* of the upper shell 102 of the casing 101 and passes the heated air towards the louvers 139 of the fan backplate 138 to allow the exhaust fan 145 interiorly positioned proximal to the fan backplate 138 to expel the heated air through the louvers 139. This airflow loop cools down the clinical examination devices 118, 119, 120, etc., the diagnostic computer 114, the communication device 115, and the network-enabled mobile phone 149 during charging thereof. The exhaust fan 145 exhausts heated internal air from the upper cavity 102*f* of the casing 101 out through the louvers 139.

As exemplarily illustrated in FIG. 6A, the deck 130 supports the universal cable storage compartment 126, the clinical examination devices, the accessories, and the cushioning member 105 of the casing 101. The air circulation holes 133 in the deck 130 communicate air between the upper cavity 102*f* and the lower cavity 103*f* of the casing 101. The air circulation holes 133 allow circulation of air from the lower cavity 103*f* of the lower shell 103 to the upper cavity 102*f* of the upper shell 102 in the casing 101. The cross-sectional view and section B exemplarily illustrated in FIGS. 6A-6B also show the exhaust fan 145 interiorly positioned proximal to the side wall 103*d* of the lower shell 103 of the casing 101. The exhaust fan 145 protected by the fan protector 107 affixed to the deck 130 and comprising the air intake grill 107*a*, draws air out from the upper cavity 102*f* of the casing 101 and expels the air out through the louvers 139. The air intake port 141 allows air pulled by the intake fan (not shown) to flow into the casing 101, for example, into the lower cavity 103*f* of the lower shell 103 of the casing 101 for cooling the contents of the casing 101, for example, the multi-port charger 150 and the energy storage device(s) 154.

During charging, the internal rechargeable batteries in the casing 101 generate heat. If the internal rechargeable batteries overheat, charging is interrupted until internal temperature drops down. The forced airflow generated by the air-cooling fan system 153 cools the multi-port charger 150, the energy storage device(s) 154, the clinical examination devices 118, 119, 120, etc., the diagnostic computer 114, the communication device 115, and the network-enabled mobile phone 149 with internal rechargeable batteries, facilitating fast battery charging and shortening recharge time. The air-cooling fan system 153 executes forced ventilation to facilitate cooling of the internal rechargeable batteries during charging. Charging the battery-driven internal components of the medical diagnostic kit 100, when the medical diagnostic kit 100 is in the closed position, protects the high-priced internal components, for example, the clinical examination devices 118, 119, 120, etc., the computing devices 114, 115, etc., when charging is done in public areas in the field or during transportation. Moreover, closed case charging allows several medical diagnostic kits 100 to be charged side-by-side in a narrow shelf space and reduces operational costs.

Figure 6B:
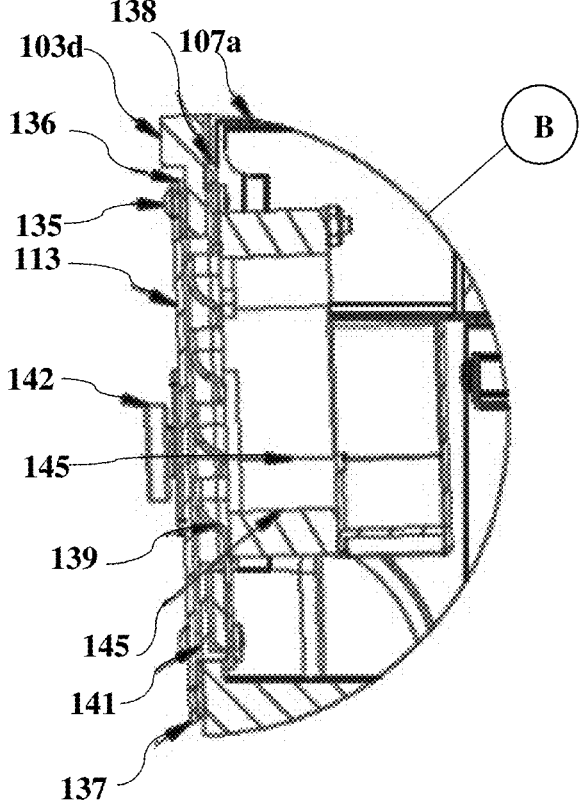
FIG. 6B exemplarily illustrates an enlarged view of a door and exhaust fan assembly section marked B in FIG. 6A.

FIG. 6B exemplarily illustrates an enlarged view of a door and exhaust fan assembly section marked B in FIG. 6A. The door and exhaust fan assembly section marked B shows the air intake grill 107*a* and parts positioned on the side wall 103*d* of the lower shell 103 of the casing 101, for example, the side door 113 with its locking thumb screw 142, the door frame 137, the fan backplate 138, the gasket 136, the louvers 139, and the air intake port 141 with the particle filter. The section marked B also shows the exhaust fan 145 interiorly supported against the side wall 103*d* of the casing 101.

Figure 7A:
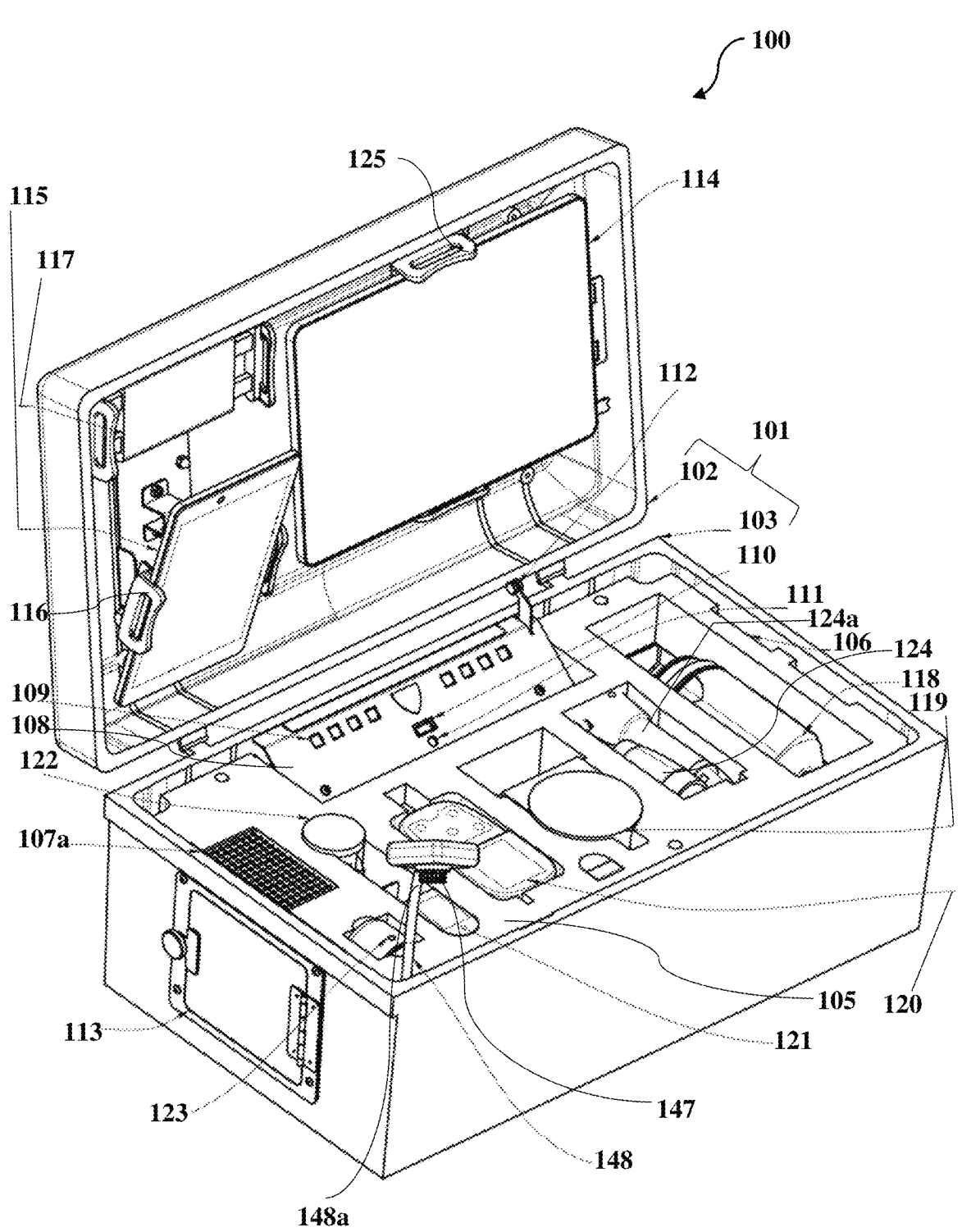
FIG. 7A exemplarily illustrates a top perspective view of an embodiment of the medical diagnostic kit comprising a secondary camera.

FIG. 7A exemplarily illustrates a top perspective view of an embodiment of the medical diagnostic kit 100 comprising a secondary camera 147. As exemplarily illustrated in FIG. 7A, the upper shell 102 of the casing 101 houses the device holders 125, 116, and 117 that accommodate the diagnostic computer 114, the communication device or tablet computing device 115, and the network-enabled mobile phone or mobile hotspot 149 respectively, as exemplarily illustrated in FIG. 8. The lower shell 103 of the casing 101 houses the console 108 containing the multi-port hubs 156 and 157 with the switchable ports 156*a* and 157*a* respectively, having the illuminating control elements 109 exemplarily illustrated in FIG. 8. The console 108 also houses an auxiliary universal serial bus (USB) connector 110 and a headset jack 111. The lower shell 103 of the casing 101 also houses the deck 130 exemplarily illustrated in FIG. 3, and the cushioning member 105 or foam block with slots 105*a*, 105*b*, 105*c*, 105*d*, 105*e*, and 105*f* for accommodating the clinical examination devices as exemplarily illustrated in FIG. 1. Underneath the deck 130 lies the universal cable storage compartment 126 exemplarily illustrated in FIG. 2, for accommodating the cables of the clinical examination devices, the multi-port charger 150, the energy storage device(s) 154, and the cooling fans, that is, the intake fan (not shown) and the exhaust fan 145 of the air-cooling fan system 153 exemplarily illustrated in FIGS. 6A-6B and FIG. 8.

In an embodiment, the medical diagnostic kit 100 further comprises a secondary camera 147 extending from a flexible mount 148, for example, a goose neck, in the casing 101. The flexible mount 148 is configured to aim a camera lens of the secondary camera 147 towards a patient and allow a health care practitioner at a remote site to view the patient when the patient is out of view of a camera of the diagnostic computer 114. The secondary camera 147 is operably coupled to one of the multi-port hubs 156 and 157 using an internal power supply and data communication or exchange cable (not shown), for example, a USB cable, positioned in the flexible mount 148. For example, a USB connector of the internal USB cable of the secondary camera 147 plugs into the auxiliary port 110 in the console 108. The secondary camera 147 is then stowed away into a holder (not shown) provided in the casing 101. In an embodiment, the secondary camera 147 and its flexible mount 148 are attached below the diagnostic computer 114 in the upper shell 102 of the casing 101 using magnets (not shown). The flexible mount 148 positions the secondary camera 147 such that the remote health care practitioner may view areas obstructed to a main videoconferencing camera on the diagnostic computer 114. The secondary camera 147 is placed closer to the patient for local patient observation, for example, during an electrocardiograph (ECG) examination and an auscultation when the patient is in a lying down position.

In an embodiment, a lower end (not shown) of the flexible mount 148 is connected to the deck 130 via a holder (not shown) in the casing 101, while the secondary camera 147 connected to the upper end 148*a* of the flexible mount 148 is accommodated in a holder (not shown) positioned in a slot of the cushioning member 105 above the deck 130. When the casing 101 is in the open position, an operator of the medical diagnostic kit 100 removes the secondary camera 147 from the slot or detaches the secondary camera 147 from the magnets and allows the secondary camera 147 to suspend from the upper end 148*a* of the flexible mount 148. The flexible mount 148 allows the secondary camera 147 to be positioned such that a remote health care practitioner performing a remote medical examination through the diagnostic computer 114 may view a patient lying on a bed, while the operator measures the patient's vital signs, blood pressure, etc., or performs imaging of organs of the patient using the clinical examination devices.

In an embodiment, the secondary camera 147 is a universal serial bus (USB) camera operably connected to one of the switchable ports 157*a* of the multi-port hub 157 as exemplarily illustrated in FIG. 8. The secondary camera 147 is in operable communication with the diagnostic computer 114 via the hubs 155 and 157 and the hubs disconnection switch 144. The secondary camera 147 transmits captured still images or video streams to the diagnostic computer 114, thereby allowing the remote health care practitioner to view the patient. In another embodiment, the secondary camera 147 is a network-enabled camera that communicates with the diagnostic computer 114 via a wireless communication network or a wireless communication protocol. For example, the secondary camera 147 is a Bluetooth® camera of Bluetooth Sig, Inc. The secondary camera 147 is paired with the diagnostic computer 114 for transmitting captured still images or video streams from the secondary camera 147 to the diagnostic computer 114, thereby allowing the remote health care practitioner to view the patient. The diagnostic computer 114 receives image streams wirelessly from the secondary camera 147, for example, via the Bluetooth® communication protocol, and decompresses and decodes the image streams for facilitating communication between the remote health care practitioner and the patient or the operator of the medical diagnostic kit 100.

Figure 7B:
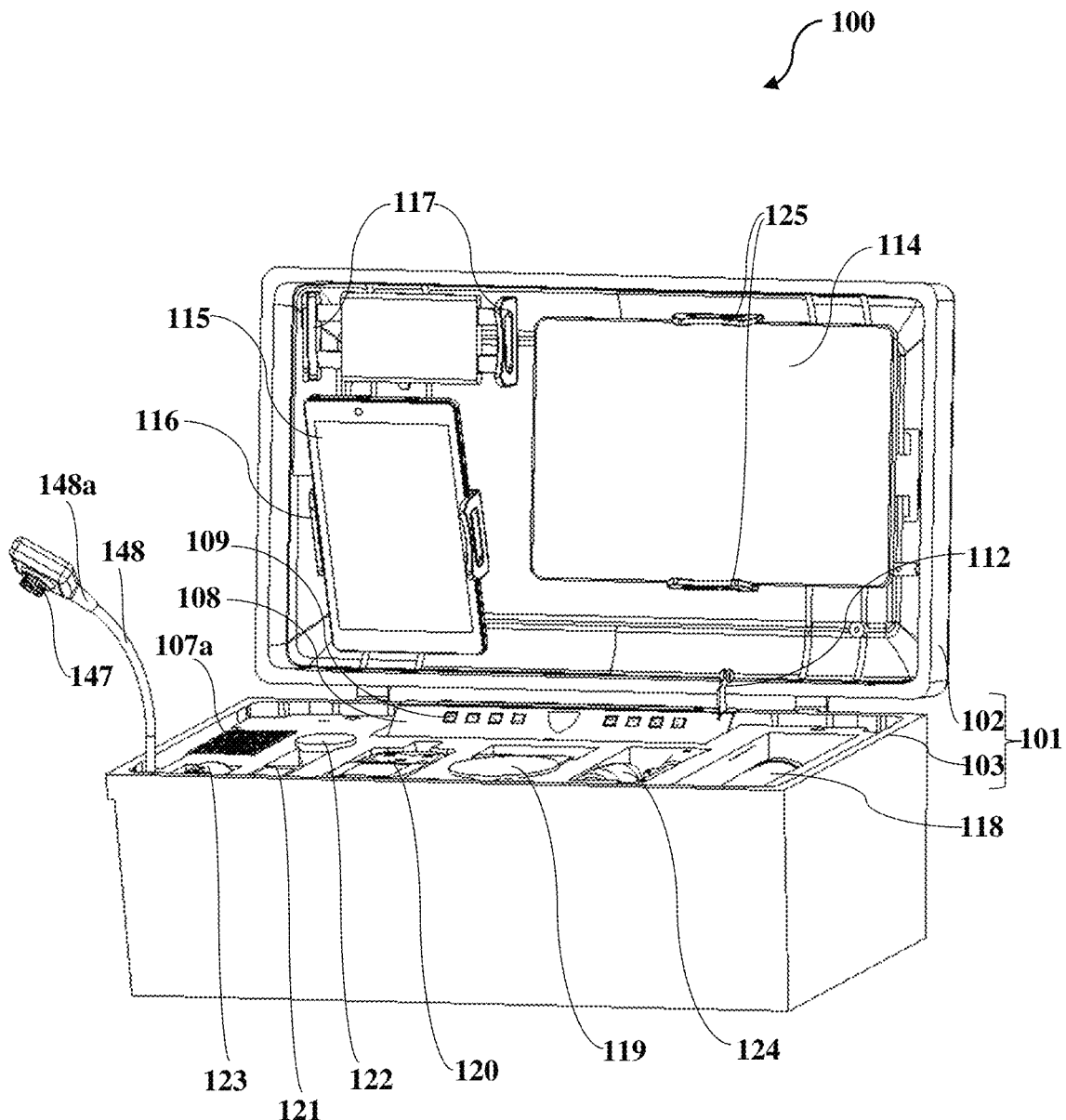
FIG. 7B exemplarily illustrates a front perspective view of the medical diagnostic kit shown in FIG. 7A.

FIG. 7B exemplarily illustrates a front perspective view of the medical diagnostic kit 100 shown in FIG. 7A. In an embodiment, the medical diagnostic kit 100 provides testing equipment or clinical examination devices comprising, for example, a stethoscope 122, a system for pulmonary, cardiac, and abdominal auscultation, an electrocardiograph (ECG) 119 such as a 12-lead, hospital grade ECG, a blood pressure monitor 120, an oximeter 121, an otoscope 124, a multi-organ imaging system 118 with an ultra-high resolution, universal serial bus (USB) 3.0 camera, no compression, with wide color reproduction and low distortion, and an ultrasound component that, in addition to its direct purpose, is also configured for use as an alternative to palpation. The multi-organ imaging system 118 allows for general, oral, dermatological, and otoscopic exams. Through the diagnostic computer 114, the medical diagnostic kit 100 implements a digital-format, cloud-storage mechanism for patient monitoring, thereby providing ready access of all files and medical data of a patient to a remote health care practitioner at any point in time, regardless of the size and format.

In addition to the computing devices 114 and 115, the clinical examination devices, for example, the multi-organ imaging system 118, the otoscope 124, the ECG 119, the blood pressure monitor 120, the oximeter 121, and the stethoscope 122, and the accessories, for example, the wireless speaker 123, FIG. 7B exemplarily illustrates the secondary camera 147 extending from the flexible mount 148 in the casing 101 as disclosed in the detailed description of FIG. 7A. The secondary camera 147 is connected to the auxiliary port 110 on the console 108 exemplarily illustrated in FIG. 7A, or to a switchable port 157*a* of the multi-port hub 157 exemplarily illustrated in FIG. 8, via a universal serial bus (USB) connection, and is selected by an illuminating control element 109 or switch on the console 108 exemplarily illustrated in FIG. 1. To start video streaming to a remote health care practitioner, an operator of the medical diagnostic kit 100 switches a video source in a conferencing component of the software application deployed in the diagnostic computer 114. The secondary camera 147 allows the remote health care practitioner to keep an eye on a patient lying on a bed, for example, during an ECG examination, when the patient is out of view of the diagnostic computer 114. The flexible mount 148 of the secondary camera 147 allows the operator to easily aim the secondary camera 147 towards the patient. In an embodiment, the secondary camera 147 is configured as a videoconferencing camera on the flexible mount 148 to show the remote health care practitioner areas obstructed to a main videoconferencing camera of the diagnostic computer 114. In an example, for an auscultation, the stethoscope 122 is pulled out of its cutout 131*e* or its slot 105*d* exemplarily illustrated in FIG. 3 and FIG. 1 respectively, and activated by a corresponding one of the illuminating control elements 109, while an audio card channel is selected in the videoconferencing software running on the diagnostic computer 114 and the headset 803 is plugged into the headset jack 111 exemplarily illustrated in FIG. 1 and FIG. 8. In various embodiments and alternative implementations of the medical diagnostic kit 100, the internal components of the medical diagnostic kit 100 may be interchangeably positioned in alternative, functionally equivalent configurations and arrangements within the upper cavity 102*f* and the lower cavity 103*f* of the casing 101 for a smooth operation of the medical diagnostic kit 100 and a smooth facilitation of remote real-time medical examinations.

FIG. 8 illustrates a block diagram showing an exemplary implementation of internal components of an embodiment of the medical diagnostic kit 100. The internal components of the medical diagnostic kit 100 comprise the multi-port charger 150, one or more energy storage devices 154, the hubs disconnection switch 144, a primary hub 155, and the multi-port hubs 156 and 157. The multi-port charger 150 is, for example, a 5-port alternating current (AC)-direct current (DC) charger comprising four universal serial bus (USB)-A ports 150*a*, 150*b*, 150*c*, and 150*d*, a power delivery (PD) port 150*e*, and the AC fused inlet 140 as exemplarily illustrated in FIG. 8. The multi-port charger 150 converts AC power received from an AC power source through an AC power cord 159 to DC power for distribution to the ports 150*a*, 150*b*, 150*c*, 150*d*, and 150*e*. In this embodiment, two of the USB-A ports 150*a* and 150*b* of the multi-port charger 150 are configured for connection to the computing devices, for example, the network-enabled mobile phone 149, also referred to as a mobile hotspot, and the communication device 115, that is, the tablet computing device with the camera display unit 115*a* respectively, accommodated, for example, in the upper cavity 102*f* of the upper shell 102 of the casing 101 in their respective device holders 117 and 116 exemplarily illustrated in FIG. 1. The USB-A port 150*a* of the multi-port charger 150 is connected to a USB-C charge port 149*a* of the network-enabled mobile phone 149. The USB-A port 150*b* of the multi-port charger 150 is connected to a micro-USB or USB-C port 115*b* of the communication device 115.

The network-enabled mobile phone 149 and the communication device 115 communicate with the diagnostic computer 114 via a wireless communication protocol, for example, the Wi-Fi® communication protocol of Wi-Fi Alliance Corporation. In an embodiment, the network-enabled mobile phone 149 is configured as an internet access point or a hotspot, for example, a fifth generation (5G) Wi-Fi® hotspot for providing reliable access of a wireless communication network, for example, a Wi-Fi® network, to the diagnostic computer 114 and the communication device

115. In another embodiment, the communication device 115 is configured as an internet access point or a hotspot, for example, a 5G Wi-Fi® hotspot, for providing reliable access of a wireless communication network, for example, a Wi-Fi® network, to the diagnostic computer 114. In another embodiment, the diagnostic computer 114 connects to the communication device 115 and the network-enabled mobile phone 149 via a wired connection, for example, a USB connection. In another embodiment, the diagnostic computer 114 and the communication device 115 connect to a wireless router, for example, a Wi-Fi® router, to access a wireless communication network.

Another USB-A port 150*c* of the multi-port charger 150 is configured for connection to a power distribution board 152. The power distribution board 152 is operably coupled to the air-cooling fan system 153 for delivering power received from the multi-port charger 150 to the air-cooling fan system 153. The air-cooling fan system 153 is operably coupled to the multi-port charger 150 via the power distribution board 152. The air-cooling fan system 153 produces air flow within the casing 101 to prevent overheating of the multi-port charger 150, the energy storage device(s) 154, the clinical examination devices, the accessories, and the diagnostic computer 114 in the closed position of the casing 101 during charging of the clinical examination devices and the diagnostic computer 114. The power distribution board 152 is, for example, a +5 Volt (V) power distribution board that divides an electrical power feed into subsidiary circuits while providing a protective fuse or circuit breaker for each circuit in a common enclosure. In an embodiment, the power distribution board 152 comprises USB-A connectors configured to charge accessories such as the wireless speaker 123 exemplarily illustrated in FIG. 1, the rechargeable batteries of one or more of the clinical examination devices, for example, an illuminator battery 124*a* of an otoscope 124 via a cable 162 extending from a universal magnetic connector 161 exemplarily illustrated in FIGS. 10A-10D and FIGS. 11A-11D, the stethoscope 122 via a stethoscope interface component 802, etc. Another accessory, for example, a headset 803 is operably coupled to the stethoscope interface component 802 as disclosed in the detailed description of FIG. 9. In an embodiment, the multi-port hubs 156 and 157, the energy storage device(s) 154, the air-cooling fan system 153, the power distribution board 152, a hubs disconnection switch board, the stethoscope interface component 802, and the multi-port charger 150 are accommodated in the lower cavity 103*f* of the lower shell 103 of the casing 101 exemplarily illustrated in FIG. 6A.

Another USB-A port 150*d* of the multi-port charger 150 is configured for connection to the energy storage device(s) 154. In an embodiment, the energy storage device(s) 154 is configured as a power bank with a charging gauge. For example, the energy storage device(s) 154 is a 20000 milliampere-hour (mAh) USB-C power delivery power bank with a quick charge 3.0. In an embodiment, the energy storage device(s) 154 comprises an in micro-USB port 154*a* and an out USB-A port 154*b*. The USB-A port 150*d* of the multi-port charger 150 is connected to the in micro-USB port 154*a* of the energy storage device(s) 154 via a cable. The out USB-A port 154*b* of the energy storage device(s) 154 is connected to the hubs disconnection switch 144. The power delivery port 150*e* of the multi-port charger 150 is operably coupled to a power delivery port 155*a* of the primary hub 155. The power delivery port 150*e* handles high power and allows charging of the diagnostic computer 114 via the USB-C port 155*c* quickly over a USB connection. The USB-A ports 150*a*, 150*b*, 150*c*, and 150*d* and the power delivery port 150e of the multi-port charger 150 are connected to their respective devices via individual cables.

The primary hub 155 is also operably coupled to the diagnostic computer 114 and to the multi-port hubs 156 and 157. The hubs 155, 156, and 157 perform data communication between the diagnostic computer 114 and the clinical examination devices. The primary hub 155 is, for example, a 3-port USB-A to USB-C hub with a power delivery (PD) USB-C port 155c. In an embodiment, the primary hub 155 is an internal hub with no switches. During charging, the primary hub 155 provides power to charge the diagnostic computer 114 via a power delivery function of the USB-C port 155c. The primary hub 155 receives the power from the multi-port charger 150 and delivers the power to the diagnostic computer 114 for charging the diagnostic computer 114 and executing data communication between the diagnostic computer 114, the clinical data examination devices, and the accessories during a medical examination. Moreover, the primary hub 155 is powered from the diagnostic computer 114 via the power delivery port 114a during a medical examination. The diagnostic computer 114 receives power from the USB-C with power delivery port 114a via the primary hub 155 from the PD port 150e of the multi-port charger 150 when the casing 101 is connected to the AC power source via the AC power cord 159. The primary hub 155 further comprises three USB-A ports 155b and one USB-C port 155c. In an embodiment, two of the USB-A ports 155b are connected to the multi-port hubs 156 and 157. For example, the USB-A ports 155b of the primary hub 155 are connected to the USB-A ports 156c and 157c of the multi-port hubs 156 and 157 respectively, via individual cables. The multi-port hubs 156 and 157 are, for example, 4-switched port USB 3.0 hubs with individual power switches. The multi-port hubs 156 and 157 comprise switchable ports 156a and 157a respectively, for connection to the clinical examination devices and one or more of the accessories. Individually switchable ports 156a and 157a allow the use of the clinical examination devices with different speed USB ports dynamically without permanent degradation to the slowest connection. Each clinical examination device sets an individual communication speed per specific test performed during switching time. The multi-port hubs 156 and 157 with the switchable ports 156a and 157a respectively, also referred to as "switched hubs", are powered from the energy storage device 154 via the hubs disconnection switch 144 when the upper shell 102 of the casing 101 is opened. The multi-port hubs 156 and 157 receive power through the hubs disconnection switch 144 when the casing 101 is in an open position.

The multi-port hub 156 comprises USB-A ports 156a and 156c and a power port 156b, for example, a 5V, 2-3 Ampere(s) (A) port. Similarly, the multi-port hub 157 comprises USB-A ports 157a and 157c and a power port 157b, for example, a 5V, 2-3 Amp port. The power ports 156b and 157b of the multi-port hubs 156 and 157 respectively, are operably coupled to the hubs disconnection switch 144. The multi-port hubs 156 and 157 receive regular +5V DC power into respective power ports 156b and 157b from the energy storage device 154 via the hubs disconnection switch 144. The clinical examination devices are connected to the USB-A ports 156a and 157a of the multi-port hubs 156 and 157 respectively, via individual cable connectors of cables optimally stored in cable compartments 129a, 129b, 129c, 129d, 129e, and 129f of the universal cable storage compartment 126 exemplarily illustrated in FIG. 2, without mutual entanglement. For example, an audio cable of the stethoscope 122 connected to an USB audio card 801 via the stethoscope interface component 802 exemplarily illustrated in FIG. 8, the USB cables of the pulse oximeter (PDX) 121, the blood pressure monitor 120, and the electrocardiograph (ECG) 119 are permanently connected to the USB-A ports 156a of the multi-port hub 156 via their individual cable connectors. Accessories such as a cuff 158 of the blood pressure monitor 120 and ECG electrodes 119a of the ECG 119 are accommodated in the deck 130 or the cushioning member 105 of the medical diagnostic kit 100 exemplarily illustrated in FIG. 1. In an embodiment, the accessories are accommodated below the deck 130 in the separated cable compartments 129a to 129e of the universal storage compartment 126 exemplarily illustrated in FIG. 2 and FIG. 6A. Similarly, an auxiliary port 110 of the secondary camera 147, the otoscope 124, and the multi-organ imaging system 118 are permanently connected to the USB-A ports 157a of the multi-port hub 157 via their individual cable connectors. In an embodiment, a single USB-C PD cable connected from the diagnostic computer 114 to the primary hub 155 with power delivery performs a combination of charging of the diagnostic computer 114 and USB data communication to the diagnostic computer 114.

As exemplarily illustrated in FIG. 8, the energy storage device(s) 154 is operably coupled to the multi-port charger 150 and the multi-port hubs 156 and 157. The multi-port charger 150 is electrically connected to and configured to charge the computing devices 115 and 149, the energy storage device(s) 154, the clinical examination devices, and the accessories. The energy storage device(s) 154 is configured to receive power from the multi-port charger 150. The energy storage device(s) 154 also delivers the power to the multi-port hubs 156 and 157 via the hubs disconnection switch 144 for powering and communicating data with the clinical examination devices and the accessories when the casing 101 is in the open position. In an embodiment, the energy storage device(s) 154 is operably coupled to the multi-port hubs 156 and 157 via the hubs disconnection switch 144. The primary hub 155 is operably coupled to the multi-port charger 150 for power delivery. The energy storage device(s) 154, when charged by the multi-port charger 150, powers the multi-port hubs 156 and 157. The energy storage device(s) 154 and the clinical examination devices comprise rechargeable batteries, for example, lithium batteries having about 8 hours to about 10 hours of battery life. In an embodiment, when the casing 101 is in the open position, the hubs disconnection switch 144 is deactivated, thereby connecting the energy storage device 154 to the multi-port hubs 156 and 157, discharging the energy storage device 154, and delivering power from the energy storage device 154 to the multi-port hubs 156 and 157, for powering up the clinical examination devices. When the casing 101 is in the closed position, the hubs disconnection switch 144 is activated, thereby disconnecting the energy storage device 154 from the multi-port hubs 156 and 157 and interrupting the delivery of power from the energy storage device 154 to the multi-port hubs 156 and 157.

In an embodiment, the switchable ports 156a and 157a of the multi-port hubs 156 and 157 respectively, are universal serial bus (USB) switchable ports configured to permanently and securely connect the individual cable connectors of the clinical examination devices and selectively power and communicate data with one or more of the clinical examination devices and the accessories engaged in a particular medical examination. The individual cable connectors of the clinical examination devices extend from their respective cables accommodated in the universal cable storage compartment 126 below the deck 130 exemplarily illustrated in FIGS. 2-3. The console 108 exemplarily illustrated in FIG. 1, that houses the multi-port hubs 156 and 157, operates, for example, as a cable connectors attachment grid. The hubs disconnection switch 144, operably coupled to the energy storage device(s) 154 and the multi-port hubs 156 and 157, is in operable communication with the disconnection member 112 exemplarily illustrated in FIG. 1. The disconnection member 112 is configured to activate the hubs disconnection switch 144 and interrupt the delivery of the power from the energy storage device(s) 154 to the multi-port hubs 156 and 157 when the casing 101 is in the closed position. When the casing 101 is in the open position, the disconnection member 112 is configured to deactivate the hubs disconnection switch 144 and allow delivery of power from the energy storage device 154 to the multi-port hubs 156 and 157, for powering up the clinical examination devices.

During the operation of the medical diagnostic kit 100 for performing a medical examination, an operator opens the upper shell 102 of the casing 101 and selects one of the clinical examination devices, for example, the multi-organ imaging system 118, by activating one of the illuminating control elements 109 on the console 108 exemplarily illustrated in FIG. 1. The operator then removes the multi-organ imaging system 118 from the corresponding slot 105*f* of the cushioning member 105 exemplarily illustrated in FIG. 1. When the casing 101 is in the open position, the disconnection member 112 exemplarily illustrated in FIG. 1, deactivates the hubs disconnection switch 144, thereby connecting the energy storage device 154, for example, the power bank, to the multi-port hubs 156 and 157. In the open position, the diagnostic computer 114 runs on its internal battery and invokes the software application and the functions of the software application for activating the multi-organ imaging system 118; executing audio/videoconference connections; receiving, creating, recording, processing, storing, and transmitting medical data to a data storage device or a data store via a communication network; and facilitating remote real-time medical examinations. The energy storage device 154 discharges and delivers power, for example, to the multi-port hub 157 for distribution to the multi-organ imaging system 118 whose cable connector is permanently connected to one of the ports 157*a* of the multi-port hub 157. The multi-organ imaging system 118, therefore, receives power from the multi-port hub 157, which allows continuous operation of the multi-organ imaging system 118 during the medical examination.

After completion of the medical examination using the multi-organ imaging system 118, the operator places the multi-organ imaging system 118 back in the corresponding slot 105*f* of the cushioning member 105, deactivates the corresponding illuminating control element 109, and closes the upper shell 102 of the casing 101. When the casing 101 is in the closed position, the disconnection member 112 activates the hubs disconnection switch 144, thereby disconnecting the energy storage device 154 from the multi-port hubs 156 and 157 and preventing the energy storage device 154 from discharging. The energy storage device 154 is recharged from the AC power source via the AC power cord 159 via the multi-port charger 150 when the casing 101 is in the closed position or in the open position. The AC power cord 159 is connected to an AC fused inlet 140 which in turn is connected to an AC inlet port 150*f* of the multi-port charger 150. Furthermore, in an embodiment, when the casing 101 is in the closed position or in the open position, the multi-port charger 150 delivers power to the rechargeable batteries of the clinical examination devices and the accessories, for example, via the magnetic charging connector system 160 exemplarily illustrated in FIGS. 10A-10D and FIGS. 11A-11D, and dedicated cables permanently connected to the power distribution board 152. Therefore, when the casing 101 is in the closed position or the open position and connected to the AC power source, the clinical examination devices and one or more of the accessories receive power from the multi-port charger 150 via the multi-port hubs 156 and 157 and are therefore charged. The medical diagnostic kit 100, therefore, allows closed or open case charging of the internal rechargeable batteries when the AC power source is connected to the AC inlet port 150*f* of the multi-port charger 150 via the AC fused inlet 140. The medical diagnostic kit 100 allows charging to be performed regardless of whether the casing 101 is in the closed position or the open position. Closed case charging is compact space wise and secure. Open case charging is performed, for example, during testing operations. When the energy storage device 154 completely recharged from the AC power source via the multi-port charger 150 in the open position or the closed position, the AC power cord 159 is disconnected, for example, by a technician or other operator of the medical diagnostic kit 100, from the AC fused inlet 140, and the energy storage device 154 is ready for powering the clinical examination devices and the accessories when the casing 101 is in the open position.

For purposes of illustration, an exemplary implementation of the multi-port charger 150, the power distribution board 152, the energy storage device(s) 154, the primary hub 155, and the multi-port hubs 156 and 157 are shown in FIG. 8. However, the scope of the medical diagnostic kit 100 is not limited to the exemplary implementation illustrated in FIG. 8, but may be extended to include alternative implementations of the internal components of the medical diagnostic kit 100. For example, in another exemplary implementation, the multi-port charger 150 is configured as a 60-Watt (W), 10-port AC charger. In another exemplary implementation, the multi-port charger 150 is configured as a 100-Watt, 8-port USB rapid charger. In another exemplary implementation, the hubs 155, 156, and 157 are configured as 4-port switchable 3.0 hubs, each comprising four USB-A ports, a power delivery port, and a USB 3.0 port. In another exemplary implementation, the hubs 155, 156, and 157 are split with 2.0 and 3.0 USB specifications according to the class of clinical examination devices connected thereto. Furthermore, USB ports of different types, for example, type A, type C, etc., for optimal charging and data communication are configured in the various components of the medical diagnostic kit 100.

Figure 9:
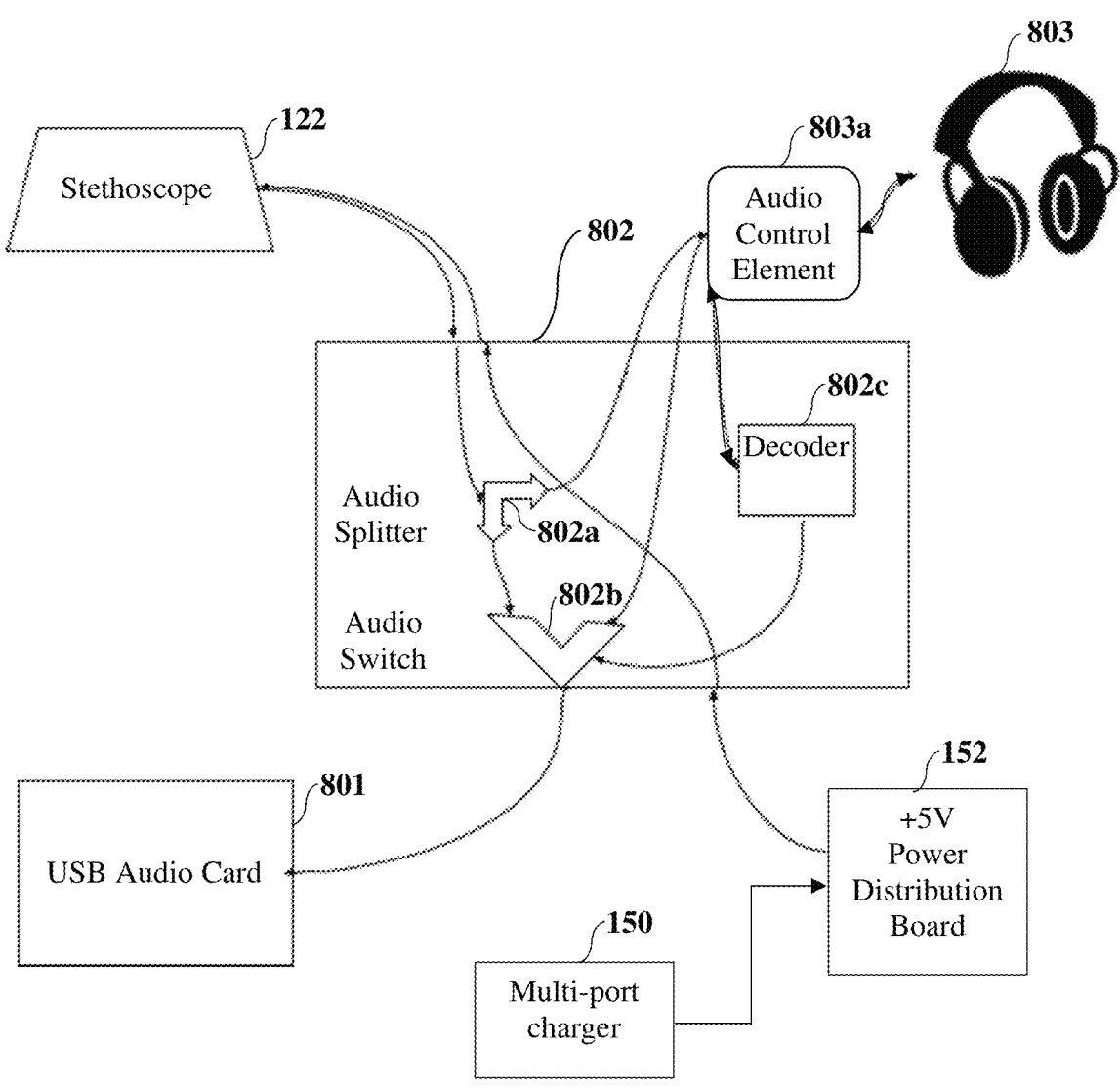
FIG. 9 exemplarily illustrates a block diagram showing an implementation of a stethoscope interface component in an embodiment of the medical diagnostic kit.
Figure 10A:
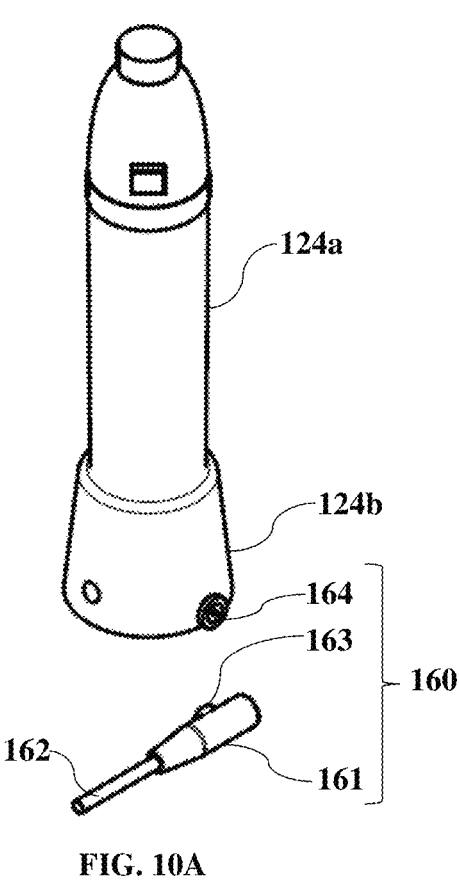
FIGS. 10A-10D exemplarily illustrate different views of a magnetic charging connector system implemented with an accessory of a clinical examination device for quick removal of the accessory from the medical diagnostic kit.
Figure 10B:
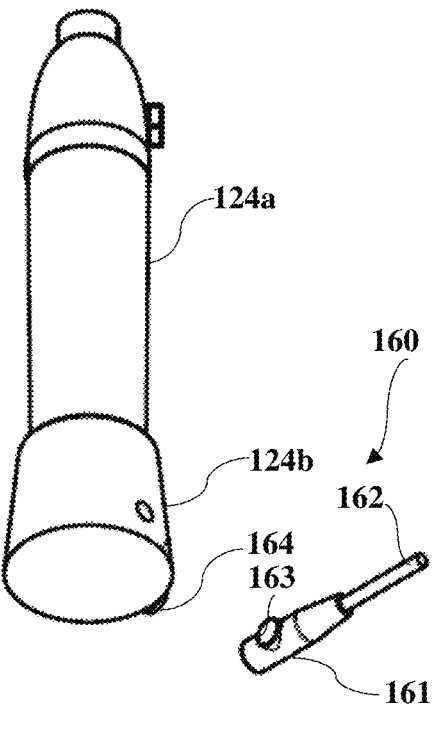
Figure 10C:
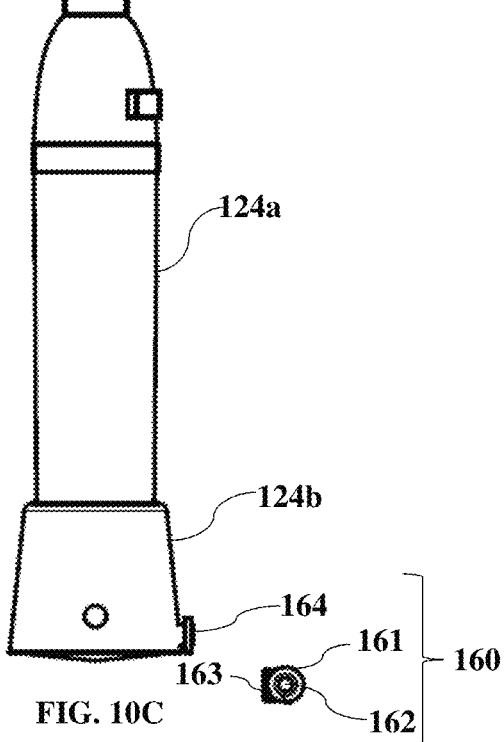
Figure 10D:
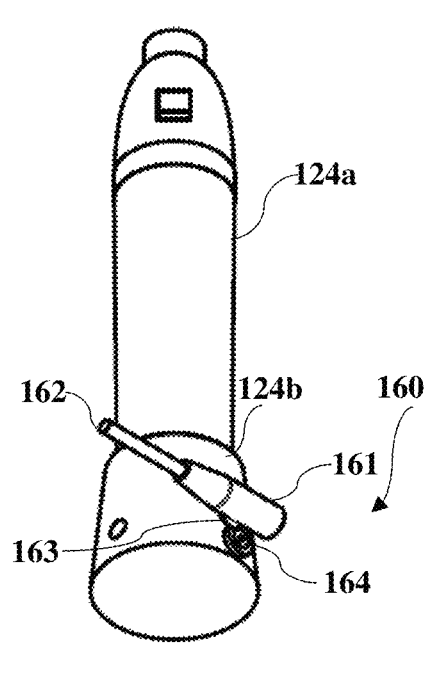
Figure 11A:
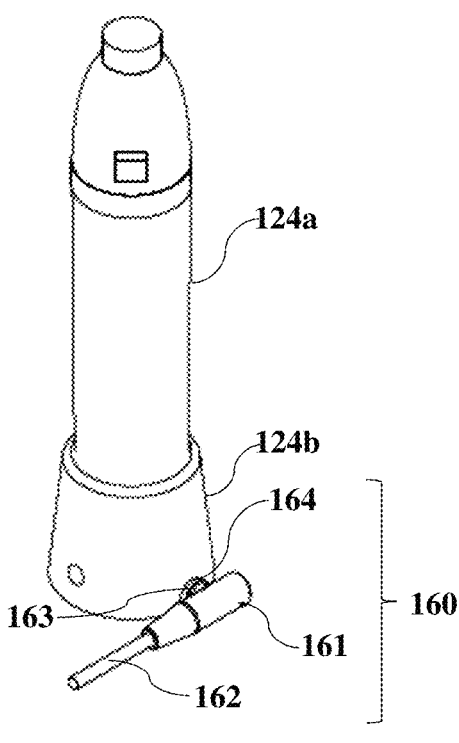
FIGS. 11A-11D exemplarily illustrate different views of the magnetic charging connector system implemented with an accessory of a clinical examination device for quick stowage of the accessory in the medical diagnostic kit.
Figure 11B:
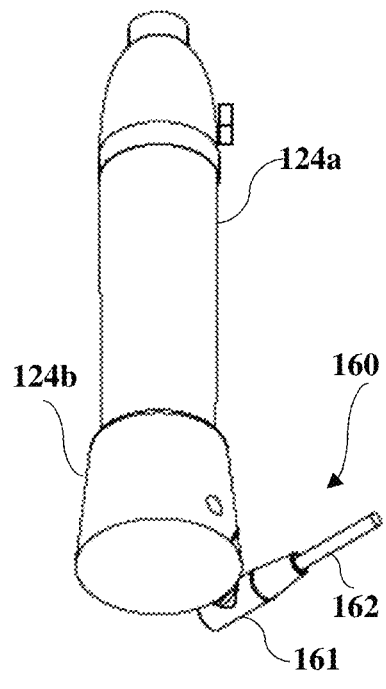
Figure 11C:
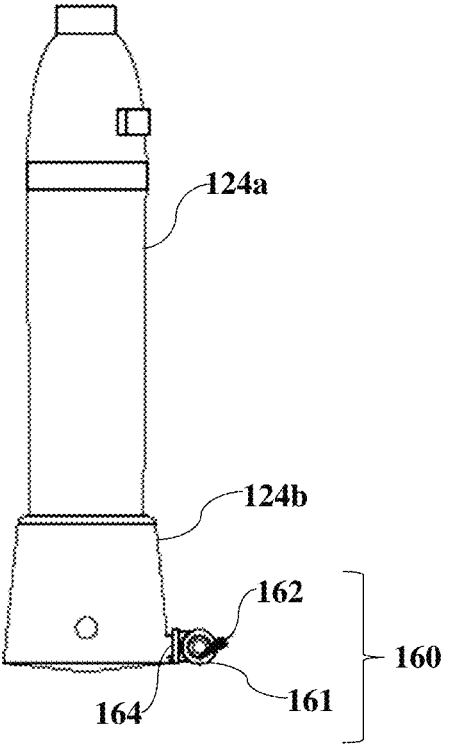
Figure 11D:
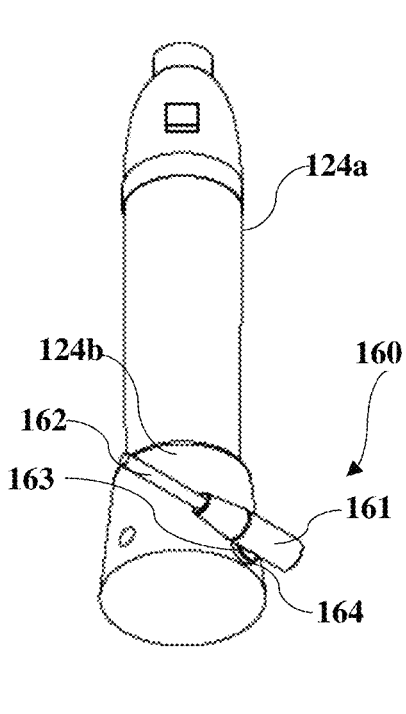

FIG. 9 exemplarily illustrates a block diagram showing an implementation of the stethoscope interface component 802 in an embodiment of the medical diagnostic kit 100 shown in FIG. 1. In an embodiment, the stethoscope interface component 802 in the medical diagnostic kit 100 is operably coupled to a switchable port, for example, 156*a*, of one of the multi-port hubs, for example, 156, via an audio card 801 exemplarily illustrated in FIG. 8, for executing a remote auscultation using a stethoscope 122. In an embodiment, the stethoscope 122 is accommodated in one of the cutouts, for example, 131*e*, on the deck 130 exemplarily illustrated in FIG. 3, or in one of the slots, for example, 105*d*, of the cushioning member 105 exemplarily illustrated in FIG. 1. The stethoscope 122 is, for example, a digital or electronic stethoscope such as the Thinklabs® One digital stethoscope of Thinklabs Medical LLC, configured to provide live sounds to a remote computing device (not shown) of a remote health care practitioner. The audio card 801 is, for example, a universal serial bus (USB) sound card such as the Sound Blaster PLAY! 3 USB digital-to-analog converter (DAC), amplifier (Amp), and external sound card of Creative Technology Ltd. The power distribution board 152 exemplarily illustrated in FIG. 8, distributes power received from the multi-port charger 150 to the stethoscope interface component 802 as disclosed in the detailed description of FIG. 8, for allowing implementation of the stethoscope 122 in the medical diagnostic kit 100. During an alternating current (AC) charging operation, the internal battery of the stethoscope 122 is charged from the stethoscope interface component 802 by the multi-port charger 150 via the power distribution board 152 within the casing 101, without having to remove the stethoscope 122 from the casing 101 and connect to an external charger with a particular charging cable provided by a manufacturer. The stethoscope interface component 802 connects to one of the USB-A ports 156a of the multi-port hub 156 via the audio card 801 as exemplarily illustrated in FIG. 8. The stethoscope interface component 802, therefore, facilitates charging of the stethoscope 122 when the casing 101 is connected to the AC power source via the AC power cord 159.

In an embodiment as exemplarily illustrated in FIG. 9, the stethoscope interface component 802 comprises an audio splitter 802a, an audio switch 802b, and a decoder 802c. The audio splitter 802a is operably coupled to the stethoscope 122 for receiving a stethoscope signal from the stethoscope 122 during a remote auscultation and splitting the stethoscope signal equally into a first audio signal and a second audio signal. The audio splitter 802a transmits the first audio signal to a headset 803, for example, mobile phone earbuds, connected to a headset jack 111 on the console 108 or to another mounting location or holder in the casing 101 via a cable exemplarily illustrated in FIG. 1. An operator of the medical diagnostic kit 100, for example, a technician or an onsite care coordinator (OCC), hears internal body sounds from the first audio signal through the headset 803. The headset 803 comprises a microphone (not shown) and an audio control element 803a. The audio control element 803a is configured, for example, as an audio control button, to control transmission of a microphone signal from the headset 803 to the audio card 801 via the audio switch 802b. The microphone signal provides voice data spoken by the onsite operator into the microphone of the headset 803.

The audio splitter 802a transmits the second audio signal to the audio card 801 via the audio switch 802b. The audio splitter 802a, therefore, routes the stethoscope signal to the audio card 801 and in parallel to the headset 803 of the onsite operator of the medical diagnostic kit 100. The audio card 801 is configured to transmit the second audio signal to the remote computing device of the remote health care practitioner via the diagnostic computer 114 exemplarily illustrated in FIG. 1 and FIG. 8. The audio switch 802b is configured by default to switch an audio card input to the second audio signal provided by the audio splitter 802a. The audio switch 802b is further configured to select between the second audio signal and the microphone signal received from the headset 803 for transmission to the audio card 801. The audio switch output is configured to transmit either the second audio signal or the microphone signal to the audio card 801. Accordingly, an audio/videoconferencing software application operating in the diagnostic computer 114 receives either the second audio signal or the microphone signal from the audio card 801 for transmission to the remote computing device.

The audio switch output is connected to the audio card 801 to allow the audio/videoconferencing software application deployed on the diagnostic computer 114 to receive either the second audio signal or the microphone signal from the audio card 801 for transmission to the remote computing device. The onsite operator switches the audio/videoconferencing software application deployed in the diagnostic computer 114 to the audio card 801 to transmit the second audio signal or the microphone signal to the remote computing device. The diagnostic computer 114 runs the audio/videoconferencing software application and passes the second audio signal or the microphone signal to the remote computing device of the remote health care practitioner.

The decoder 802c is operably coupled to the audio control element 803a of the headset 803. The decoder 802c is configured to decode a control signal received from the audio control element 803a and operate the audio switch 802b. In an embodiment, the audio control element 803a is a push-to-talk (PTT) switch on the headset 803 configured to allow the onsite operator to select to transmit either the stethoscope signal or a voice signal of the onsite operator performing the auscultation to the remote computing device of the remote health care practitioner to establish a rapport with the remote health care practitioner. The voice signal is herein referred to as the "microphone signal". In an example, a pressing action on the audio control element 803a by the onsite operator indicates selection of the microphone signal for transmission to the audio card 801. When the onsite operator presses the audio control element 803a, the decoder 802c decodes the control signal received from the audio control element 803a and transmits the microphone signal from the headset 803 to the audio card 801 via the audio switch 802b.

In an embodiment, the audio card 801 that is connected to the multi-port hub 156 interfaces with the diagnostic computer 114, which communicates with the remote computing device of the remote health care practitioner via a communication network, for example, the internet. The stethoscope 122 is configured to communicate with one or more of the computing devices, for example, the diagnostic computer 114 exemplarily illustrated in FIG. 1 and FIG. 8, via the stethoscope interface component 802. The stethoscope interface component 802 receives power from the multi-port hub 156 when the port 156a is energized with the respective illuminating control element 109 exemplarily illustrated in FIG. 8, thereby energizing internal circuits and the audio card 801. The decoder 802c monitors microphone bias voltage on the headset 803 to detect a pressing action on the audio control element 803a. In an exemplary implementation, the microphone bias voltage drops to zero when the pressing action on the audio control element 803a is produced. The onsite operator selects an audio card channel on the diagnostic computer 114 during auscultation using the audio/videoconferencing software application. The onsite operator operates two switches, one which is operated by the audio control element 803a of the headset 803 during auscultation, and another positioned in the diagnostic computer 114 to switch the audio/videoconferencing input from a conference microphone of the diagnostic computer 114 to the audio card 801 for the auscultation session. After auscultation, the onsite operator switches the audio/videoconferencing input back to the conference microphone of the diagnostic computer 114.

When the casing 101 of the medical diagnostic kit 100 is connected to the AC power source via the AC power cord 159 exemplarily illustrated in FIG. 8, the multi-port charger 150 generates, for example, about +5 Volts (V) of direct current to charge the stowed stethoscope 122, for example, using a standard audio 3.5 mm, tip-ring-ring-sleeve (TRRS) audio cable, via the power distribution board 152 and the stethoscope interface component 802. To execute an auscultation during a remote medical examination with a remote health care practitioner, for example, a physician, an onsite operator of the medical diagnostic kit 100 such as an onsite care coordinator (OCC) opens the casing 101, starts the diagnostic computer 114, connects the headset 803 having the audio control element 803a to the headset jack 111 on the console 108 or another mounting location, via a cable, and removes the stethoscope 122 from the slot 105d of the cushioning member 105 in the casing 101 exemplarily illustrated in FIG. 1. The headset jack 111 is a single audio port in the console 108 or other mounting location for connecting the headset 803 having the audio control element 803a. The audio control element 803a allows selection of the second audio signal, that is, the stethoscope signal, or the microphone signal to be transmitted to the audio card 801. The audio/videoconferencing software application running on the diagnostic computer 114 comprises an internal conferencing microphone and audio card input. For the auscultation procedure, the OCC selects the audio card input on the diagnostic computer 114 and after the auscultation, the OCC selects the internal conferencing microphone to communicate with the patient.

The OCC then places a chest piece with a diaphragm of the stethoscope 122 against a patient's skin to listen to internal body sounds through the headset 803. The chest piece of the stethoscope 122 transmits a stethoscope signal comprising the internal body sounds, to the stethoscope interface component 802. The OCC switches the main audio card input of the audio/videoconferencing software application on the diagnostic computer 114 to the secondary USB audio card 801 to send the stethoscope signal to the remote computing device of the physician. During auscultation, the stethoscope signal splits to the headset 803 and the audio card 801. The OCC hears the quality of the internal body sounds, for example, a heartbeat and lung sounds, and adjusts the position and settings of the stethoscope 122 to achieve an optimal signal-to-noise ratio. When the physician's audio channel is switched to receive the stethoscope signal by the OCC, the physician will not be able to hear the voice of the OCC or the patient, but if needed, the OCC may press the audio control element 803a and talk to the physician. The physician's voice will be heard by the OCC and the patient during the entire auscultation procedure.

To achieve optimal manual switching without performing cumbersome audio channel selection operations on the diagnostic computer 114, the operator uses the audio control element 803a of the headset 803. The operator uses the audio control element 803a to switch between the stethoscope output and a microphone output of the headset 803. The decoder 802c decodes the operator's pressing action on the audio control element 803a and operates the audio switch 802b connecting either the second audio signal of the stethoscope signal or the microphone signal from the operator's headset 803 to the audio card 801. The operator performs the pressing action, for example, as a "hold-to-talk", or a "push-talk-push", or a "push-talk" action until timeout to switch between inputs. The decoder 802c allows the operator to select for the physician input, either the stethoscope signal or the microphone signal, via the audio switch 802b to provide a verbal communication channel to the physician at the remote site during auscultation. The stethoscope 122 provides an audio signal, for example, a heartbeat signal, binaural to the headset 803 via the audio splitter 802a and to the remote computing device of the physician. Binaural sound improves the perception of the internal body sounds, for example, the heartbeat sound, at the operator's location and the physician's remote site. In an embodiment, the decoder 802c operates on a voltage bias of the headset 803 and operates on power received from the energy storage device(s) 154 via the deactivated, hubs disconnection switch 144 exemplarily illustrated in FIG. 8, through the corresponding switchable port 156a of the multi-port hub 156, when the upper shell 102 of the casing 101 exemplarily illustrated in FIG. 1 is opened and the switchable port 156a is activated by the corresponding illuminating control element 109. In an embodiment, the medical diagnostic kit 100 implements a direct charging circuit from the multi-port charger 150 and the power distribution board 152 for directly charging the stethoscope 122 and the stethoscope interface component 802.

FIGS. 10A-10D exemplarily illustrate different views of a magnetic charging connector system 160 implemented with an accessory, for example, an otoscope illuminator battery 124a, of a clinical examination device, for example, an otoscope 124, for quick removal of the accessory from the medical diagnostic kit 100 shown in FIG. 1. In an embodiment, the medical diagnostic kit 100 implements a quick connect-disconnect mechanism with the clinical examination devices and the accessories for quick removal thereof from the medical diagnostic kit 100 and quick stowage thereof into the medical diagnostic kit 100. In this embodiment, the medical diagnostic kit 100 implements the quick connect-disconnect mechanism using the magnetic charging connector system 160 as exemplarily illustrated in FIGS. 10A-10D and FIGS. 11A-11D. The magnetic charging connector system 160 comprises one or more universal magnetic connectors 161 operably coupled to the multi-port charger 150 via the power distribution board 152 exemplarily illustrated in FIG. 8. The universal magnetic connector(s) 161 is magnetically engageable to one or more of the clinical examination devices and the accessories positioned proximal to the universal magnetic connector(s) 161 to create an electrically conductive relationship therebetween.

Magnetic connecting elements, for example, 164, are operably positioned on battery components, for example, 124a, of one or more of the clinical examination devices and the accessories. The magnetic connecting elements 164 are configured specific to battery charging ports. The magnetic connecting elements 164 on the battery components are configured to magnetically attract and mate with corresponding magnetic connecting elements, for example, 163, of the universal magnetic connectors 161. The battery components of the clinical examination devices and accessories, therefore, receive power from the power distribution board 152 via the universal magnetic connectors 161. In an embodiment, the clinical examination devices and the accessories are connected to the power distribution board 152 for charging using the magnetic charging connector system 160 that allows convenient disconnection when the clinical medical devices and the accessories are removed from their storage positions in the deck 130 exemplarily illustrated in FIG. 3, and allows convenient connection for receiving power from the power distribution board 152 when the clinical medical devices and the accessories are returned for stowage in the deck 130.

Consider an example where an accessory of a clinical examination device that operates with the magnetic charging connector system 160 is an otoscope illuminator battery 124a as exemplarily illustrated in FIGS. 10A-10D and FIGS. 11A-11D. For purposes of illustration, the detailed description refers to the accessory of the clinical examination device that operates with the magnetic charging connector system 160 as being an otoscope illuminator battery 124a; however the scope of the medical diagnostic kit 100 disclosed herein is not limited to the magnetic charging connector system 160 being implemented with only an otoscope illuminator battery 124a, but may be extended to include implementation of the magnetic charging connector system 160 with all clinical examination devices and accessories accommodated in the medical diagnostic kit 100. In an example, the magnetic charging connector system 160 is also implemented with the wireless speaker 123 exemplarily illustrated in FIG. 1, accommodated in the medical diagnostic kit 100. A storage position of the otoscope illuminator battery 124a in the medical diagnostic kit 100 is, for example, in a corresponding cutout, for example, 131a, of the deck 130 exemplarily illustrated in FIG. 3, or in a corresponding slot, for example, 105a, of the cushioning member 105 exemplarily illustrated in FIG. 1.

Different views of the magnetic charging connector system 160 implemented with the otoscope illuminator battery 124a for quick removal of the otoscope illuminator battery 124a from the medical diagnostic kit 100 are exemplarily illustrated in FIGS. 10A-10D. As exemplarily illustrated in FIGS. 10A-10D, the magnetic charging connector system 160 comprises a universal magnetic connector 161. The universal magnetic connector 161 is operably coupled to the power distribution board 152 exemplarily illustrated in FIG. 8, via a cable 162. The universal magnetic connector 161 is, for example, a stationary coaxial magnetic connector. In an embodiment, the universal magnetic connector 161 is mounted moderately loose in a corresponding cutout, for example, 131a, of the deck 130 exemplarily illustrated in FIG. 3, or in a corresponding slot, for example, 105a, of the cushioning member 105 exemplarily illustrated in FIG. 1, to have freedom of movement to cling and self-align with a connector section 124b of the otoscope illuminator battery 124a for future charging of the otoscope illuminator battery 124a. The universal magnetic connector 161 comprises a first magnetic connecting element 163 configured to magnetically engage with a second magnetic connecting element 164 operably coupled to the connector section 124b of the otoscope illuminator battery 124a. The first magnetic connecting element 163 and the second magnetic connecting element 164 are a pair of mating elements that magnetically attract each other for implementing a quick connect-disconnect mechanism. In an embodiment, the first magnetic connecting element 163 of the universal magnetic connector 161 protrudes from its storage position. FIGS. 10A-10D exemplarily illustrates the otoscope illuminator battery 124a removed from its storage position, while its magnetic counterpart, that is, the universal magnetic connector 161, remains attached to the storage position, for example, the deck 130. The second magnetic connecting element 164 on the connector section 124b of the otoscope illuminator battery 124a, when in close proximity to the first magnetic connecting element 163 on the universal magnetic connector 161, is configured to magnetically attract the first magnetic connecting element 163 for receiving the power from the power distribution board 152. The power distribution board 152 delivers power received from the multi-port charger 150 to the otoscope illuminator battery 124a via the magnetic charging connector system 160.

FIGS. 11A-11D exemplarily illustrate different views of the magnetic charging connector system 160 implemented with an accessory, for example, the otoscope illuminator battery 124a, for quick stowage of the accessory in the medical diagnostic kit 100 shown in FIG. 1. When the otoscope illuminator battery 124a is brought in close proximity to the universal magnetic connector 161, the first magnetic connecting element 163 on the universal magnetic connector 161 magnetically attracts the second magnetic connecting element 164 on the connector section 124b of the otoscope illuminator battery 124a, thereby connecting the otoscope illuminator battery 124a to the universal magnetic connector 161 as exemplarily illustrated in FIGS. 11A-11D, and allowing quick stowage of the otoscope illuminator battery 124a into its corresponding storage position and charging of the otoscope illuminator battery 124a. To disconnect the otoscope illuminator battery 124a from the universal magnetic connector 161, the otoscope illuminator battery 124a is pulled apart from the universal magnetic connector 161, thereby disengaging the corresponding magnetic connecting elements 164 and 163 as exemplarily illustrated in FIGS. 10A-10D, and allowing quick removal of the otoscope illuminator battery 124a from its corresponding storage position. The magnetic charging connector system 160 provides optimal connect-disconnect operations with battery-driven devices and accessories that need to be taken out of the casing 101 and placed back into the casing 101 during medical examinations.

The magnetic connecting elements 163 and 164 self-align and cling to each other when the universal magnetic connector 161 and the otoscope illuminator battery 124a respectively, are placed in close proximity to each other. When the otoscope illuminator battery 124a is placed firmly into its storage position in the casing 101 with the magnetic connecting element 164 facing its magnetic counterpart, that is, the magnetic connecting element 163 of the universal magnetic connector 161, the magnetic connecting element 163 of the universal magnetic connector 161 is attracted to and self-connects to the magnetic connecting element 164 on the connector section 124b of the otoscope illuminator battery 124a. FIGS. 11A-11D exemplarily illustrates the otoscope illuminator battery 124a magnetically engaged to its magnetic counterpart, that is, the universal magnetic connector 161, while being stowed in its storage position. When the otoscope illuminator battery 124a is pulled out of its storage position, magnetic and electrical contacts of the magnetic connecting elements 163 and 164 are mechanically disconnected. In addition to accessories, the magnetic charging connector system 160 is implemented with the clinical examination devices for quick removal and stowage of the clinical examination devices in the medical diagnostic kit 100. The magnetic charging connector system 160 is used for charging the clinical examination devices and the accessories, while allowing convenient disconnection when the clinical examination devices and the accessories are removed from their storage positions in the medical diagnostic kit 100 and allowing connection when the clinical examination devices and the accessories are returned for stowage in the medical diagnostic kit 100.

Figure 12:
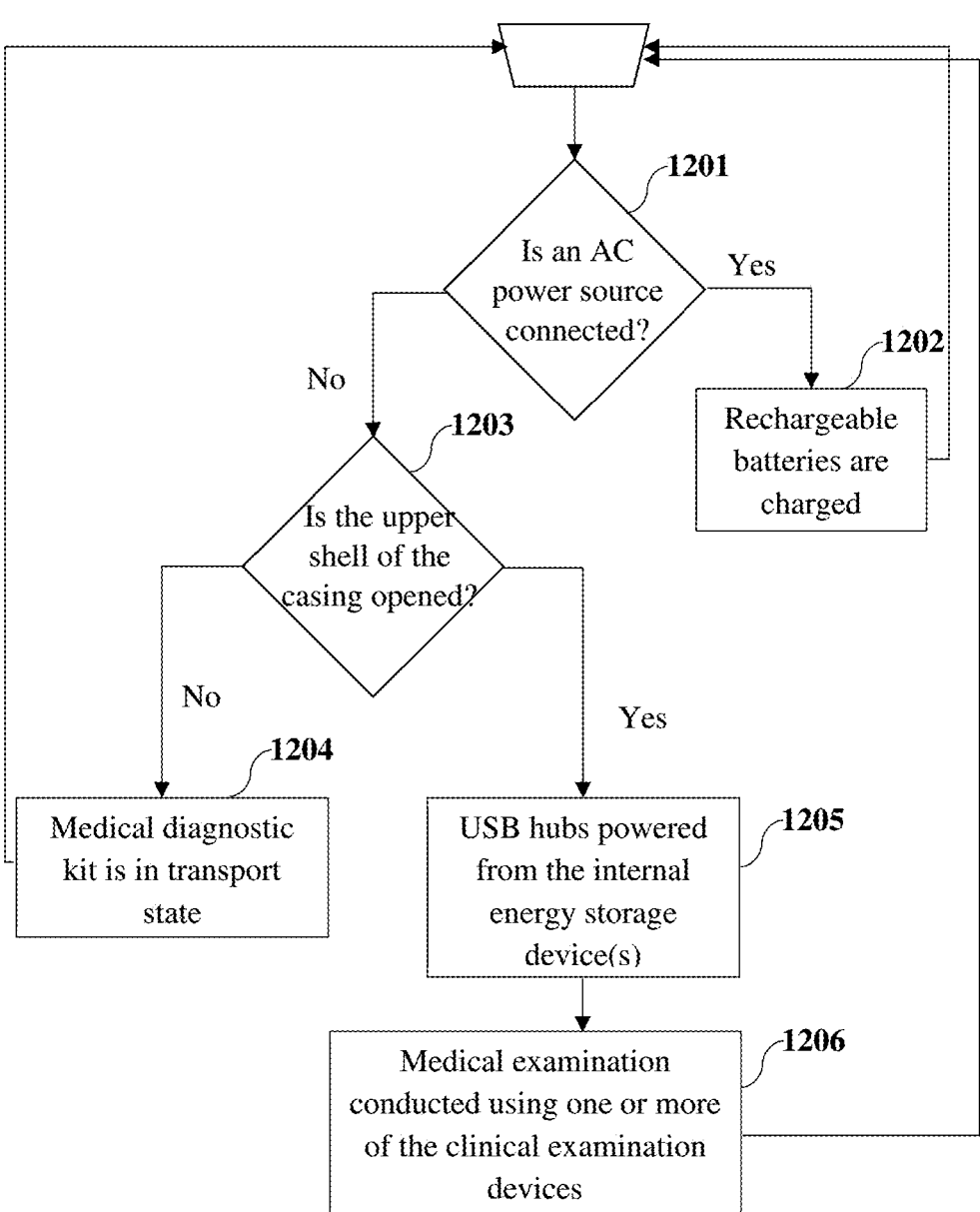
FIG. 12 exemplarily illustrates a flowchart of an embodiment of a method for charging clinical examination devices accommodated in the medical diagnostic kit.

FIG. 12 exemplarily illustrates a flowchart of an embodiment of a method for charging clinical examination devices accommodated in the medical diagnostic kit 100 shown in FIG. 1. An operator of the medical diagnostic kit 100 connects an alternating current (AC) power cord 159 to the multi-port charger 150 via the AC fused inlet 140 exemplarily illustrated in FIG. 8, to initiate charging. If the AC power source is connected 1201, the rechargeable batteries in the medical diagnostic kit 100, for example, the energy storage device(s) 154 and the rechargeable batteries of the clinical examination devices 118, 147, 119, 120, 121, 124, etc., and the accessories exemplarily illustrated in FIG. 1 and FIG. 8, are charged 1202 via the AC power source connected to the multi-port charger 150 and the power distribution board 152. If the AC power source is not connected 1201 to the multi-port charger 150, and if the upper shell 102 of the casing 101 is opened 1203, the multi-port hubs 156 and 157 are powered 1205 from the energy storage device(s) 154, and the medical examination is conducted 1206 using one or more of the clinical examination devices whose cable connectors are permanently connected to one of the ports 156a and 157a of the multi-port hubs 156 and 157 respectively.

When the casing 101 is connected to the AC power source, the multi-port charger 150 feeds power to the air-cooling fan system 153 via the power distribution board 152, charges the computing devices 114, 115, and 149, and charges the energy storage device 154 exemplarily illustrated in FIG. 8. When the casing 101 is in the open position, the energy storage device 154 delivers the power to the multi-port hubs 156 and 157 exemplarily illustrated in FIG. 8, for powering the clinical examination devices and the accessories. The operator may visually see charging activity on the computing devices 114, 115, and 149, the internal energy storage device 154, and the batteries of the clinical examination devices and the accessories by viewing their respective gauges, charging lights, etc., and assess time needed for a full charge. The operator observes charging lights on the clinical examination devices and the accessories. If there is no charging activity, then the operator adjusts positions of the failed-to-charge clinical examination devices, accessories, and respective cable connectors or magnetic quick-disconnect connectors till charging activity commences, thereby ensuring all components are recharged for a patient visit. The operator then closes the casing 101 to reduce space and protect the contents of the casing 101. If there is a need, AC charging can be done at the patient's location during the visit without affecting functionality of the casing 101 using a local AC connection. The AC inlet connection is a worldwide compatible International Electrotechnical Commission (IEC) standard inlet C14 and only affects the external detachable power cord 159 exemplarily illustrated in FIG. 8, to a country-specific AC outlet.

If the upper shell 102 of the casing 101 is closed, the medical diagnostic kit 100 is in a transport state 1204 or is ready for charging and can be charged via the AC power source connected to the multi-port charger 150. That is, when the casing 101 is in the closed position, the multi-port charger 150 feeds power to the air-cooling fan system 153, charges the computing devices 114, 115, and 149, and charges the energy storage device 154 and the batteries of the clinical examination devices and the accessories.

Figure 13:
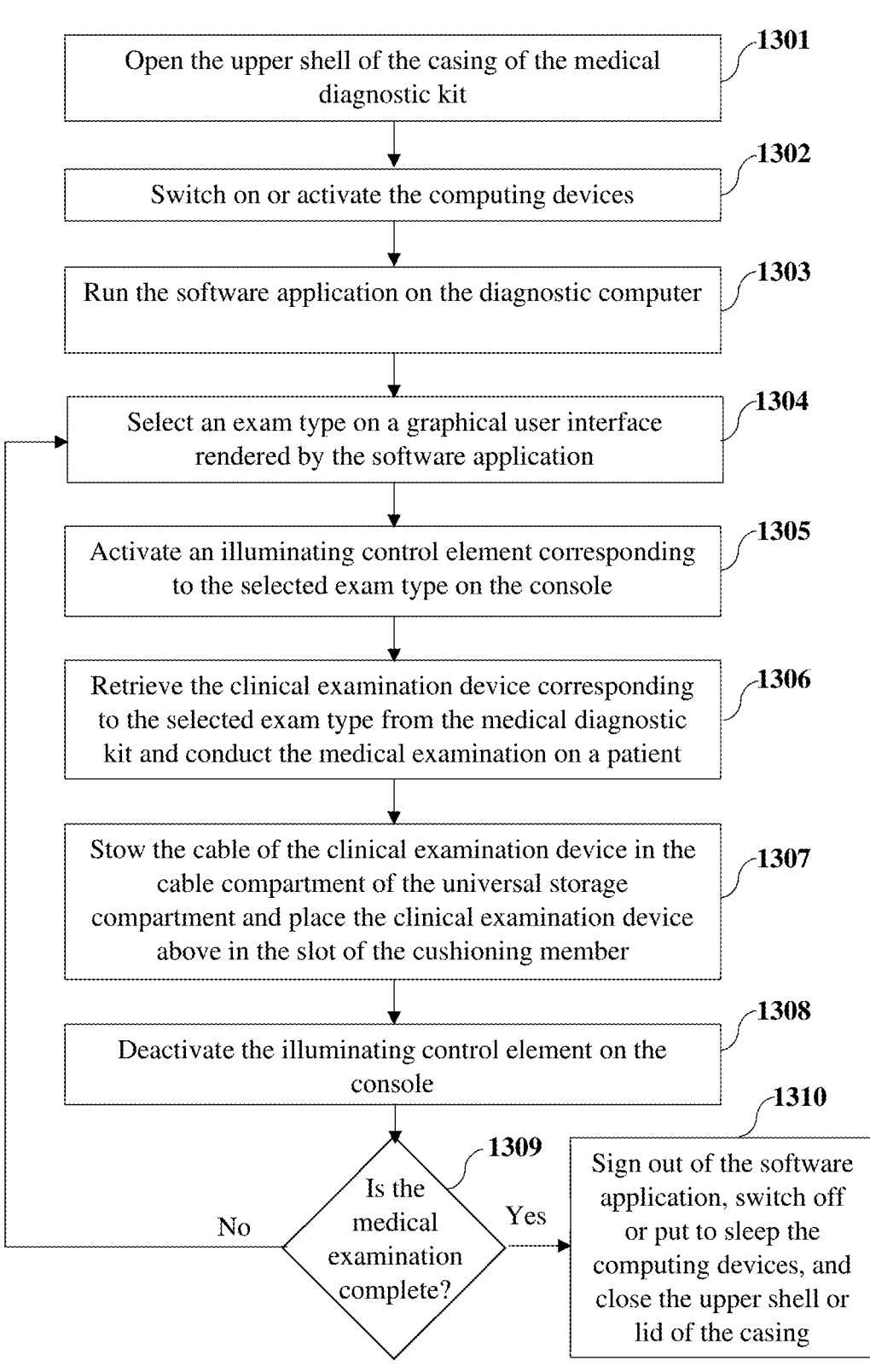
FIG. 13 exemplarily illustrates a flowchart of an embodiment of a method for operating the medical diagnostic kit for performing a medical examination.

FIG. 13 exemplarily illustrates a flowchart of an embodiment of a method for operating the medical diagnostic kit 100 shown in FIG. 1, for performing a medical examination. Consider an example where the medical diagnostic kit 100 is used for facilitating telemedicine, that is, a remote medical examination of a patient by an onsite care coordinator (OCC) acting as a "physician's hands" at the patient's location. The OCC opens 1301 the upper shell 102 of the casing 101 of the medical diagnostic kit 100 and switches on or activates 1302 the computing devices, for example, the network-enabled mobile phone 149 operating as a mobile hotspot, the diagnostic computer 114, and the communication device 115 or tablet computing device exemplarily illustrated in FIG. 8. The diagnostic computer 114 runs 1303 the software application. The OCC selects 1304 an exam type, for example, an ear, nose, and throat (ENT) and skin examination on a graphical user interface (GUI) rendered by the software application. The OCC activates 1305 an illuminating control element 109 or switch corresponding to the selected exam type on the console 108 exemplarily illustrated in FIG. 1. The OCC retrieves 1306 the clinical examination device, for example, 118, corresponding to the selected exam type from the slot 105f in the medical diagnostic kit 100 exemplarily illustrated in FIG. 1, and conducts the medical examination on the patient. The OCC then stows 1307 the cable of the clinical examination device in the cable compartment 129f of the universal cable storage compartment 126 exemplarily illustrated in FIGS. 2-3, and places the clinical examination device 118 above in the slot 105f of the cushioning member 105 exemplarily illustrated in FIG. 1. The OCC then deactivates 1308 the illuminating control element 109 on the console 108. The OCC checks 1309 whether the physician requires further medical examination or whether the medical examination is complete. If the medical examination is complete, the OCC signs out 1310 of the software application on the diagnostic computer 114, switches off or puts to sleep the computing devices 114, 115, etc., and closes the upper shell 102 or lid of the casing 101. If the medical examination is not complete, the OCC proceeds to select 1304 another exam type on the GUI of the software application and repeats the steps 1305 to 1310.

The medical diagnostic kit 100 enables a secure, interactive, two-way, real-time communication between a patient or an onsite operator such as an OCC attending to the patient at the patient's location and a health care practitioner, for example, a physician, at a remote site. The operation of the medical diagnostic kit 100 in telemedicine closes health care gaps over a large geographic area, addresses underutilized physician availability at any location, and attends to underserved patient populations due to scarcity of geographically local physicians. The medical diagnostic kit 100 provides an advanced level of concierge health care and telehealth medicine. The medical diagnostic kit 100 allows health care practitioners reach and periodically monitor patients who have difficulties attending specialist visits, especially patients affected by chronic diseases, who require continuous follow-up. The software application deployed on the diagnostic computer 114 receives, creates, processes, stores, and transmits medical data to a data storage device or a data store via a communication network, thereby providing access of records to different health care practitioners and therefore, allowing health care practitioners to diagnose the patient with a complete medical history of the patient. Moreover, the provision for accommodating a network-enabled mobile phone 149 configured as a mobile hotspot in the medical diagnostic kit 100 provides reliable and uninterrupted access to a wireless communication network at the patient's location, thereby aiding in performing continuous and comprehensive medical examinations of the patient.

Furthermore, the optimal and orderly arrangement for placement and attachment of the clinical examination devices, the accessories, the computing devices 114, 115, and 149, and their cables without mutual entanglement in the medical diagnostic kit 100 improves accessibility and aids in the effective use, handling, and management of tools, devices, equipment, and digital applications at the patient's location, thereby aiding a remote health care practitioner and an onsite operator in performing a medical examination of the patient. The clinical examination devices are configured with enclosed spaces for maximum sanitation. The medical diagnostic kit 100 provides a dedicated storage compartment 126 for accommodating the cables of the clinical examination devices in an orderly manner to prevent entanglement of the cables. The movable dividers 127 and subdividers 128 of the universal cable storage compartment 126 create configurable cable compartments 129a, 129b, 129c, etc., exemplarily illustrated in FIGS. 2-3, for accommodating cables of clinical examination devices of different types, configurations, and future variants therewithin.

The medical diagnostic kit 100 provides a flexible layout that allows accommodation of new instruments or clinical examination devices and their future variants by allowing replacement of a minimal number of layers, for example, the universal cable storage compartment 126 being reconfigurable with movable dividers 127 and subdividers 128 exemplarily illustrated in FIG. 2, the deck 130 exemplarily illustrated in FIG. 3, and the cushioning member 105 exemplarily illustrated in FIG. 1. Furthermore, the medical diagnostic kit 100 comprises complementary computing and communication devices 114, 115, and 149 organized therewithin that adequately facilitate remote real-time medical examinations, provide access to a reliable communication network, operate with the clinical examination devices for enhanced visualization of organs of the patient, and generate, process, and store medical data during the medical examination for future use, diagnosis, and continuous follow-up. The computing devices 114, 115, and 149 and other accessories, for example, the headset 803 exemplarily illustrated in FIG. 9, a wireless speaker 123 exemplarily illustrated in FIG. 1, etc., accommodated in the medical diagnostic kit 100 improve the two-way communication with a remote health care practitioner, for example, during auscultation, and improve verbal communication with a patient. The medical diagnostic kit 100 provides for convenient assembly and testing as the console 108 and the air-cooling fan system 153 comprising the exhaust and intake fans are all accommodated in the universal cable compartment 126. The whole assembly comprising the console 108, the universal cable storage compartment 126, the deck 130, and the air-cooling fan system 153 is mounted in the lower shell 103 of the casing 101 using few fasteners, for example, screws. The medical diagnostic kit 100 implements forced air cooling through the air-cooling fan system 153 to optimize charging time of the energy storage device(s) 154 when the casing 101 is in the closed position.

Furthermore, the hubs disconnection switch 144 that interrupts delivery of power from the energy storage device(s) 154 exemplarily illustrated in FIG. 8, allows the medical diagnostic kit 100 to be transported in a closed position without the energy storage device(s) 154 being discharged, thereby saving battery power when the clinical examination devices are not in use. The medical diagnostic kit 100 also saves battery power by allowing selectively activation of only the required clinical examination device according to a diagnostic scenario and by disconnecting the energy storage device(s) 154 when the medical diagnostic kit 100 is in a closed position and is being transported. Furthermore, the medical diagnostic kit 100 further comprises built-in multi-port hubs 156 and 157 configured to permanently connect to the clinical examination devices and accessories by individual cable connectors for selectively powering and communicating data with the rechargeable battery-containing clinical examination devices and accessories, thereby improving maintenance operations and protecting expensive clinical examination devices. The multi-port charger 150 and the power distribution board 152 connect to the rechargeable battery-containing devices by individual cable connectors for charging when the medical diagnostic kit 100 is connected to an external AC power source. The cable connectors, for example, the USB cable connectors, of the clinical examination devices are permanently attached to the built-in multi-port hubs 156 and 157 at all times until maintenance. Furthermore, the magnetic charging connector system 160 exemplarily illustrated in FIGS. 10A-10D and FIGS. 11A-11D, provides for in-casing charging and easy reconnect when the clinical examination device or accessory is returned to its storage position in the casing 101, thereby improving field operations. The medical diagnostic kit 100 allows the clinical examination devices and the accessories to be charged inside the casing 101 using the magnetic charging connector system 160 without having to remove the clinical examination devices and the accessories from the casing 101 and change their cables.

The medical diagnostic kit 100 allows charging of the energy storage device(s) 154 with a closed or open casing 101. The in-casing charging of the medical diagnostic kit 100 with forced air cooling of the rechargeable batteries of, for example, the computing devices 114, 115, and 149, the clinical examination devices, and the accessories allows all the connected devices to securely charge in a shorter time. The ability to charge the battery-driven internal components in the closed casing 101 improves field operations and protects the expensive computing devices 114, 115, and 149 and clinical examination devices accommodated therein. The casing 101 of the medical diagnostic kit 100 is equipped with the air-cooling fan system 153 exemplarily illustrated in FIG. 8, to prevent the energy storage device(s) 154 and other internal rechargeable batteries from overheating during charging when the casing 101 is in the closed position. The secondary camera 147 provided in the medical diagnostic kit 100 allows a remote health care practitioner to view a patient who may not be in the field of view of a camera of the diagnostic computer 114 being used for videoconferencing during the remote medical examination. The medical diagnostic kit 100 facilitates interactive medicine, also known as live telemedicine, thereby allowing patients and physicians to communicate in real time while also maintaining Health Insurance Portability and Accountability Act (HIPAA) compliance.

The medical diagnostic kit 100 allows onsite application of diagnostic tools, that is, the clinical examination devices, in a house call environment at a patient's home, where a health care practitioner, for example, a physician, at a remote site conducts a remote medical examination of the patient. The medical diagnostic kit 100 allows physicians to remotely examine and prescribe to patients without the patients leaving their homes or apartments. Unlike conventional telemedicine platforms, the medical examinations conducted using the medical diagnostic kit 100 provide physicians with a data-rich experience from the onsite application of hospital-grade diagnostic tools, directed and supervised by the physicians in real time. The enhanced medical examination capability provided by the medical diagnostic kit 100 ensures the continued examination and treatment of, for example, non-COVID-19-related illnesses, particularly among vulnerable patient populations such as the elderly or immune-compromised, who would otherwise avoid or defer care as a result of self-isolation during the coronavirus pandemic. The medical diagnostic kit 100 also allows for continued services from physicians who are temporarily barred from delivering in-person care, due to the need to self-quarantine following COVID-19 exposure or infection.

In a house call scenario, the medical diagnostic kit 100 is deployed, for example, by onsite care coordinators (OCCs) who travel to patients' private homes and apartments, and facilitate patients' appointments with remotely located physicians. At all times during house calls, the OCCs are instructed to wear protective personal equipment and strictly adhere to infection-limiting behavioral protocols, pursuant, for example, to US Centers for Disease Control (CDC) and Prevention and World Health Organization (WHO) guidance. The application of the medical diagnostic kit 100 provides increased cost-effectiveness and process efficiency by allowing the patient visit to be conducted by an onsite medical assistant or a person of higher medical training and licensing as appropriate based on the goal of the medical examination, under continual supervision and direction of a remote physician.

In a nursing home or other congregate care environments, the medical diagnostic kit 100 is utilized on a mobile, patient room-to-patient room basis, by existing end-user medical assistant or facility staff acting as onsite care coordinators (OCCs), to connect with off-site physician support from locations that have insufficient, or non-existent, on-site physician staffing. The application of the medical diagnostic kit 100 reduces the risk of patient-physician cross-infection resulting from direct patient-physician contact, and physicians can efficiently serve multiple patient locations without the need for physician travel.

The medical diagnostic kit 100, being component-based, is adaptable to close care gaps over a large geographic area. If there is underutilized physician availability in a geographic area, the medical diagnostic kit 100 allows that physician resource to be used as long as the physician has access to an internet connection, for example, a satellite internet connection provided by a satellite internet constellation such as the Starlink® internet constellation operated by Space Exploration (SpaceX) Technologies Corporation. If there are underserved patient populations due to scarcity of geographically local physicians, those patients can be served, as long as the medical diagnostic kit 100 has been delivered locally and there is a trained operator for the medical diagnostic kit 100.

Figure 14:
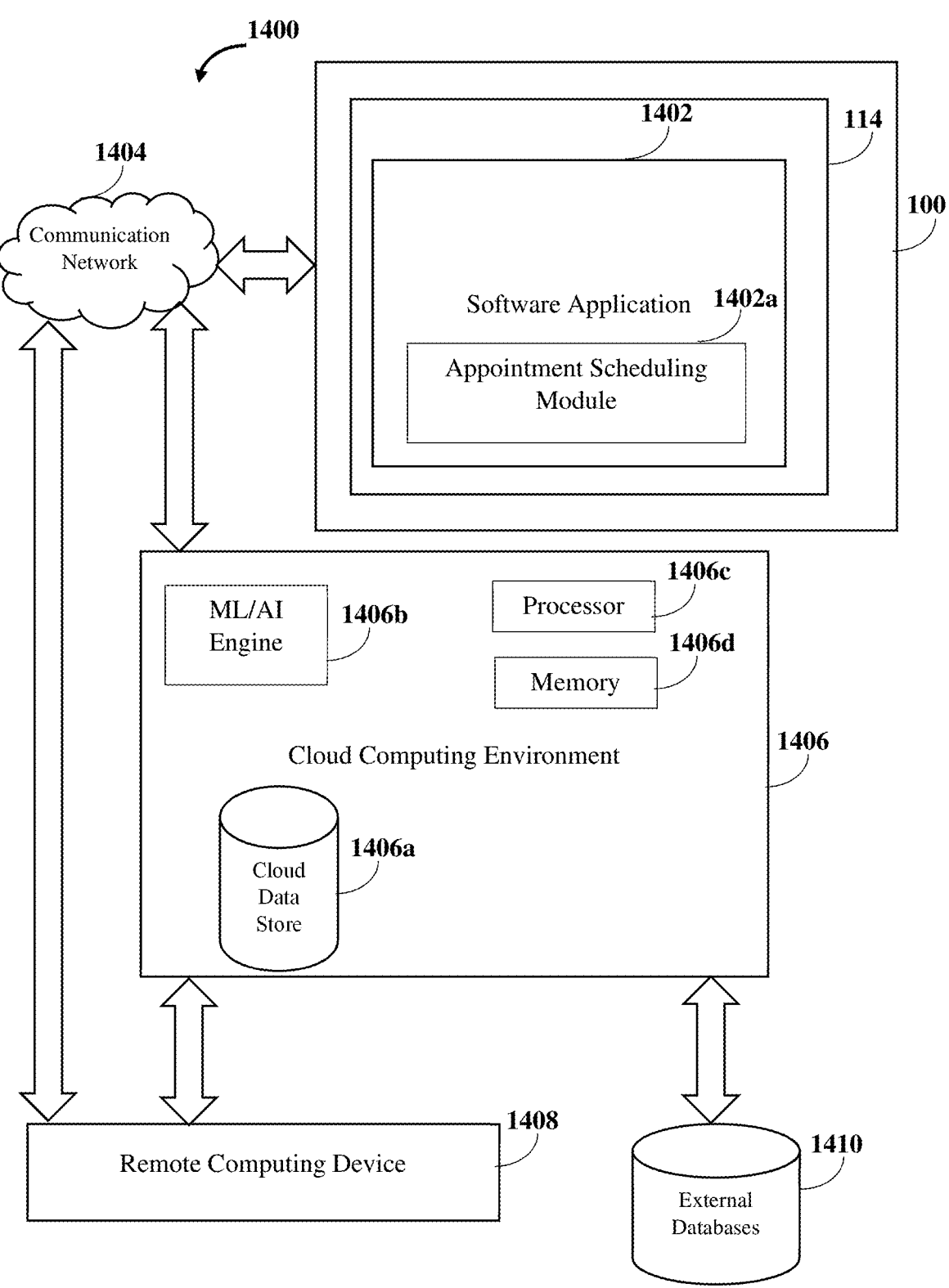
FIG. 14 illustrates a telemedicine system for practicing telemedicine.

FIG. 14 illustrates a telemedicine system 1400 for practicing telemedicine. As illustrated in FIG. 14, the telemedicine system 1400 comprises the medical diagnostic kit 100, the cloud computing environment 1406, and the remote computing device 1408 of the remote health care practitioner, each connected to the communication network 1404. Also, as illustrated in FIG. 14, the software application 1402 is hosted on the diagnostic computer 114 of the medical diagnostic kit 100. In an embodiment, the software application 1402 in the diagnostic computer 114 is configured to integrate a hardware driver of any of the clinical examination devices 118, 147, 119, 120, 121, 124, etc., illustrated in FIGS. 1, 7A and 7B, with the click of a button. The button is either an illuminating control element 109 illustrated in FIG. 1 or a button displayed on the display screen of the diagnostic computer 114. The software application 1402, for example, comprises drivers for integrating any new clinical examination device that is connected to the medical diagnostic kit 100. In an embodiment, the software application 1402 identifies a new clinical examination device that is connected to the medical diagnostic kit 100. When the software application 1402 does not find a matching hardware driver for the new clinical examination device, the software application 1402 is configured to scan a library, for example, a local library or an online library, to determine if a matching hardware driver exists. If a matching hardware driver exists, the matching hardware driver is loaded onto the diagnostic computer 114. The software application 1402 therefore supports changes in hardware of the clinical examination devices, for example, the multi-organ imaging system 118, the electrocardiograph 119, the blood pressure monitor 120, the oximeter 121, the otoscope 124, the secondary camera 147, the stethoscope 122, etc. For example, if a clinical examination device is replaced by another clinical examination device of a different brand, the software application 1402 identifies the replacement clinical examination device and loads the matching hardware driver for the replacement clinical examination device to enable the replacement clinical examination device to function seamlessly.

In an embodiment, the software application 1402 is a Windows application that allows any device, for example, a clinical examination device, connected to the diagnostic computer 114 of the medical diagnostic kit 100, and that provides a display on the diagnostic computer's 114 screen to be "integrated" to the medical diagnostic kit 100. In an embodiment, the software application 1402 integrates clinical examination devices that provide audible and other type of outputs. FIGS. 18A-18G illustrate configuration screens of the various clinical examination devices. In an embodiment, the software application 1402 is configured to display a configuration screen, on the display screen of the diagnostic computer 114 of the medical diagnostic kit 100 to allow for a software administrator, for example, an OCC to add a new instrument or a new clinical examination device. As illustrated inf FIGS. 18A-18G, the OCC selects the new instrument or the new clinical examination device by its registered name in the Windows Registry name, or by supplying the path to the custom hardware driver if the device does not have an installable hardware driver. As shown in FIGS. 18A-18C and 18E-18G, "Path to executable file" refers to the path to the custom hardware driver of the clinical examination device. Either way, the new instrument or the new clinical examination device connected can be initiated from the display screen of the diagnostic computer 114 of the medical diagnostic kit 100 via a dedicated button or via an illuminating control element 109. By default, the settings of the diagnostic computer 114 of the medical diagnostic kit 100 support a standard set of clinical examination devices, for example, the multi-organ imaging system 118, the electrocardiograph 119, the blood pressure monitor 120, the oximeter 121, the otoscope 124, the secondary camera 147, the stethoscope 122, etc. FIGS. 18A-18C and 18E-18G also show a "Path to data folder" where the medical data captured by the clinical examination device is stored. The clinical examination device may also be enabled or disabled using a toggle switch displayed on the display screen of the diagnostic computer 114, as shown in FIGS. 18A-18G.

Figure 15:
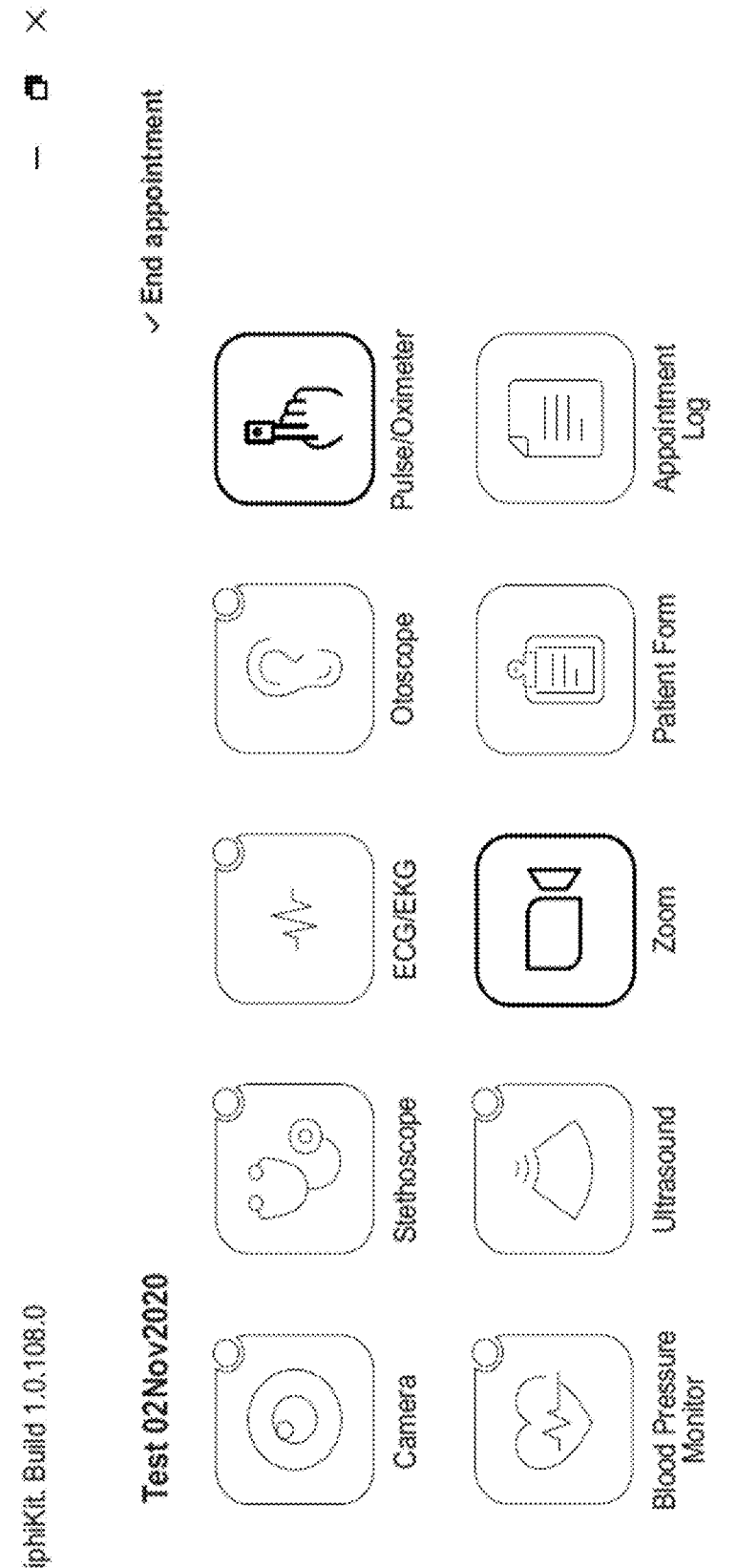
FIGS. 15 and 16 illustrate screenshots of a graphical user interface (GUI) rendered by a software application showing lists of clinical examination devices connected to the medical diagnostic kit.
Figure 16:
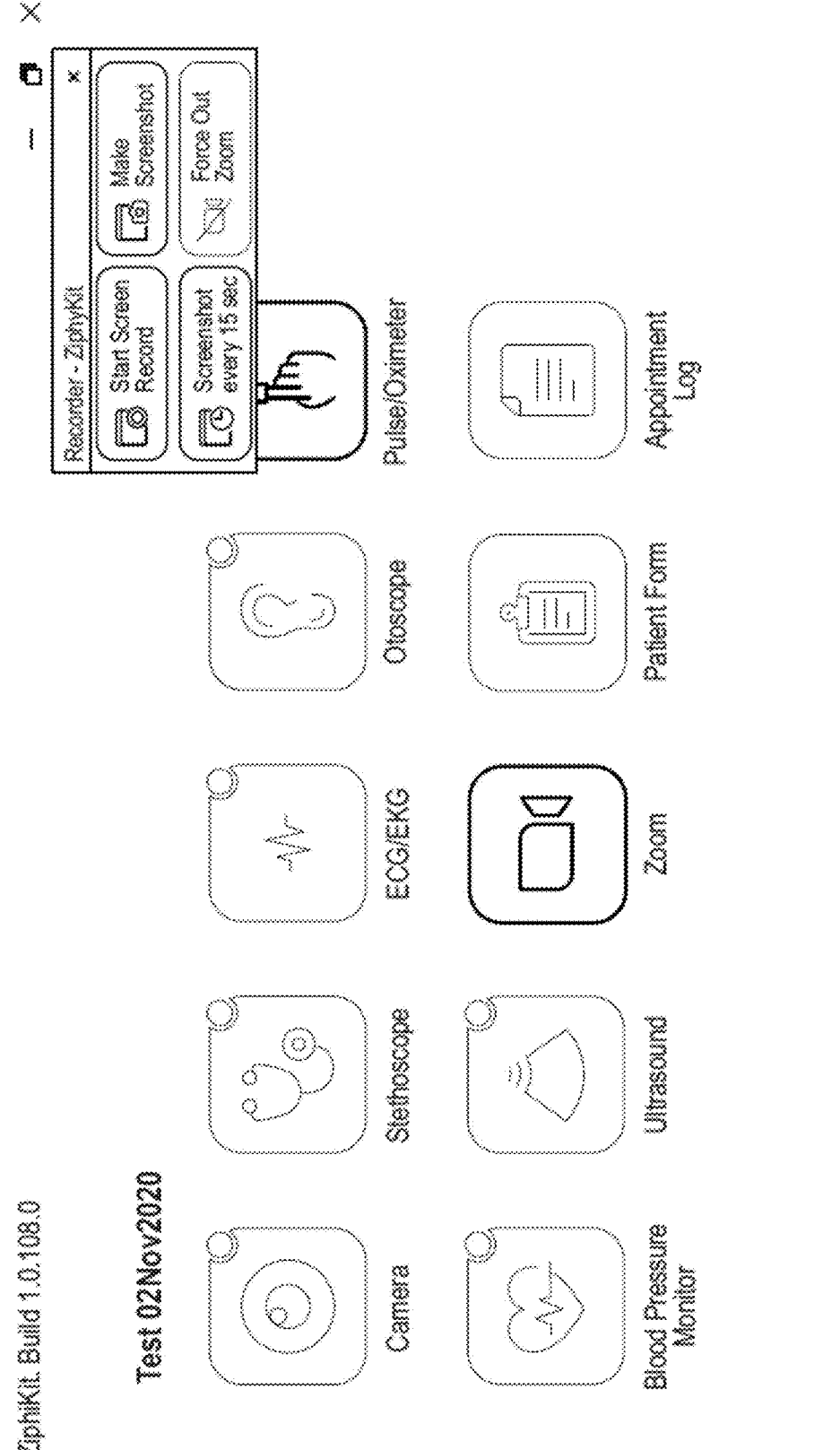
Figure 18C:
Figure 18D:
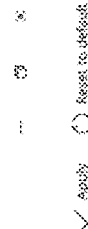
Figure 18D:
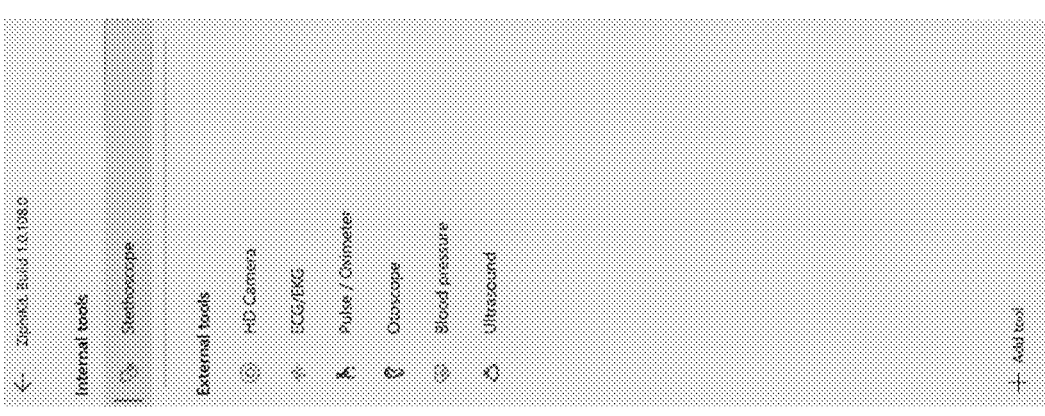
Figure 18E:
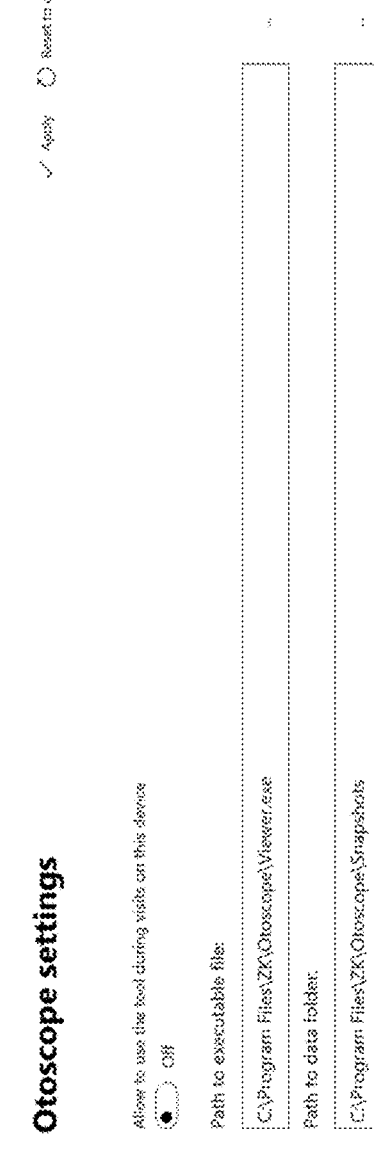

FIGS. 15 and 16 illustrate screenshots of a graphical user interface (GUI) rendered by the software application 1402 showing lists of clinical examination devices connected to the medical diagnostic kit 100. The software application 1402 is configured to provide a visual output of the measurement or reading provided by the clinical examination devices, including the new clinical examination device, on a display of the diagnostic computer 114. Furthermore, as explained earlier, the software application 1402 is configured to receive, create, record, process, store, and securely transmit medical data from the clinical examination device(s) to the remote computer 1408 of the practitioner and to a data store 1406 via a communication network 1404, for example, a wireless communication network. For example, the software application 1402 is configured to take a single screenshot, take screenshots periodicity, or start a continuous recording of the images and/or videos displayed on the display screen of the diagnostic computer 114 and computing device 115 and save them in the cloud data store. As illustrated in FIGS. 15 and 16, the software application 1402 provides buttons on the display screen of the diagnostic computer 114 to allow a user, for example, the OCC to take a single screenshot, take screenshots periodicity, or start a continuous recording of the images and/or videos displayed on the display screen of the diagnostic computer 114 and computing device 115. In an embodiment, the software application 1402 is configured to securely transmit the medical data from the clinical examination device(s) directly to the remote computer 1408 of the practitioner via the communication network 1404. In another embodiment, the software application 1402 is configured to securely transmit the medical data from the clinical examination device(s) to both the cloud data store 1406 and the remote computer 1408 of the practitioner via the communication network 1404.

In an embodiment, the software application 1402 is further capable of encrypting the medical data produced as a result of the data being captured using one or more clinical examination devices, including all audio and video data. FIGS. 15 and 16 also illustrate an appointment log button on the GUI rendered by the software application 1402. In an embodiment, the software application 1402 comprises an appointment scheduling module 1402a, illustrated in FIG. 14. The appointment scheduling module 1402a allows users to create appointments in both a local mode and a live mode. Local Mode allows the clinical examination to take place without having to send the medical data to the cloud data store. Instead, the medical data is stored locally in an encrypted format and the encrypted medical data is configured to be copied into an encrypted external storage device or safely deleted. In an embodiment, the encrypted medical data is uploaded to cloud storage and decrypted at the cloud storage. In another embodiment, the medical data is always stored in an encrypted format on the medical diagnostic kit 100. In an embodiment, the onsite care coordinators (OCCs) who travel to patients' private homes create the appointments through local mode. In an embodiment, the appointments are created by the patients themselves. In the live mode, appointments are booked by a user via the web-based platform provided by software application 1402 in the diagnostic computer 114 or created directly on the medical diagnostic kit by an operator without the user booking it, and the appointments are synchronized with a "Practice storage" in a remote data store, as illustrated in FIG. 14. A remote data store, as used herein, is for example, the cloud data store 1406a shown in FIG. 14. The local mode of appointment can be used for a quick in-field triage where the medical data of a patient must be quickly copied and the medical data cannot be saved to the remote data store as it may not belong to any practice, for example, emergency operation during COVID for popup tent triage. A "Practice Storage" is a HIPAA-complaint file storage secured with appropriate Access Control List (ACL) settings into which the medical data from the live or real-time medical examination of a patient is sent. That medical data is converted into an appropriate format. For example, raw videos in the medical data are converted for viewing in various resolutions, video files and other files in the medical data are encrypted, etc. As used herein, raw video refers to uncompressed original video captured by the secondary camera 147 at the medical diagnostic device 100. Furthermore, links or URLs to the files of the medical data are stored in the cloud data store 1406a and sent to the patients for future viewing. For example, the links or URLs are stored in the electronic health record of a patient. In an embodiment, the links or URLs to the files of the medical data are sent to the remote health care practitioner.

Figure 19:
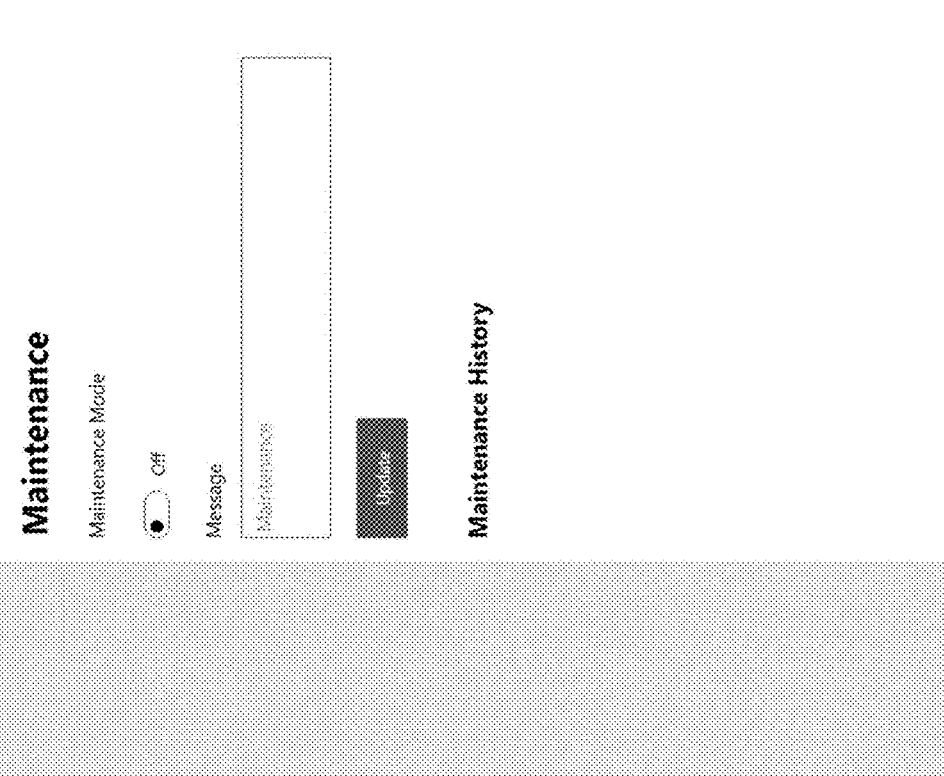
FIG. 19 illustrates a screenshot of the graphical user interface (GUI) rendered by the software application on a display screen of the diagnostic computer showing a button to place the medical diagnostic kit in the maintenance mode.

Furthermore, the software application 1402 is capable of logging all the appointments for support. The software application 1402 is further capable of setting alerts in between the on-site care coordinators (OCCs). Alerts are sent by the software application 1402 to notify the OCCs regarding possible malfunction in the medical diagnostic kit 100. For example, in an ongoing telemedicine session, the software application 1402 sends alerts to the OCC using the medical diagnostic kit 100 about possible malfunctions in the medical diagnostic kit 100. In another embodiment, the software application 1402 sends alerts to the OCC about issues and notes from the previous operator of the medical diagnostic kit 100 with possible remedies. The software application 1402 is further capable of placing the medical diagnostic kit 100 into a maintenance mode. For example, the software application 1402 is programmed to place the medical diagnostic kit 100 into the maintenance mode when one or more of the clinical examination devices of the medical diagnostic kit 100 are replaced, when the software application 1402 is updated, etc. In an embodiment, the user, for example, the OCC can also place the medical diagnostic kit 100 in the maintenance mode with the click of a button. The button is either an illuminating control element 109 illustrated in FIG. 1 or a button displayed on the diagnostic computer 114. FIG. 19 illustrates a screenshot of the graphical user interface (GUI) rendered by the software application 1402 on the display screen of the diagnostic computer 114 showing a button to place the medical diagnostic kit 100 in the maintenance mode. Also, the medical diagnostic kit 100 can be placed in the maintenance mode to avoid using it in the future until it is serviced. A record of defects in the medical diagnostic kit 100, a record of the time instances when the medical diagnostic kit 100 was placed under maintenance, reasons for placing the medical diagnostic kit 100 under maintenance, and repairs and replacement performed during maintenance are all be saved either on the medical diagnostic kit 100 and/or the cloud data store 1406a for the future analysis and for planning capacity utilization the medical diagnostic kit 100.

In an embodiment, medical data and appointment data of a patient are used to produce a bill using the medical diagnostic kit 100 using the recoded medical data, for example, screenshots, audio data and/or video data as supporting document for billing. The bill is either an intermediary bill or a final bill.

Figure 21:
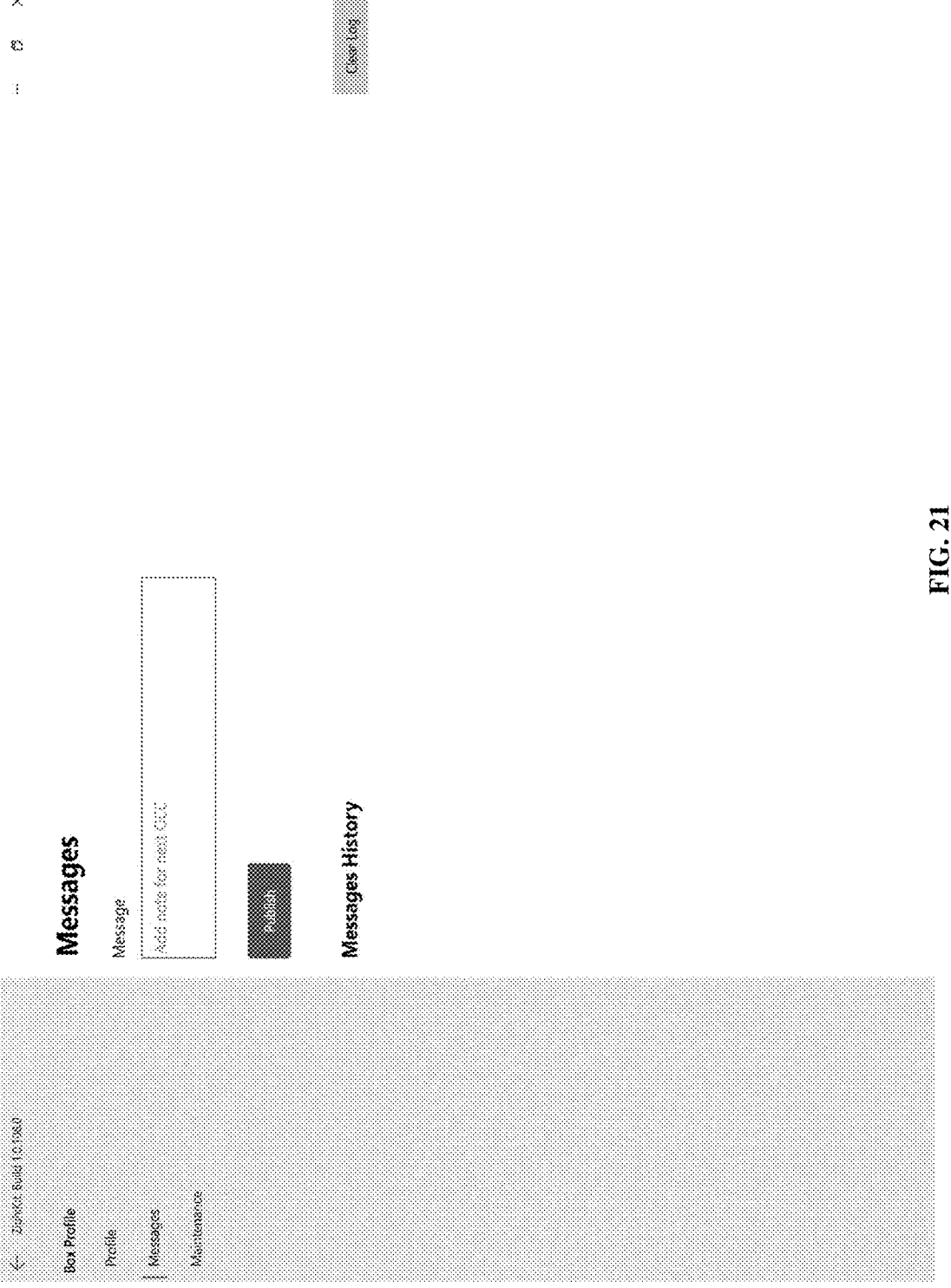
FIG. 21 illustrates a screenshot of the graphical user interface (GUI) rendered by the software application on the diagnostic computer for accessing messages stored in the medical diagnostic kit.

The software application 1402 is further capable of synchronizing the medical data, for example, the data in the medical diagnostic kit 100, in real-time into the cloud data store 1406a. The medical diagnostic kit 100 is configured to synchronize the medical data, for example, the patient's vital signs, sonograms, electrocardiograms (ECGs), auscultation sounds, camera pictures, etc., stored securely in an internal storage device of the medical diagnostic kit 100 with a physician's remote computing device or the remote cloud data store 1406a. In an embodiment, the software application 1402 provides provisions for leaving messages from one operator/user to another operator/user between successive medical examinations. A headset 902 with a microphone exemplarily illustrated in FIG. 9 is used to record audio messages. In an embodiment, a secondary camera 147 exemplarily illustrated in FIGS. 7A-7B is used to record video messages. Furthermore, operators can exchange the messages using the Maintenance options in the medical diagnostic kit 100. An operator can leave a message to the next operator that uses the medical diagnostic kit 100. FIG. 21 illustrates a screenshot of the graphical user interface (GUI) rendered by the software application 1402 on the diagnostic computer 114 for accessing messages stored in the medical diagnostic kit 100.

The software application 1402 is further capable of creating a transaction log that automatically records usage of all clinical examination devices, including the sequence of usage of the clinical examination devices, frequency of usage of each of the clinical examination devices. The software application 1402 is further capable of capturing the timeline of each clinical examination device usage with captured screenshots that can serve as proof for the insurance companies that a medical examination was actually conducted. This feature is very relevant at the present time where telehealth is difficult to regulate. The software application 1402 is further capable of synchronizing medical data of a patient and appointment data with electronic health record of the patient at the physician's remote computing device or the cloud-data store, thereby providing ready access of all files and medical data of the patient to the remote health care practitioner at any point in time. In an embodiment, the medical data is synchronized during the appointment, in case the doctor requires the most updated medical data. In another embodiment, the medical data is synchronized at a later point of time. In an embodiment, upon reaching the count of 10 unsynchronized appointments stored on the medical diagnostic kit 100, the medical diagnostic kit 100 blocks the OCC to use the software application 1402 until the medica data and appointments are synchronized.

Figure 17:
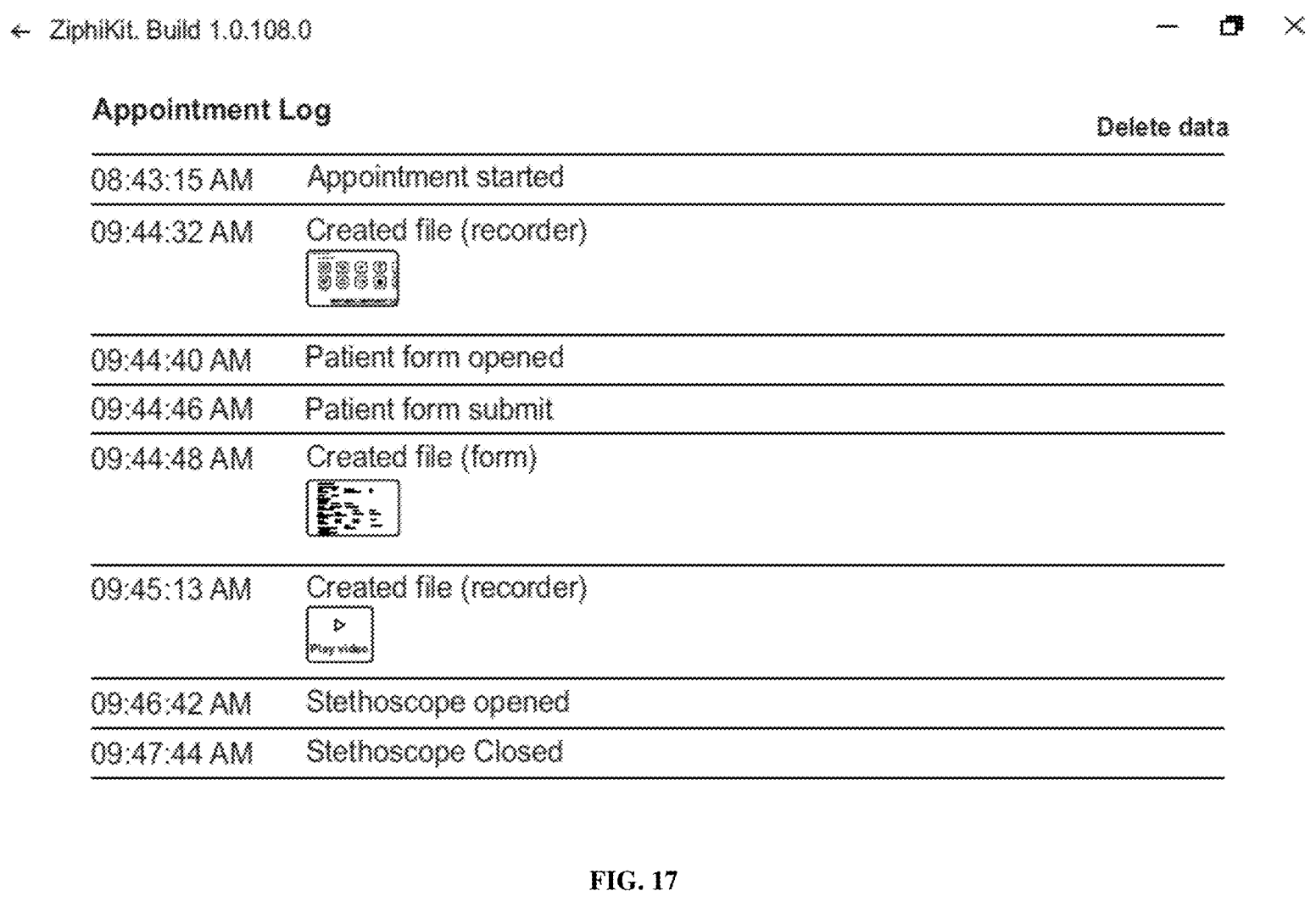

FIG. 17 illustrates an appointment log created by the software application 1402. In an embodiment, using each clinical examination device in an order or using one or more clinical examination devices creates an automatic appointment log in the appointment data of the patient. The appointment log is, for example, a form where events of calling the one or more clinical examination devices are captured along with screenshots and/or video displayed on the display screen of the diagnostic computer 114 and/or the display unit 115a of the communication device 115, corresponding to the clinical examination device in use. The screenshots and/or video displayed on the display screen of the diagnostic computer 114 and/or the display unit 115a of the communication device 115 are configured to be recorded. In an embodiment, the medical diagnostic kit 100 records the medical data from two or more clinical examination devices 118, 147, 119, 120, 121, 124, etc., when that are used simultaneously. The medical diagnostic kit 100 comprises a "recording" panel, illustrated in FIGS. 15 and 16 which allows the OCC of the medical diagnostic kit 100 to initiate recording of either:

a continuous screencast of the medical examination content displayed on the display screen of the diagnostic computer 114 and/or the display unit 115a of the communication device 115;

a single screenshot on button press, or screenshots at intervals of 15 seconds.

In an embodiment, the software application 1402 is further configured to block the usage of the medical diagnostic kit 100 until appointment data is synchronized. In an embodiment, the appointment data is deleted from the diagnostic computer 114 by the software application 1402 after synchronization. The file system in the diagnostic computer 114 places a restriction on the final size of a file, for example, the appointment data and therefore, the diagnostic computer 114 is not used as a permanent storage and instead the medical data, including appointment data, is encrypted and stored in the diagnostic computer 114 only till the medical data reaches the final size. In another embodiment, the medical data is stored in the diagnostic computer 114 for a temporary period of time. Beyond the temporary period of time, the encrypted medical data is synchronized with the medical data on the cloud data store 1406a. At any time during the clinical examination, the local recorded data collected at the medical diagnostic kit 100 can be synchronized with the cloud data store 1406a so that, during a videoconference, if the communication network 1404 connection is not strong enough to produce a video of adequate sharpness for the remote health care practitioner to view, if image resolution is lower compared to the original image, if image on the screen is blurry or pixelated, or if the screen is too small and the remote health care practitioner is required to zoom in. In an embodiment, by maintaining a connection to the communication network 1404, the local recorded data can be pushed into the cloud data store constantly at a frequency which can make this a part of remote monitoring activity. The OCC can switch between various audio/video conference connections treating a number of patients at the same time, resembling a real physical office. If a communication link to the physician's remote computing device is not available, the medical diagnostic kit 100 and the software application 1402 are configured to store medical data, for example, the patient's vital signs, sonograms, electrocardiograms (ECGs), auscultation sounds, camera pictures, etc., securely in an internal storage device for a later upload or an artificial intelligence (AI)-enabled batch upload to the physician's remote computing device, when the communication network 1404 is available.

The medical diagnostic kit 100 provides a user-friendly, web-based platform with an integrated video/audio conference connection enabling remote real-time exams. The medical data recorded during the remote, real-time medical examinations is securely stored electronically for future diagnostic and/or therapeutic use. The software application 1402 and the medical diagnostic kit 100 gather medical data in real-time where the medical data comprises physical exam data and chronic conditions related data. The medical data also comprises audio-visual data from the secondary camera 147, the microphone of the diagnostic computer 114, the microphone signal from the headset 803, etc. The audio-visual data is collected in concert so that the collected data aids a remote healthcare practitioner in effectively diagnosing the patient's condition and not collected just for transmitting the data to the cloud data store. The audio-visual data comprises raw data having video, screencast and audio together to create an effect of the full physical examination. As used herein, raw data, refers to uncompressed original video, audio and/or image data. In embodiment, the software application 1402 utilizes machine learning and/or artificial intelligence in between collecting medical data and reception of medical data at the remote computing device of the remote health care practitioner for enhanced real time diagnostic. The cloud computing environment 1406 utilizes a machine learning/artificial intelligence engine 1406b, herein referred to as ML/AI engine 1406b coupled to a processor 1406c and a memory 1406d, as illustrated in FIG. 14, for analyzing the recorded medical data in real-time automatically through machine learning and artificial intelligence algorithms to diagnose medical conditions and probable patterns of illnesses in a patient. In an embodiment, the machine learning and artificial intelligence algorithms are stored in the cloud data store 1406a. The cloud data store 1406a comprises medical data of a patient along with medical data of other patients. The ML/AI engine 1406b is also linked to external databases 1410 that comprise information of various illnesses. The ML/AI engine 1406b is configured to utilize the machine learning and artificial intelligence algorithms to compare the medical data of a patient against the information in the external databases 1410 to diagnose medical conditions and probable patterns of illnesses in the patient. Information related to the diagnosed medical conditions and probable patterns of illnesses in the patient are relayed in real-time to the physician's remote computing device 1408.

Figure 20:
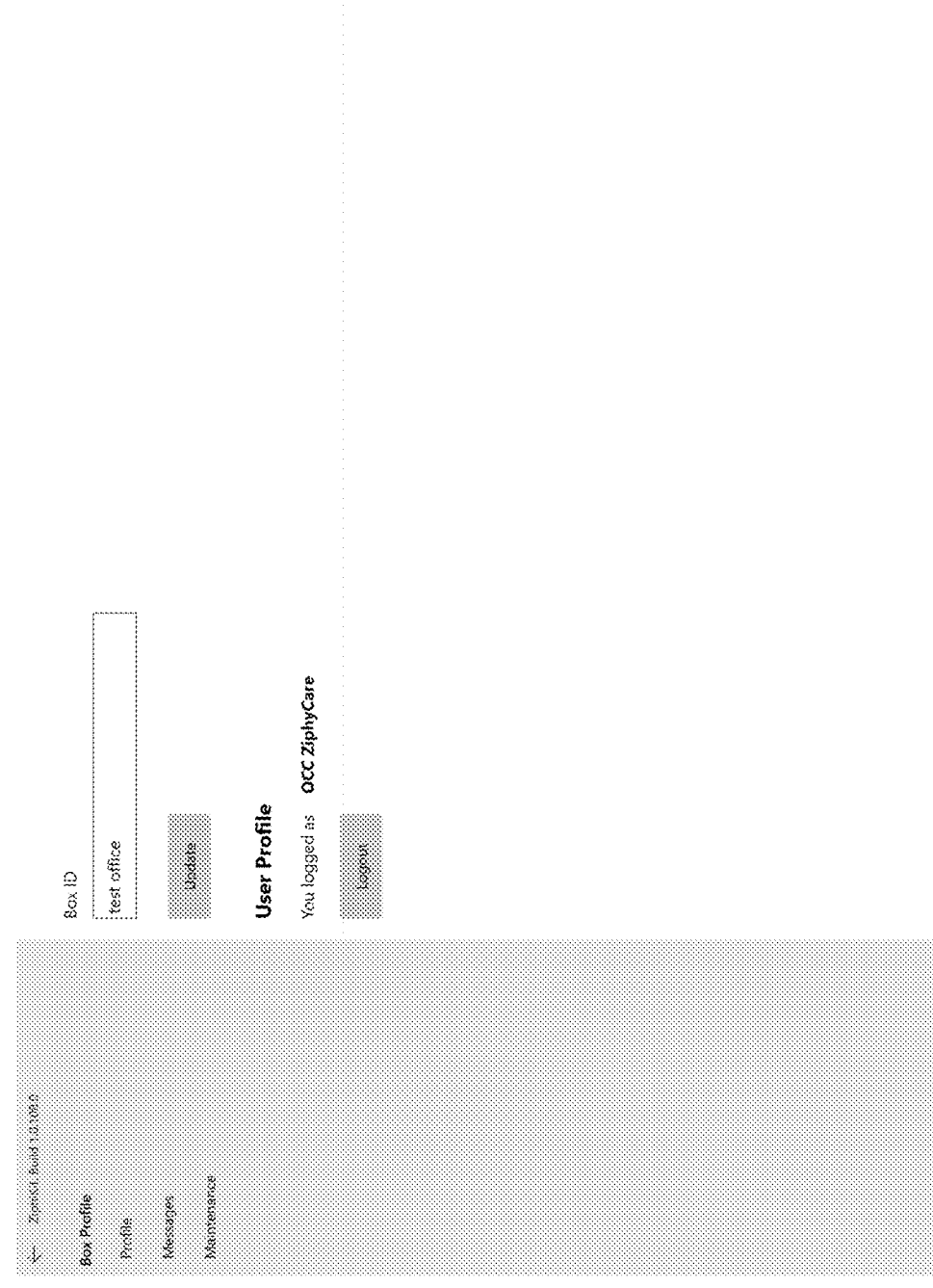
FIG. 20 illustrates a user profile displayed on the display screen of the diagnostic computer after the medical diagnostic kit authenticates the user.

The diagnostic computer 114 allows a user, for example, an operator of the medical diagnostic kit 100, to sign in to the software application 1402 through a restricted user account and rotated password. In an embodiment, the medical diagnostic kit 100 is connected to an application 1402 on the cloud computing environment. The user, for example, an OCC, is automatically authenticated against user data in the Data store of the cloud computing environment 1406. If the user's credentials are accurate, the medical diagnostic kit 100 authenticates the user and pulls the scheduled appointment data from the cloud data store 1406a. FIG. 20 illustrates a user profile displayed on the display screen of the diagnostic computer 114 after the medical diagnostic kit 100 authenticates the user. If the OCC has an appointment scheduled, the OCC can start the appointment. Alternatively, the OCC can create appointments manually. Each appointment is connected to the electronic health record of the patient at the physician's remote computing device or the cloud-data store. In an embodiment, the cloud data store is HIPAA-compliant.

Figure 22:
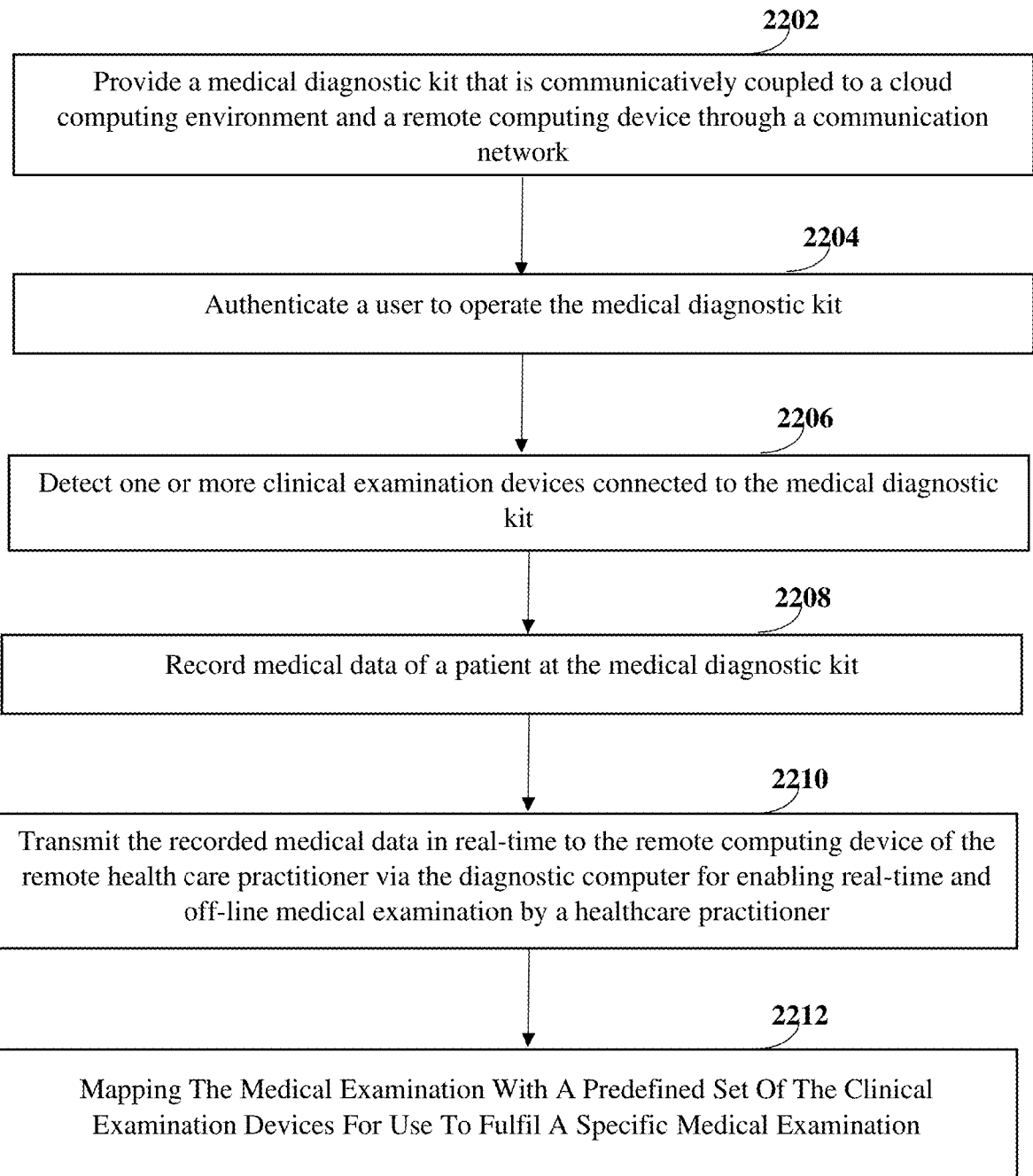
FIG. 22 illustrates a method for practicing telemedicine.

FIG. 22 illustrates a method for practicing telemedicine. The method comprises providing 2202 a medical diagnostic kit 100 that is communicatively coupled to a cloud computing environment 1406 and a remote computing device 1408 through a communication network 1404. The method further comprises authenticating 2204 a user to operate the medical diagnostic kit 100. Furthermore, the method comprises detecting 2206 one or more clinical examination devices connected to the medical diagnostic kit 100. The method further comprises recording 2208 medical data of a patient at the medical diagnostic kit 100. The medical data comprises medical data from the one or more clinical examination devices and audio-visual data from a secondary camera 147 attached to the medical diagnostic kit 100. The method further comprises transmitting 2210 the recorded medical data in real-time to the remote computing device 1408 of the remote health care practitioner via the diagnostic computer 114 for enabling both real-time and off-line medical examination by a healthcare practitioner. As used herein, off-line medical examination comprises review of the medical data of a patient stored in the cloud data store 1406a. The method further comprises mapping 2212 the medical examination of a patient with a predefined set of the clinical examination devices for use to fulfil a specific medical examination. The specific medical examination is part of a routine Chronic Condition Management program, a routine wellness examination, an annual vaccination, an annual Health Risk Assessment survey, and/or an urgent care visit. The step of mapping the medical examination further comprises mapping one or more medical procedures with the predefined set of the clinical examination devices. Examples of medical procedures comprise the auscultation procedure, electrocardiography, etc. For the auscultation procedure, the software application 1402 selects the stethoscope 122 on the diagnostic computer 114 and after the auscultation, the software application 1402 selects the internal conferencing microphone to communicate with the patient. As exemplarily illustrated in FIG. 8, an audio cable of the stethoscope 122 is connected to an USB audio card 801 via the stethoscope interface component 802. The audio card 801 is configured to transmit the second audio signal from the stethoscope 122 to the remote computing device 1408 of the remote health care practitioner via the diagnostic computer 114. For the software application 1402 selects the electrocardiography procedure, electrocardiograph (ECG) 119 and instructs the operator of the medical diagnostic kit 100 to connect the leads of the electrocardiograph (ECG) 119 to the patient. The electrical activity of the heart of the patient is transmitted to the remote computing device 1408 of the remote health care practitioner via the diagnostic computer 114. As described above, the medical data, for example, the second audio signal and the electrical activity of the heart are also transmitted to the cloud data store 1406a.

In an embodiment, during a telemedicine session, the software application 1402 allows a remote health care practitioner to remotely instruct an operator, for example, the OCC, of the medical diagnostic kit 100 to perform one or more procedures and/or specific medical examinations by using a predefined set of the clinical examination devices. Typically, such instructions to the operator of the medical diagnostic kit 100 are traditionally issued verbally, for example, through a voice connection, cell phone connection, etc. The software application 1402 allows the remote health care practitioner to issue such instructions through a GUI rendered by the software application 1402 on the diagnostic computer 114 of the medical diagnostic kit 100. Providing instructions through the GUI rendered by the software application 1402 eliminates human error that may be caused when a verbal instruction is misunderstood, misheard, etc.

Figure 23:
FIG. 23 illustrates a Graphical User Interface (GUI) rendered by the software application on a display screen of the diagnostic computer showing specific medical examinations and procedures suggested by a health care practitioner.
Figure 23:
Figure 23:
Figure 23:
Figure 25:
FIG. 25 illustrates a Graphical User Interface (GUI) rendered by the software application showing an order of the clinical examination devices that should be used for the selected procedure.
Figure 25:
Figure 25:
Figure 25:
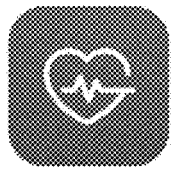
Figure 25:
Figure 25:
Figure 25:
Figure 26:
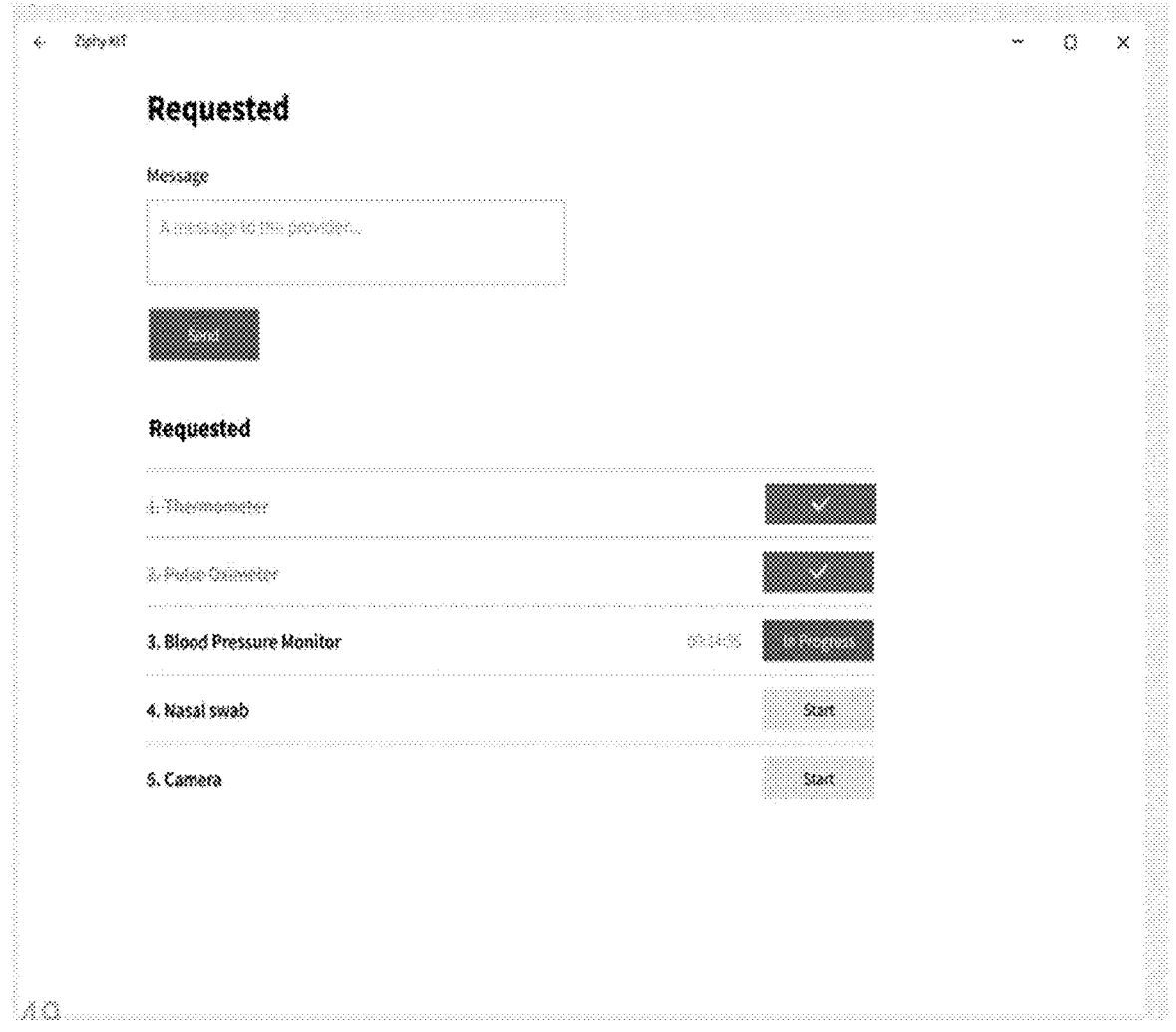
FIG. 26 illustrates a Graphical User Interface (GUI) rendered by the software application on the display screen of the diagnostic computer showing the procedures requested by the remote health care practitioner.

FIG. 23 illustrates a Graphical User Interface (GUI) rendered by the software application 1402 on a display screen of the diagnostic computer 114 showing specific medical examinations and procedures suggested by a health care practitioner. FIG. 24 illustrates a Graphical User Interface (GUI) rendered by the software application 1402 showing instructions issued remotely to an operator by a remote health care practitioner for a selected procedure. As shown in FIG. 24, the procedure selected is a "Health Check-up" for the patient. FIG. 24 shows the order of steps that the operator should perform, for example, filling an intake form, obtaining payment details such as insurance or other payment, updating symptoms, etc. FIG. 24 also shows the order of clinical examination devices to be used, for example, use Thermometer, followed by Pulse Oximeter, Blood Pressure Monitor, Weight Scales, Stethoscope, Camera, etc. FIG. 25 illustrates a Graphical User Interface (GUI) rendered by the software application 1402 showing an order of the clinical examination devices that should be used for the selected procedure. The operator of the medical diagnostic kit 100 taps on the GUI of the software application 1402 to select a specific medical examination, procedure, or clinical examination device on the GUI as directed by the remote health care practitioner. In another embodiment, the remote health care practitioner may directly select the same specific medical examination, procedure, or clinical examination device on a GUI of his or her Remote Computing Device 1408. The selection made by the remote health care practitioner on the GUI of his or her Remote Computing Device 1408 is reflected on the GUI rendered by the software application 1402 on the display screen of the diagnostic computer 114 so that the order, reason and medical code used for specific medical examination, procedure, or clinical examination device is reflected in the transaction log and/or appointment log for medical coding used during the billing process for creation of either the intermediary bill or the final bill.

As used herein, medical codes are numbers assigned to every task and service a health care practitioner, for example, a doctor, an OCC, etc., may provide to a patient including medical, surgical, and diagnostic services. Medical codes are used by insurers to determine the amount of reimbursement that a health care practitioner will receive by an insurer for that service. Since everyone uses the same codes to mean the same task or service, the medical codes ensure uniformity, and help in both tracking and billing purposes.

Figure 27:
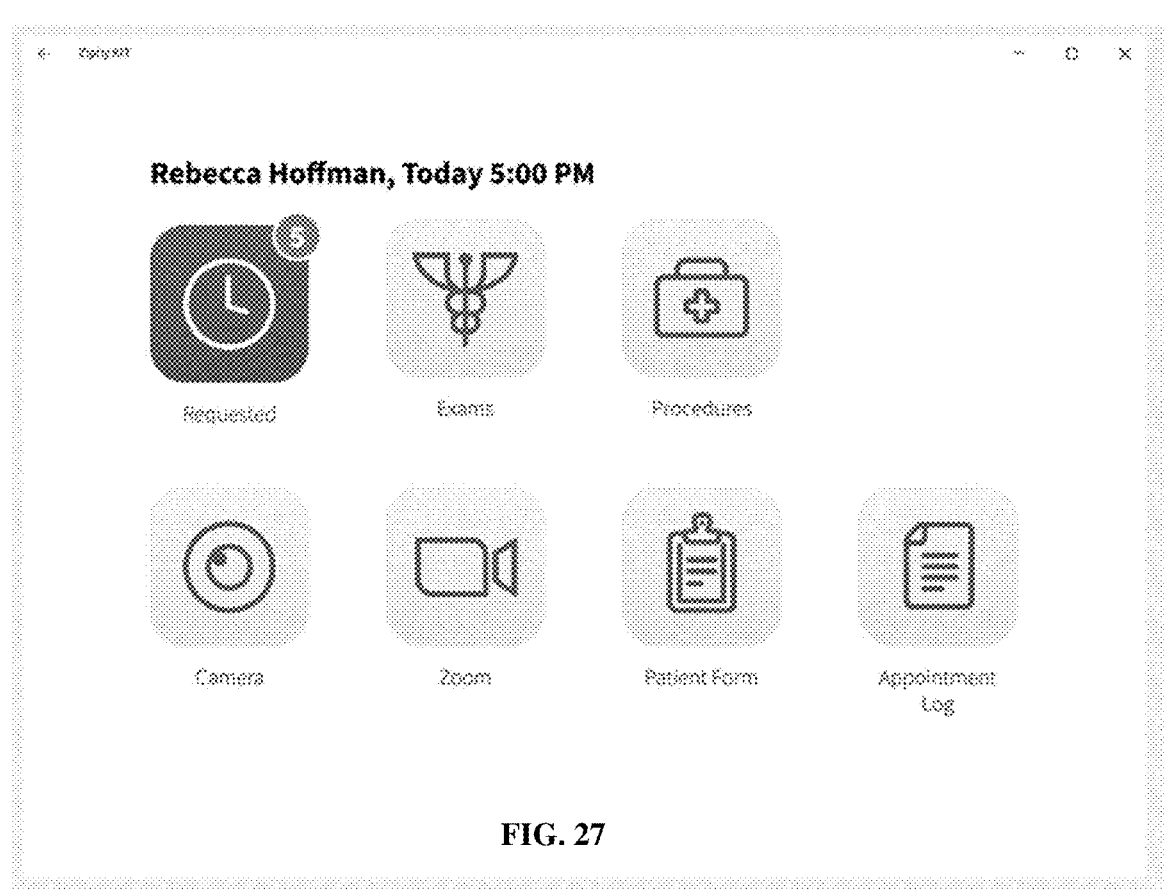
FIG. 27 illustrates a GUI rendered on the display screen of the Remote Computing Device of the remote health care practitioner.
Figure 28:
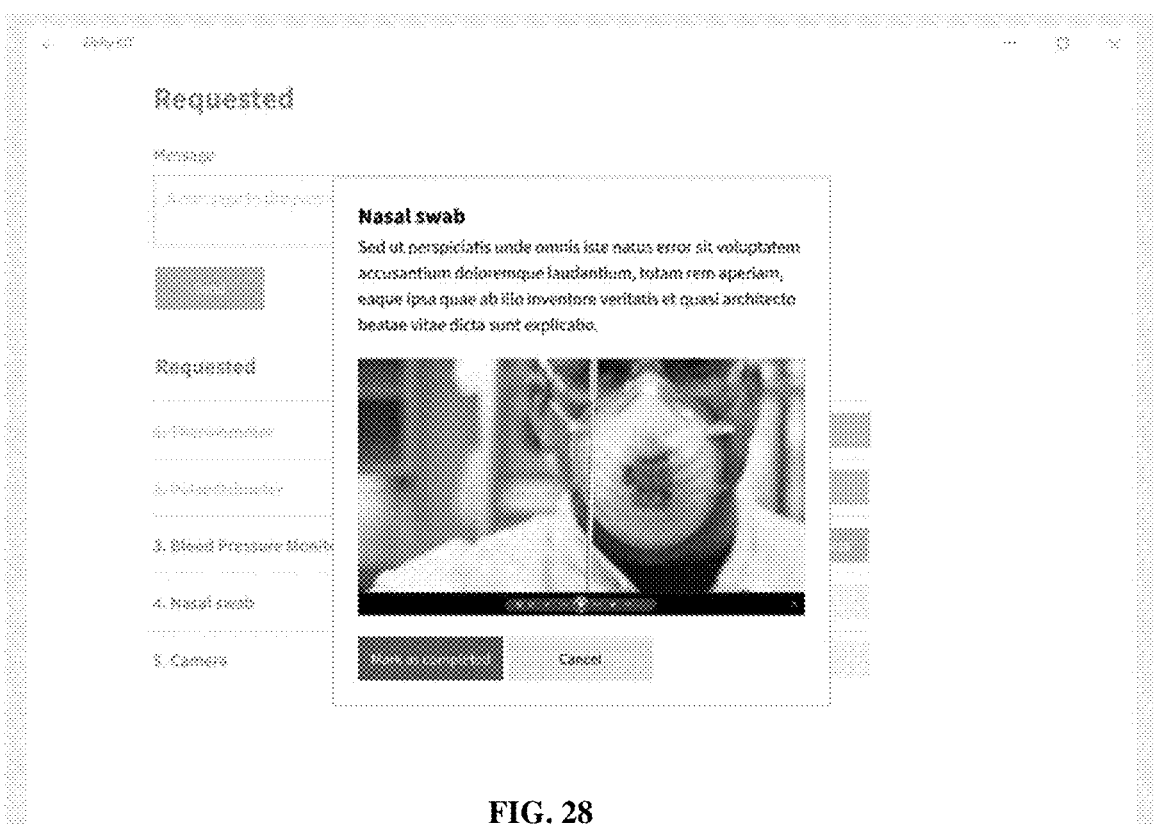
FIG. 28 illustrates a command window displayed by the software application showing textual and video instructions on how to perform a procedure requested by the remote health care practitioner.

The order or sequence of selecting the specific medical examination, procedure, or clinical examination device, and the reason for that order or sequence is recorded, regardless of whether it is the remote health care practitioner that taps on the buttons on the GUI of the Remote Computing Device 1408 or if it is the operator of the medical diagnostic kit 100 that taps on the GUI on the diagnostic computer 114 of the Medical Diagnostic Kit 100, as a result of the verbal instruction from the remote health care practitioner. When the remote health care practitioner taps on the buttons on the GUI of the Remote Computing Device 1408, there is no need for operator to even determine if the remote health care practitioner speaks the same language as the operator. Even if the remote health care practitioner speaks the same language as the operator, there is no need for the operator to understand what the as the remote health care practitioner speaks. FIG. 27 illustrates a GUI rendered on the display screen of the Remote Computing Device of the remote health care practitioner. FIG. 28 illustrates a command window displayed by the software application showing textual and video instructions on how to perform a procedure requested by the remote health care practitioner. The command window illustrated in FIG. 28 pops up as a result of the remote health care practitioner pressing a button on the GUI of the Remote Computing Device 1408 or the operator pressing a button on the GUI on the diagnostic computer 114 in response to the instructions received from the remote health care practitioner. As shown in FIG. 28, the command window has both textual and video instructions on how to perform a procedure requested by the remote health care practitioner. The textual and video instructions further eliminate human error by the operator.

The embodiments disclosed herein are configured to operate in a network environment comprising one or more computing devices that are in communication with one or more clinical examination devices, accessories, and/or a storage platform via a network. In an embodiment, the devices communicate with each other directly or indirectly, via a wired medium or a wireless medium such as the Internet, a local area network (LAN), a wide area network (WAN) or the Ethernet, satellite internet, or via any appropriate communications mediums or combination of communications mediums. Each of the devices comprises processors and communication components that are adapted to communicate with other devices. In an embodiment, each of the devices is equipped with a network communication device, for example, a network interface card, a modem, or other network connection device suitable for connecting to a network. One or more of the devices execute an operating system. While the operating system may differ depending on the type of computing device, the operating system provides the appropriate communications protocols to establish communication links with the network and the clinical examination devices. Any number and type of machines may be in communication with the computing devices. The embodiments disclosed herein are not limited to a particular computer system platform, processor, operating system, or network.

The foregoing examples and illustrative implementations of various embodiments have been provided merely for explanation and are in no way to be construed as limiting of the embodiments disclosed herein. While the embodiments have been described with reference to various illustrative implementations, drawings, and techniques, it is understood that the words, which have been used herein, are words of description and illustration, rather than words of limitation. Furthermore, although the embodiments have been described herein with reference to particular means, materials, techniques, and implementations, the embodiments herein are not intended to be limited to the particulars disclosed herein; rather, the embodiments extend to all functionally equivalent structures, methods and uses, such as are within the scope of the appended claims. It will be understood by those skilled in the art, having the benefit of the teachings of this specification, that the embodiments disclosed herein are capable of modifications and other embodiments may be effected and changes may be made thereto, without departing from the scope and spirit of the embodiments disclosed herein.

We claim:

1. A medical diagnostic kit comprising:
a casing comprising an upper shell and a lower shell connected to each other via a hinged connection, wherein the upper shell is in movable relation to the lower shell via the hinged connection between an open position and a closed position of the casing;
a universal cable storage compartment accommodated in the casing, wherein the universal cable storage compartment comprises movable dividers configured to create configurable cable compartments;
a plurality of clinical examination device and accessories accommodated in a deck positioned on the universal cable storage compartment, wherein the deck comprises a plurality of cutouts positioned in a one-to-one correspondence to the configurable cable compartments of the universal cable storage compartment, wherein the cutouts of the deck are configured to support the clinical examination devices and accessories in a plurality of configurations, and wherein cables of the plurality of clinical examination devices are accommodated without mutual entanglement in the configurable cable compartments created in the universal cable storage compartment;
multi-port hubs positioned inside the casing, wherein the multi-port hubs are configured to permanently and securely connect individual cable connectors of the clinical examination devices and the accessories and selectively power and communicate data with one or more of the clinical examination devices and the accessories;
one or more energy storage devices operably coupled to a multi-port charger inside the casing, wherein the one or more energy storage devices, when connected to a power source, are configured to receive power from the multi-port charger, and wherein the one or more energy storage devices are configured to deliver the power to the multi-port hubs via a hubs disconnection switch for powering and communicating data with the one or more of the clinical examination devices and the accessories when the casing is in the open position;
the hubs disconnection switch operably coupled to the one or more energy storage devices and the multi-port hubs, wherein the hubs disconnection switch is in operable communication with a disconnection member operably connected between the upper shell and the lower shell of the casing, and wherein the hubs disconnection switch, when activated by the disconnection member, is configured to interrupt the delivery of the power from the one or more energy storage devices to the multi-port hubs when the casing is in the closed position; and a plurality of computing devices supportably positioned in the casing, wherein one of the computing devices is a diagnostic computer configured to (a) activate one or more of the clinical examination devices; (b) execute media conference connections; (c) receive, create, record, process, store, and securely transmit medical data from the one or more of the clinical examination devices to a data store via a communication network; and (d) facilitate remote real-time medical examinations via a software application deployed on the diagnostic computer, and wherein another one of the one or more computing devices is a communication device in operable communication with the diagnostic computer via the communication network, and wherein the communication device is configured to display a media stream from the one or more of the clinical examination devices.

2. The medical diagnostic kit of claim 1, wherein the upper shell of the casing comprises an upper support wall adjoined by side walls oriented substantially perpendicular to the upper support wall to define an upper cavity, and wherein the lower shell of the casing comprises a lower support wall adjoined by side walls oriented substantially perpendicular to the lower support wall to define a lower cavity.

3. The medical diagnostic kit of claim 2, wherein the universal cable storage compartment, the deck, the multi-port hubs, the one or more energy storage devices, an air-cooling fan system, a power distribution board, a hubs disconnection switch board, a stethoscope interface component, and the multi-port charger are accommodated in the lower cavity defined by the lower shell of the casing, and wherein the computing devices are supportably positioned in the upper cavity defined by the upper shell of the casing.

4. The medical diagnostic kit of claim 1, further comprising a side door hinged to a door frame exteriorly positioned on a side wall of the casing, wherein the side door is configured to close and protect inlet ports and outlet ports of the medical diagnostic kit.

5. The medical diagnostic kit of claim 4, wherein the inlet ports comprise an air intake port with a particle filter and an alternating current fused inlet, and wherein the alternating current fused inlet is configured to provide the power from the power source to the multi-port charger for charging the one or more energy storage devices, the computing devices, the clinical examination devices, and the accessories inside the casing, and wherein the outlet ports comprise louvers in fluid communication with an air-cooling fan system positioned in the casing and configured to direct heated internal air in an upward direction into an upper cavity defined by the upper shell of the casing without mixing with incoming external air flowing in a lower cavity defined by the lower shell of the casing for optimal cooling in the medical diagnostic kit.

6. The medical diagnostic kit of claim 1, further comprising a fan protector affixed to the deck, wherein the fan protector is configured to protect an exhaust fan of an air-cooling fan system interiorly positioned proximal to a side wall of the casing and supported by a fan backplate.

7. The medical diagnostic kit of claim 1, further comprising air circulation holes configured proximal to an edge of the deck, wherein the air circulation holes are configured to assist in movement of forced air provided by an air-cooling fan system, from a lower cavity defined by the lower shell of the casing to an upper cavity defined by the upper shell of the casing, during charging of the computing devices, the clinical examination devices, and the accessories powered by the multi-port charger.

8. The medical diagnostic kit of claim 1, further comprising a cushioning member comprising slots positioned on the deck in correspondence to the configurable cable compartments of the universal cable storage compartment, wherein the slots of the cushioning member are configured according to shapes of the clinical examination devices and the accessories to protectively accommodate the clinical examination devices and the accessories in the plurality of configurations.

9. The medical diagnostic kit of claim 1, wherein the communication device is a tablet computing device comprising a display unit configured to assist in aiming a camera lens of one of the clinical examination devices and visualizing one or more of a plurality of organs of a patient, and wherein the display unit is configured to receive and display a media stream of each of the visualized one or more of the organs captured by the one of the clinical examination devices via the camera lens.

10. The medical diagnostic kit of claim 1, wherein the communication device is configured to remotely control the software application deployed on the diagnostic computer.

11. The medical diagnostic kit of claim 1, further comprising a removable device holder lockably positioned in the casing, wherein the removable device holder is configured to accommodate the communication device, and when the removable device holder is unlocked and removed from the casing along with the communication device, the removable device holder assists in attaching the communication device to one or more of the clinical examination devices.

12. The medical diagnostic kit of claim 1, further comprising a device holder pivotably connected to the casing, wherein the device holder is configured to accommodate the diagnostic computer, and wherein the device holder is configured to assist in aiming a camera of the diagnostic computer when pivoted.

13. The medical diagnostic kit of claim 1, further comprising a non-removable device holder positioned in the casing, wherein the non-removable device holder is configured to accommodate another one of the computing devices, and wherein the another one of the computing devices is a network-enabled mobile phone configured to provide access of the communication network to the diagnostic computer and the communication device.

14. The medical diagnostic kit of claim 1, further comprising a primary hub operably coupled to the multi-port charger, the diagnostic computer, and the multi-port hubs, wherein the primary hub is configured to receive the power from the multi-port charger and deliver the power to the diagnostic computer for charging the diagnostic computer and executing data communication between the diagnostic computer and the clinical data examination devices and the accessories.

15. The medical diagnostic kit of claim 1, wherein each of the multi-port hubs comprises a plurality of universal serial bus switchable ports configured to permanently and securely connect the individual cable connectors of the clinical examination devices and the accessories and selectively power and communicate data with the one or more of the clinical examination devices and the accessories.

16. The medical diagnostic kit of claim 1, further comprising a headset jack positioned at a predetermined mounting location in the casing, wherein the headset jack is configured to connect a headset for use during auscultation.

17. The medical diagnostic kit of claim 1, further comprising a stethoscope interface component operably coupled to one of the multi-port hubs via an audio card for executing a remote auscultation using a stethoscope accommodated in one of the cutouts on the deck, wherein the stethoscope is charged by the multi-port charger within the casing via the stethoscope interface component, and wherein the stethoscope interface component comprises:

an audio splitter operably coupled to the stethoscope for receiving a stethoscope signal from the stethoscope during the remote auscultation and splitting the stethoscope signal into a first audio signal and a second audio signal, wherein the first audio signal is transmitted to a headset, and wherein the second audio signal is transmitted to the audio card via an audio switch, and wherein the audio card is configured to transmit the second audio signal to a remote computing device via the diagnostic computer;

the audio switch configured to select between the second audio signal and a microphone signal from the headset for transmission to the audio card; and a decoder operably coupled to an audio control element of the headset, wherein the decoder is configured to decode a control signal received from the audio control element and operate the audio switch.

18. The medical diagnostic kit of claim 1, further comprising an auxiliary port positioned at a predetermined mounting location in the casing, wherein the auxiliary port is configured to facilitate external connections to one of the multi-port hubs, and wherein the auxiliary port is operably coupled to the one of the multi-port hubs for delivering power to the external connections and executing data exchange with the external connections.

19. The medical diagnostic kit of claim 1, wherein the multi-port charger is electrically connected to and configured to charge the one or more energy storage devices, the computing devices, the clinical examination devices, and the accessories.

20. The medical diagnostic kit of claim 1, further comprising an air-cooling fan system comprising cooling fans positioned in the lower cavity and the upper cavity of the casing, wherein the air-cooling fan system is configured to produce an air flow within the lower cavity and the upper cavity of the casing for cooling the multi-port charger, the one or more energy storage devices, the computing devices, the clinical examination devices, and the accessories to prevent overheating thereof when the casing is in the closed position during charging.

21. The medical diagnostic kit of claim 1, wherein the clinical examination devices comprise a stethoscope, an electrocardiogram otoscope, an ultrasound device, a thermometer, a blood pressure monitor, an oximeter, a throat exam camera, a skin exam camera, and a secondary camera, and wherein the accessories comprise one or more input devices and one or more output devices configured to interface with one or more of the computing devices; and electrocardiograph electrodes; and wherein the one or more input devices comprise a headset and a wireless keyboard, and wherein the one or more output devices comprise a wireless speaker.

22. The medical diagnostic kit of claim 21, wherein the secondary camera extends from a flexible mount in the casing, and wherein the flexible mount is configured to aim a camera lens of the secondary camera towards a patient and allow a health care practitioner at a remote site to view the patient when the patient is out of view of a camera of the diagnostic computer, and wherein the secondary camera is operably coupled to one of the multi-port hubs using an internal power supply and data communication cable positioned in the flexible mount.

23. The medical diagnostic kit of claim 1, further comprising illuminating control elements operably coupled to switchable ports of the multi-port hubs and configured to one of activate and deactivate the one or more of the clinical examination devices and one or more of the accessories to save battery power and provide visual information to an operator about the switchable ports being energized.

24. The medical diagnostic kit of claim 1, further comprising a magnetic charging connector system comprising one or more magnetic connectors operably coupled to the multi-port charger and magnetically engageable to one or more of the clinical examination devices and the accessories positioned proximal to the one or more magnetic connectors to create an electrically conductive relationship therebetween, wherein each of the one or more magnetic connectors comprises:

a first magnetic connecting element protruding from each of one or more of the cutouts of the deck; and a second magnetic connecting element operably coupled to a connector section of a battery of each of the one or more of the clinical examination devices and the accessories, wherein the second magnetic connecting element, when in close proximity to the first magnetic connecting element is configured to magnetically attract the first magnetic connecting element for receiving the power delivered by the multi-port charger.

25. The medical diagnostic kit of claim 1, wherein the software application is configured to display, on the diagnostic computer, a panel of the clinical examination devices and the accessories accommodated in the medical diagnostic kit and indications of one or more of the clinical examination devices and the accessories on the panel suggested by a health care practitioner at a remote site for usage during the remote real-time medical examinations.

\*    \*    \*    \*    \*